(12) United States Patent
Payne et al.

(10) Patent No.: US 11,298,441 B2
(45) Date of Patent: Apr. 12, 2022

(54) BIODEGRADABLE BIOMIMETICS OF GROWTH PLATE CARTILAGE FOR THE TREATMENT OF PHYSEAL INJURIES

(71) Applicant: THE REGENTS OF THE UNIVERSITY OF COLORADO, A BODY CORPORATE, Denver, CO (US)

(72) Inventors: Karin A. Payne, Denver, CO (US); Stephanie Bryant, Boulder, CO (US); Virginia Ferguson, Golden, CO (US); Nancy Hadley-Miller, Denver, CO (US); Robert McLeod, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 16/762,835

(22) PCT Filed: Nov. 6, 2018

(86) PCT No.: PCT/US2018/059466
§ 371 (c)(1),
(2) Date: May 8, 2020

(87) PCT Pub. No.: WO2019/094389
PCT Pub. Date: May 16, 2019

(65) Prior Publication Data
US 2020/0261623 A1    Aug. 20, 2020

Related U.S. Application Data

(60) Provisional application No. 62/591,251, filed on Nov. 28, 2017, provisional application No. 62/583,055, filed on Nov. 8, 2017.

(51) Int. Cl.
*A61L 27/52* (2006.01)
*A61K 38/48* (2006.01)
*A61L 27/48* (2006.01)
*A61L 27/58* (2006.01)
*B33Y 80/00* (2015.01)

(52) U.S. Cl.
CPC .......... *A61L 27/52* (2013.01); *A61K 38/4886* (2013.01); *A61L 27/48* (2013.01); *A61L 27/58* (2013.01); *A61L 2300/236* (2013.01); *A61L 2300/25* (2013.01); *A61L 2300/414* (2013.01); *A61L 2300/416* (2013.01); *A61L 2430/06* (2013.01); *B33Y 80/00* (2014.12)

(58) Field of Classification Search
CPC .......... A61L 27/52; A61L 27/48; A61L 27/58; A61L 2300/236; A61L 2300/25; A61L 2300/414; A61L 2300/416; A61L 2430/06; A61L 27/54; A61L 27/3834; A61L 2300/412; A61K 38/4886; A61K 35/28; A61K 38/1841; B33Y 80/00; C12M 23/04
See application file for complete search history.

(56) References Cited

U.S. PATENT DOCUMENTS

| | | | |
|---|---|---|---|
| 2009/0208577 A1 | 8/2009 | Xu et al. | |
| 2012/0089238 A1* | 4/2012 | Kang | B29C 64/112 623/23.72 |
| 2015/0291929 A1* | 10/2015 | Murphy | G01N 33/4833 435/7.23 |
| 2016/0038544 A1 | 2/2016 | Keller et al. | |

OTHER PUBLICATIONS

Zhang et al. "Cartilage Repairand Subchondral Bone Migration Using 3D Printing Osteochondral Composites: a One-Year-Period Study in Rabbit Trochlea," BioMed Research International, Aug. 7, 2014 (Aug. 7, 2014), vol. 2014, pp. 1-16. (Year: 2014).*
Broughton et al. "Epiphyseolysis For Partial Growth Plate Arrest: Epiphyseolysis for Partial 16, 18 Growth Plate Arrest. Results After Four Years or at Maturity," The Journal of Bone and Joint Surgery, Jan. 1, 1989 (Jan. 1, 1989), vol. 71, No. 1, pp. 13-16. (Year: 1989).*
Izadifar et al. "Analyzing Biological Performance of 3D-Printed, Cell-Impregnated Hybrid Constructs for Cartilage Tissue Engineering", Tissue Engineering: Part C, vol. 22, No. 3, pp. 1-16, 2016.
Neumann et al., "Nondestructive evaluation of a new hydrolytically degradable and photo-clickable PEG hydrogel for cartilage tissue engineering", Acta Biomater. vol. 39 pp. 1-11, 2016.
Pascual-Garrido et al., "Cartilage Repair with Mesenchymal Stem Cells (MSCs) Delivered in a Novel Chondroitin Sulfate/Polyethylene Glycol Hydrogel in a Rabbit Animal Model", The Orthopaedic Journal of Sports Medicine, vol. 5, No. 7, pp. 1-2, 2017.
Pascual-Garrido et al., "Mesenchymal Stem Cells (MSCs) Delivered in a Novel Hydrogel for the Treatment of Chondral Defects in a Rabbit Animal Model", ORS 2017 Annual Meeting Poster No. 2362, 1 page.

\* cited by examiner

*Primary Examiner* — Quanglong N Truong
(74) *Attorney, Agent, or Firm* — Polsinelli PC

(57) ABSTRACT

The present invention relates to the unexpected discovery of 3D printed biomimetics of growth plate cartilage and methods using the same for the treatment of growth plate defects. In certain embodiments, the methods prevent the growth of bony bars at the site of growth plate injury, thereby preventing growth arrest and/or deformity.

21 Claims, 37 Drawing Sheets
Specification includes a Sequence Listing.

FIG. 2A
FIG. 2B
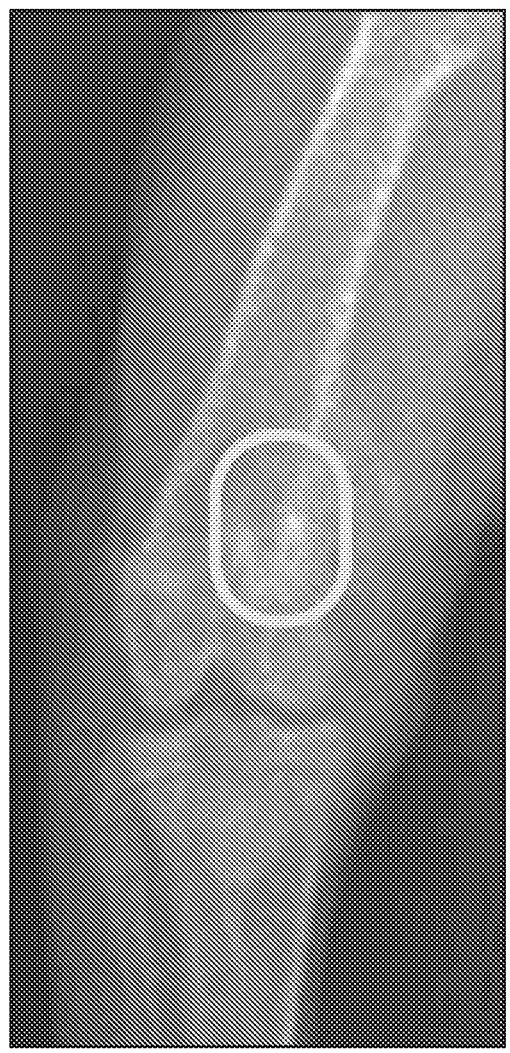

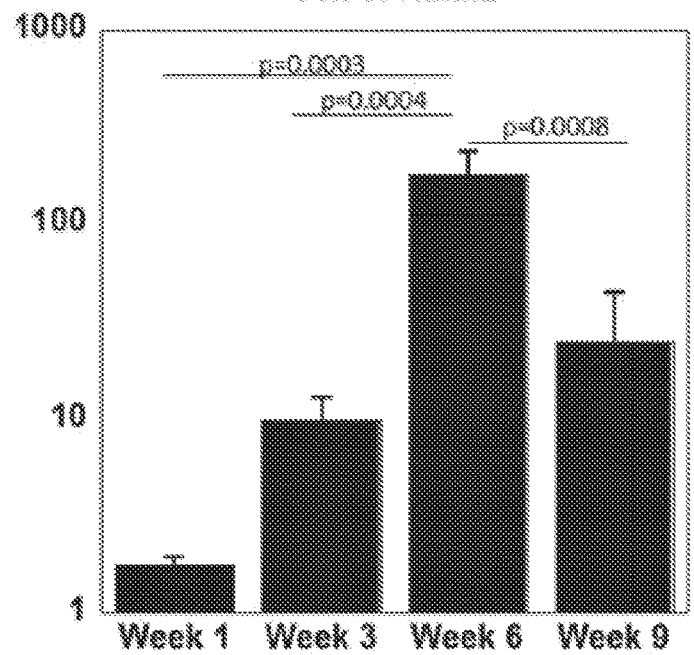
FIG. 4G
Sox 9: Runx2
FIG. 5A
| Time point | Week 1 | Week 3 | Week 6 | Week 9 |
|---|---|---|---|---|
| DNA per construct (μg) | 2.79 (33) | 2.43 (25) | 2.62 (29) | 2.31 (27) |
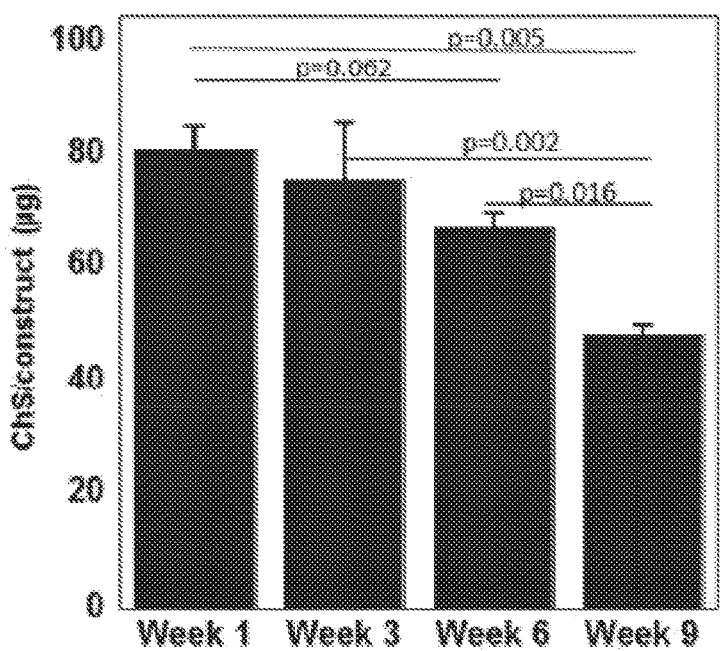
FIG. 5B Week 1

Week 3

Week 6

Week 9

| Time of Treatment | Initial | 1 minute | 2 minutes | 3 minutes |
|---|---|---|---|---|
| Contact Angle Measurements | 78 (2) | 43 (2) | 31 (1) | 10 (2) |

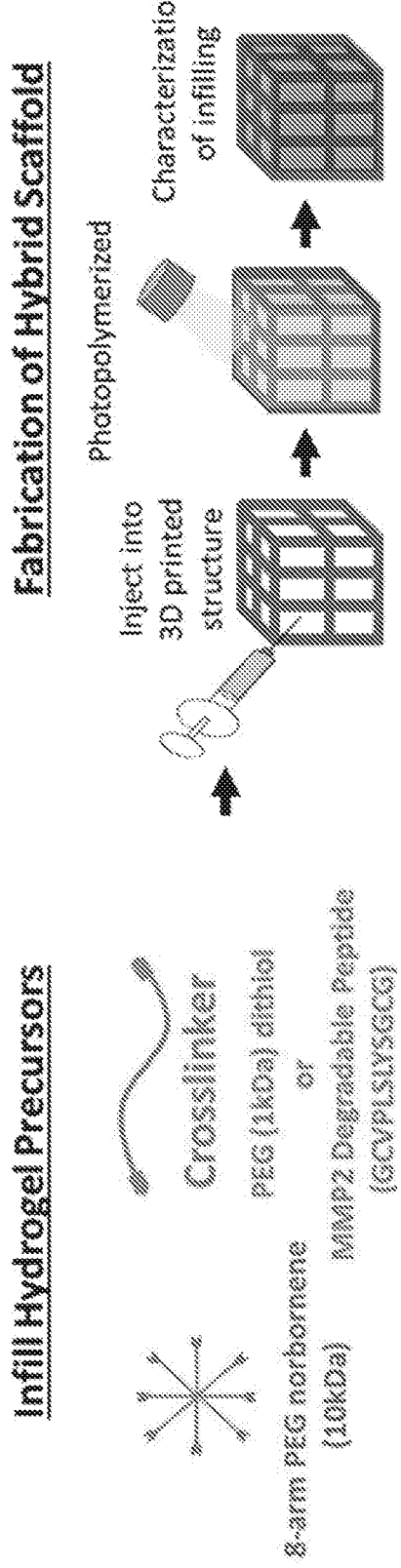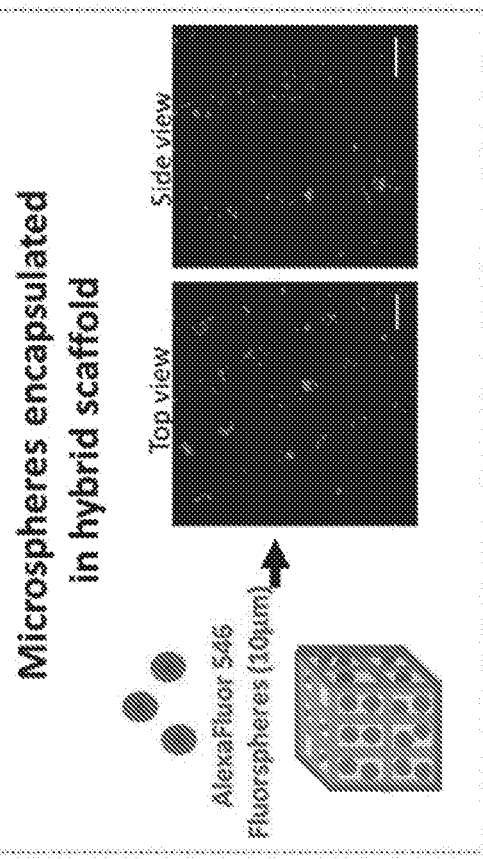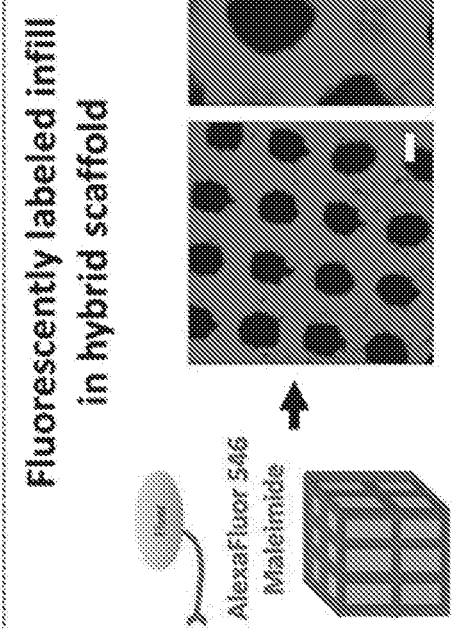
FIG. 11A
FIG. 11B
FIG. 11C

Empty

Filled

Empty

Free Swelling    Loading

Filled

Free Swelling    Loading

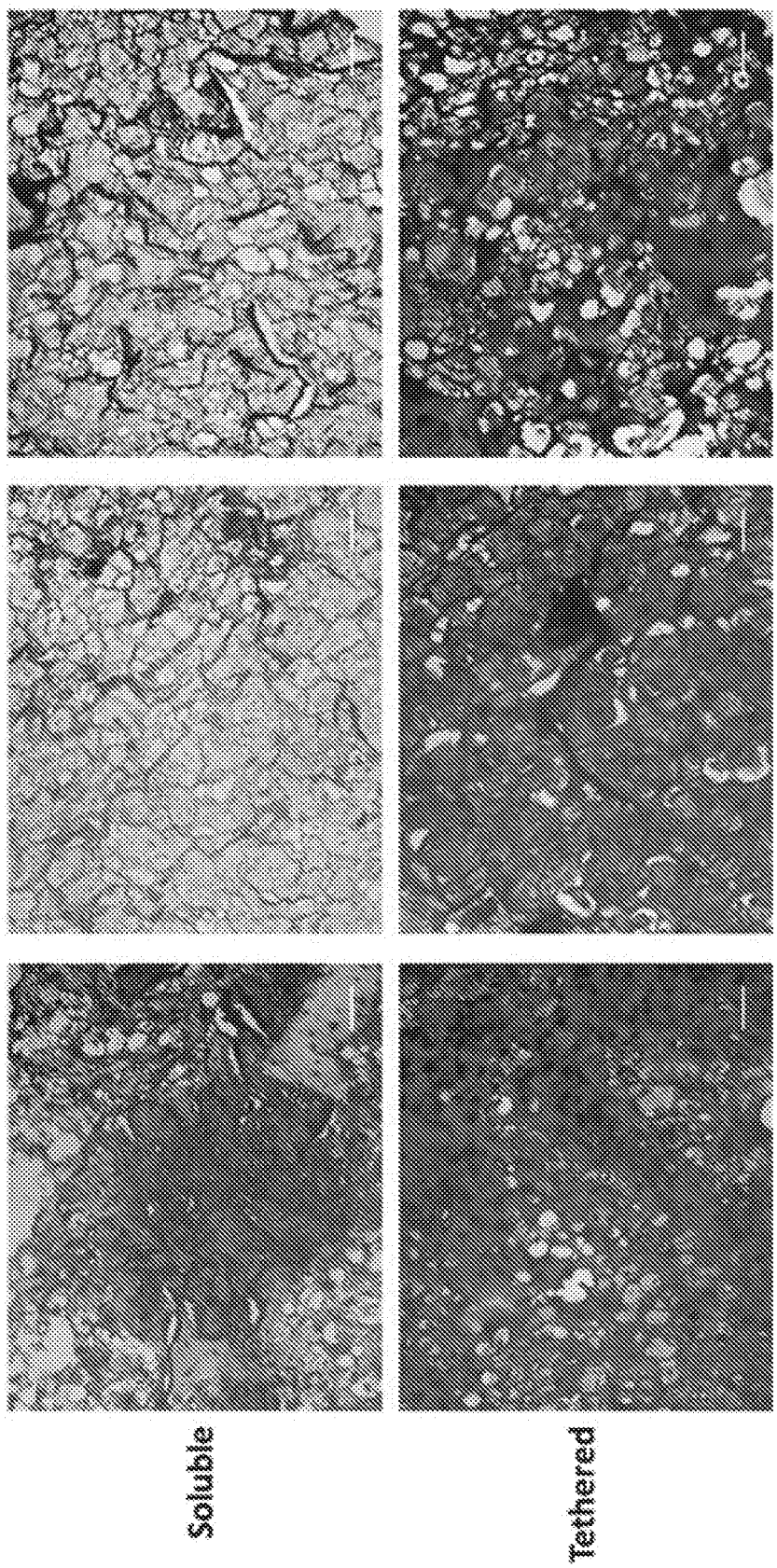

BIODEGRADABLE BIOMIMETICS OF GROWTH PLATE CARTILAGE FOR THE TREATMENT OF PHYSEAL INJURIES

CROSS-REFERENCE TO RELATED APPLICATIONS

The present application is a 35 U.S.C. § 371 national phase application from, and claims priority to, International Application No. PCT/US2018/059466, filed Nov. 6, 2018, which claims priority under 35 U.S.C. § 119(e) to U.S. Provisional Application Nos. 62/583,055, filed Nov. 8, 2017, and 62/591,251, filed Nov. 28, 2017, all of which applications are hereby incorporated by reference herein in their entireties.

INCORPORATION BY REFERENCE OF SEQUENCE LISTING

This application contains a Sequence Listing that has been submitted in ASCII format via EFS-Web and is hereby incorporated by reference in its entirety. The ASCII copy, created on Nov. 30, 2021, is named 106549-674710_CU4539H-US1_SequenceListing_ST25.txt and is 4000 bytes in size.

STATEMENT REGARDING FEDERALLY SPONSORED RESEARCH OR DEVELOPMENT

This invention was made with government support under grant numbers R21 HD090696 and R21HD092109 awarded by the National Institutes of Health. The government has certain rights in the invention.

BACKGROUND OF THE INVENTION

The growth plate or epiphyseal plate is found at the end of all long bones, and provides signals for long bones to lengthen as a child grows. It is made of cartilaginous tissue, and is the most fragile structure in a child's developing bones, making it prone to injury. If the cartilage tissue in the growth plate is injured, bone tissue is deposited in the injured site, forming a "bony bar". This bony bar can stop bone growth completely, or can cause one side of the bone to grow more than the other, resulting in deformities. About 30% of all pediatric fractures affect the growth plate. Of those, 1-10% can lead to growth arrest or deformity. Current surgical methods to correct bone growth defects are invasive, prone to infections and have low success rates. The most common surgical approach is to remove the bony bar and insert a fat graft in its place. The fat is not as stiff as the bone, and may allow the remaining uninjured growth plate to maintain a normal bone growth pattern. Unfortunately, the fat graft often gets dislodged or dies due to lack of vascularization. Growth problems arising from growth plate injuries are devastating to the patient and family and can result in multiple surgeries, which increases the cost of treatment.

Thus, there is a need in the art for compositions and methods of treatment that will prevent bony bar formation and allow for the regeneration of the damaged growth plate, in order to prevent growth arrest and deformities. The present invention meets these needs.

BRIEF SUMMARY OF THE INVENTION

In one aspect, the invention provides a biomimetic growth plate cartilage construct comprising a 3D printed structure in-filled with a cartilage mimetic hydrogel. In certain embodiments, the 3D printed structure comprises at least one material selected from the group consisting of poly (ethylene glycol), poly(ethylene glycol) diacrylate, poly (ethylene glycol) methacrylate, dithiolated hydrocarbons, trithiolated hydrocarbons, and tetrathiolated hydrocarbons. In other embodiments, the cartilage mimetic hydrogel comprises at least one multifunctional monomer and at least one degradable cross-linker.

In certain embodiments, the 3D printed structure is printed into a pattern or shape selected from the group consisting of a honeycomb, grid, and mesh. In other embodiments, the 3D printed structure comprises at least one biodegradable material.

In certain embodiments, the at least one multifunctional monomer comprises at least one material selected from the group consisting of poly(ethylene glycol), poly(ethylene glycol) diacrylate, poly(ethylene glycol) methacrylate, acryloyl-PEG-RGD, norbornene functionalized PEG.

In certain embodiments, the at least one degradable cross-linker is an enzyme degradable peptide. In other embodiments, the enzyme degradable peptide is a peptide that can be degraded by at least one matrix metalloproteinase. In yet other embodiments, the enzyme degradable peptide is selected from the group consisting of GCVPLSLYSGCG (SEQ ID NO: 13), CVPLSLYSGC (SEQ ID NO: 14) and CRGDS (SEQ ID NO: 15).

In certain embodiments, the cartilage mimetic hydrogel comprises at least one biomimetic moiety selected from the group consisting of chondroitin sulfate, thiolated chondroitin sulfate, methacrylated chondroitin sulfate, and cell adhesion peptide RGD.

In certain embodiments, the cartilage mimetic hydrogel comprises at least one biological factor selected from the group consisting of SDF-1α, CCL25, TGF-β1, TGF-β3, ranibizumab, bevacizumab, lapatinib, sunitinib, sorafenib, axitinib, and pazopanib. In other embodiments, at least a portion of the at least one biological factor is covalently bound to the cartilage mimetic hydrogel.

In certain embodiments, the cartilage mimetic hydrogel further comprises mesenchymal stem cells.

In another aspect, the invention provides a method of treating cartilage injuries in a subject. In certain embodiments, the method comprises placing a construct of the invention in a void at the site of the cartilage injury. In other embodiments, the cartilage injury is a growth plate injury.

In certain embodiments, before the placing step, a bony bar is first surgically removed from the growth plate injury in the subject, thus generating at least in part the void. In other embodiments, before the placing step, damaged growth plate cartilage is first surgically removed from the site of the growth plate injury, thus generating, at least in part, the void.

In certain embodiments, the method prevents the growth of bony bars in cartilage tissue at the site of growth plate injury. In other embodiments, the method treats or prevents the arrest of bone growth at the site of growth plate injury. In yet other embodiments, the method treats or prevents the arrest of bone elongation at the site of growth plate injury. In yet other embodiments, the method treats or prevents bone deformities at the site of growth plate injury.

In certain embodiments the subject is a mammal. In other embodiments, the subject is a human. In yet other embodiments, the subject is an infant, toddler, child, juvenile, adolescent or young adult.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 2A is an X-ray image showing the surgical creation of a defect in the physeal region of a rabbit femur. FIG. 2B is an X-ray image showing formation of a bony bar at the site of the surgically created defect from FIG. 2A, 3 weeks after the creation of the defect.

FIGS. 4A-4G are graphs of gene expression of MSCs encapsulated in an MMP7 degradable hydrogel normalized to gene expression of pre-encapsulated MSCs. The chondrogenic genes SOX9, ACAN, and COL2A1, and the hypertrophic genes RUNX2 and COLXA1 were evaluated with culture time. Data are represented as the mean with error bars as standard deviation (n=3).

FIG. 5A is a table of total DNA content per construct as a function of culture time.

FIG. 5B is a graph showing sGAGs per construct shown as a function of culture time. Data are represented as the mean with standard deviation shown parenthetically or as error bars (n=3).

FIG. 11A is a schematic of the photopolymerizable PEG precursor solutions for the infill and the fabrication of the hybrid scaffold by injecting the precursors and photopolymerizing.

FIG. 11B is a schematic of the infilling of the hybrid scaffold with a fluorescently-labeled, PEG hydrogel. Representative confocal microscopy images shows successful infilling of the hydrogel (red) around the 3D printed support structure (black) (scale bar=100 μm).

FIG. 11C is a schematic of the infilling of the hybrid scaffold with fluorescently-labeled microspheres that are suspended in the infill solution and then subsequently photopolymerized to encapsulate them in the PEG hydrogel in the hybrid scaffold. Representative confocal microscopy images show the distribution of microspheres (red) through the top of the lattice (left) and a side view through the pillars (right) (scale bar=100 μm).

FIG. 13A shows the composition cultured with soluble TGF-β3 in the media; and FIG. 13B shows the composition with a thiolated TGF-β3 covalently tethered into the hydrogel.

FIGS. 15A-15B are a graph and images showing sGAGs in the hydrogel constructs over time. FIG. 15A is a graph of chondroitin sulfate (ChS) content in the hydrogels with soluble TGF-β3 (solid) or tethered TGF-β3 (striped) throughout the culture period. Data is represented as the mean with standard bars representing the standard deviation (n=3). FIG. 15B is a set of representative images of safranin O stained sections counterstained with fast green.

FIG. 16A is a set of representative immunohistochemistry images of collagen II (left) and PEG (right) when cultured with tethered TGF-β3 and with soluble TGF-β3 in the media at week 3, 6, and 9. (scale bar=20 μm) FIG. 16B is a graph showing a semi-quantitative analysis of immunohistochemistry images of the percent area of collagen II. FIG. 16C is a graph PEG per cell at week 3, 6, and cultured with soluble TGF-β3 (black) and tethered TGF-β3 (striped). Data shown as mean with error bars representing standard deviation.

DETAILED DESCRIPTION OF THE INVENTION

Figure 1A:
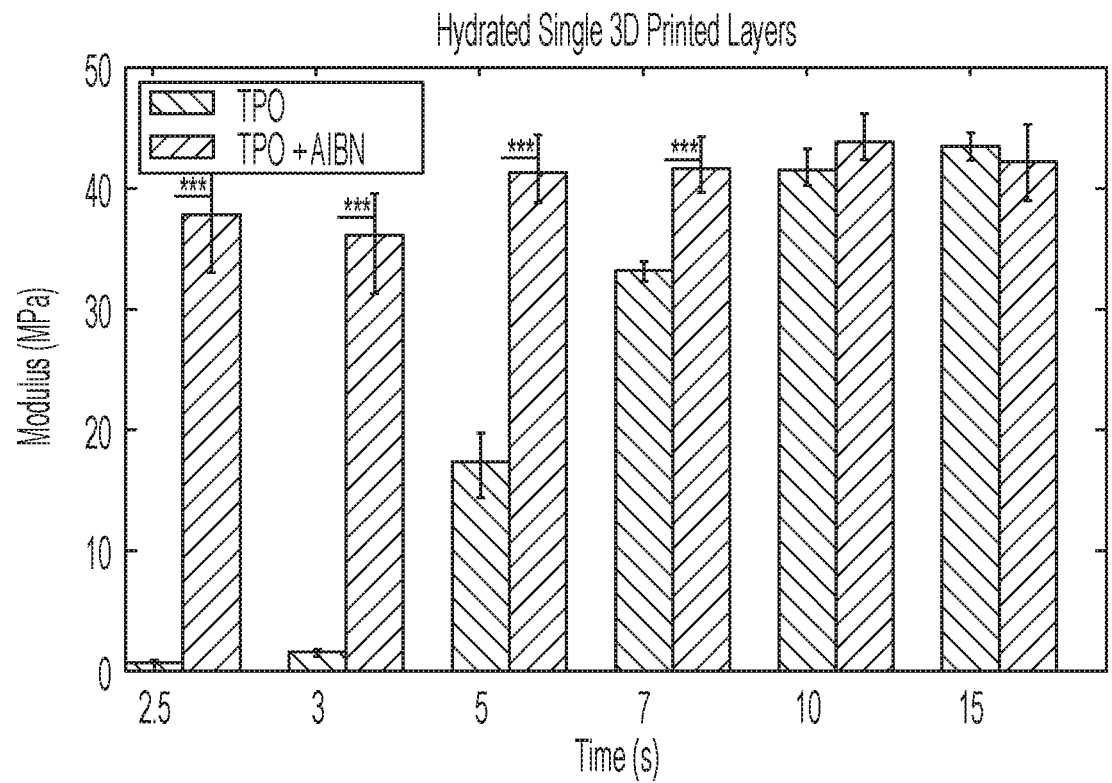
FIG. 1A is a graph showing the elastic modulus of hydrated single 3D printed layers of the stiff polymer structure reported in Example 1, both with and without added thermal initiator (AIBN).

The present invention relates to the unexpected discovery of 3D printed biomimetics of growth plate cartilage and methods using the same for the treatment of growth plate defects. In certain embodiments, the methods prevent the growth of "bony bars" at the site of growth plate injury, thereby preventing growth arrest and/or deformity.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in pharmacology and tissue engineering are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "bony bar" or "physeal bar" is a premature physeal arrest, often resulting from injury or infection to an unfused physis. The bony bar consists of a bony bridge that crosses the growth plate and can result in growth abnormalities and deformities.

As used herein, the term "composition" or "pharmaceutical composition" refers to a mixture of at least one compound useful within the invention with a pharmaceutically acceptable carrier. The pharmaceutical composition facilitates administration of the compound to a patient or subject.

Multiple techniques of administering a compound exist in the art including, but not limited to, intravenous, oral, aerosol, parenteral, ophthalmic, nasal, pulmonary and topical administration.

As used herein "crosslinking" is meant to be a process of creating a bond that links one polymer chain to another.

As used herein "crosslinking agent" or "crosslinking source" is meant to be an agent that is capable of forming a chemical or ionic links between molecules. Nonlimiting examples of crosslinking agents or sources include calcium chloride; ammonium persulfate (APS) and tetramethylethylenediamine (TEMED), glutaraldehyde, epoxides, oxidized dextran, p-azido benzoylhydrazide, N[α-maleimidoacetoxy] succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl] carbodiimide hydrochloride (EDC), N-hydroxysuccinimide (NHS), visible light irradiation, ultraviolet irradiation, and combinations thereof.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" will be used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

As used herein, the term "growth plate" refers to the epiphyseal plate or the hyaline cartilage plate in the metaphysis at each end of a long bone. The growth plate is the portion of the bone where new bone growth takes place, thereby elongating the bone. The terms "growth plate" and "physis" are to be used interchangeably.

As used herein, the term "growth plate injury" refers to an injury to the epiphyseal plate or the hyaline cartilage plate in the metaphysis at each end of a long bone. The terms "growth plate injury" and "physeal injury" are to be used interchangeably.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: AIBN, azobisisobutyronitrile; bFGF, basic fibroblast growth factor; BM-MSCs, bone marrow mesenchymal stem cells; ChS, chondroitin sulfate A; ChS-SH, thiolated chondroitin sulfate; DIEA, N,N-diisopropylethylamine; DMEM, Dulbecco's modified Eagle media; DTP, dithiobis(propanoic dihydrazide); DTT, dithiothreitol; EDCI, 1-ethyl-3-(3-dimethylaminopropyl) carbodiimide; HATU, 1-[Bis (dimethylamino) methylene]-1H-1,2,3-triazolog[4,5-b] pyridinium 3-oxid hexafluorophosphate; hMSC, human mesenchymal stem cell, LAP, lithium phenyl-2,4,6-trimethylbenzoylphosphinate; μCT, micro computed tomography; MSC, mesenchymal stem cell; PBS, phosphate buffer saline; PEG, poly(ethylene glycol); PEGDA, poly(ethylene glycol) diacrylate; RGD, arginine-glycine-aspartic acid; sGAGs, sulfated glycosaminoglycans; TPO, trimethylbenzoyl diphenylphosphine oxide.

Constructs

The invention provides biomimetic cartilage constructs for the treatment of pediatric physeal injuries and/or cartilage injuries. In certain embodiments, the biomimetic constructs comprise a 3D printed structure that is in-filled with a cartilage mimetic hydrogel. In certain embodiments, the biomimetic cartilage constructs are biomimetic growth-plate cartilage constructs.

In certain embodiments, the 3D printed structure is stiff or rigid, and provides the construct with structural support to prevent collapse. In certain embodiments, the 3D printed structure comprises at least one biodegradable material. In other embodiments, the 3D printed structure comprises at least one oligomeric material functionalized with at least one functionality selected from the group consisting of acrylate, methacrylate, thiol and norbornene. In yet other embodiments, the 3D printed structure comprises poly(ethylene glycol) functionalized with at least one functionality selected from the group consisting of acrylate, methacrylate, and norbornene. In yet other embodiments, the 3D printed structure comprises at least one hydrocarbon oligomer functionalized with at least one thiol functionality. In yet other embodiments, the 3D printed structure comprises one or more materials selected from the group consisting of: poly (ethylene glycol), poly(ethylene glycol) diacrylate, poly (ethylene glycol) methacrylate, dithiolated hydrocarbons, trithiolated hydrocarbons and tetrathiolated hydrocarbons.

In certain embodiments, the 3D printed structure is printed into a pattern or shape selected from the group consisting of a honey comb, grid, and mesh. In certain embodiments, the 3D printed structure is formed using stereolithography.

In certain embodiments, the cartilage mimetic hydrogel is softer than the 3D printed structure. In certain embodiments, the cartilage mimetic hydrogel comprises at least one multifunctional monomer and at least one degradable cross-linker. In other embodiments, the cartilage mimetic hydrogel comprises poly(ethylene glycol) functionalized with at least one functionality selected from the group consisting of acrylate, methacrylate, and norbornene. In yet other embodiments, the cartilage mimetic hydrogel comprises chondroitin sulfate functionalized with at least one functionality selected from the group consisting of acrylate, methacrylate, and norbornene. In other embodiments, the cartilage mimetic hydrogel comprises one or more materials selected from the group consisting of: poly(ethylene glycol), poly(ethylene glycol) diacrylate, poly(ethylene glycol) methacrylate, thiolated poly(ethylene glycol), acryloyl-PEG-RGD, norbornene functionalized PEG, chondroitin sulfate, thiolated chondroitin sulfate, methacrylated chondroitin sulfate, cell adhesion peptide RGD, and TGF-β3. In other embodiments, the cartilage mimetic hydrogel comprises one or more enzyme degradable peptides. In yet other embodiments, the cartilage mimetic hydrogel comprises a peptide that can be degraded by one or more matrix metalloproteinases. In yet other embodiments, the one or more matrix metalloproteinases are selected from the group consisting of MMP2 and MMP7. In yet other embodiments, the one or more enzyme degradable peptides are selected from the group consisting of GCVPLSLYSGCG (SEQ ID NO: 13), CVPLSLYSGC (SEQ ID NO: 14) and CRGDS (SEQ ID NO: 15). In other embodiments, the cartilage mimetic hydrogel further comprises at least one biological factor is selected from the group consisting of SDF-1α, CCL25, TGF-β1, TGF-β3, ranibizumab, bevacizumab, lapatinib, sunitinib, sorafenib, axitinib, and pazopanib. In yet other embodiments, the cartilage mimetic hydrogel further comprises one or more biopolymers selected from the group consisting of aggrecan, collagen, and gelatin.

In certain embodiments, the 3D printed structure is degradable once placed in the body. In other embodiments, the cartilage mimetic hydrogel is degradable once placed in the body.

In certain embodiments, the biomimetic cartilage construct further comprises one or more types of cells. In other embodiments, the construct further comprises one or more types of stem cells. In yet other embodiments, the construct further comprises one or more types of mesenchymal stem cells.

In certain embodiments, the cartilage mimetic hydrogel comprises at least one multifunctional monomer and at least one degradable cross-linker. In certain embodiments the at least one multifunctional monomer comprises one or more materials selected from the group consisting of: poly(ethylene glycol), poly(ethylene glycol) diacrylate, poly(ethylene glycol) methacrylate, thiolated poly(ethylene glycol), acryloyl-PEG-RGD, and norbornene functionalized PEG. In other embodiments, the at least one degradable cross-linker is an enzyme degradable peptide. In yet other embodiments, the enzyme degradable peptide is selected from the group consisting of GCVPLSLYSGCG (SEQ ID NO: 13), CVPLSLYSGC (SEQ ID NO: 14) and CRGDS (SEQ ID NO: 15).

In certain embodiments, the cartilage mimetic hydrogel comprises at least one biomimetic moiety selected from the group consisting of chondroitin sulfate, thiolated chondroitin sulfate, methacrylated chondroitin sulfate, and cell adhesion peptide RGD.

In certain embodiments, the at least one multifunctional monomer comprises a multifunctional polyethylene glycol. In other embodiments, the multifunctional polyethylene glycol is functionalized with at least one amine group. In other embodiments, the multifunctional polyethylene glycol is functionalized with at least one norbornene group. In yet other embodiments, the multifunctional polyethylene glycol comprises an 8-armed polyethylene glycol monomer.

In certain embodiments, the cartilage mimetic hydrogel comprises TGFβ3 covalently bound to the hydrogel matrix. In other embodiments, the TGFβ3 is thiolated.

In certain embodiments, the cartilage mimetic hydrogel comprises chondroitin sulfate. In other embodiments the chondroitin sulfate is thiolated.

In certain embodiments, the cartilage mimetic hydrogel comprises multifunctional polyethylene glycol, TGFβ3, chondroitin sulfate, CVPLSLYSGC (SEQ ID NO: 14) and CRGDS (SEQ ID NO: 15). In other embodiments, at least a portion of the TGFβ3 is covalently bound to multifunctional polyethylene glycol.

Methods

The invention provides a method of treating growth plate injuries in a subject. In certain embodiments, the method prevents the growth of bony bars in cartilage tissue at the site of growth plate injury. In other embodiments, the method treats or prevents the arrest of bone growth at the site of growth plate injury. In yet other embodiments, the method treats or prevents bone deformities at the site of growth plate injury.

In certain embodiments, the method comprises placing a construct of the invention, as described elsewhere herein, in a void created by the growth plate injury.

In certain embodiments, the method comprises first surgically removing a bony bar from the growth plate injury in the subject and then placing a construct of the invention in the resulting void. In certain embodiments, the method comprises first surgically removing damaged growth plate cartilage from the site of the growth plate injury and then placing a construct of the invention in the resulting void.

The invention also provides a method of treating cartilage injuries in a subject. In certain embodiments, the method treats injuries to articular cartilage in the subject. In other embodiments, the method prevents the development of osteoarthritis. In certain embodiments, the method comprises placing a construct of the invention, as described elsewhere herein, in a void created by the cartilage injury. In certain embodiments, the method comprises first surgically removing at least a portion of the injured cartilage in the subject and then placing a construct of the invention in the resulting void.

In certain embodiments, the subject is a mammal. In other embodiments, the subject is a human. In yet other embodiments, the subject is an infant, toddler, child, juvenile, adolescent or young adult. In yet other embodiments, the subject has active growth plates and has not undergone epiphyseal closure.

Combination and Concurrent Therapies

In one embodiment, the compounds of the invention are useful in the methods of present invention when used concurrently with at least one additional compound useful for preventing and/or treating diseases and/or disorders contemplated herein.

In one embodiment, the compounds of the invention are useful in the methods of present invention in combination with at least one additional compound useful for preventing and/or treating diseases and/or disorders contemplated herein.

These additional compounds may comprise compounds of the present invention or other compounds, such as commercially available compounds, known to treat, prevent, or reduce the symptoms of diseases and/or disorders contemplated herein. In certain embodiments, the combination of at least one compound of the invention or a salt thereof, and at least one additional compound useful for preventing and/or treating diseases and/or disorders contemplated herein, has additive, complementary or synergistic effects in the prevention and/or treatment of diseases and/or disorders contemplated herein.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the compound and the agent are physically mixed in the composition. In another embodiment, the compound and the agent are physically separated in the composition.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Preparation of 3D Printed Construct

A pre-polymer was prepared using a solution of 99 wt % poly(ethylene glycol) diacrylate (PEGDA 700) and 1wt % four-armed thiol as a monomer solution, with 0.05 wt % Trimethylbenzoyl diphenylphosphine oxide (TPO) as a photoinitiator, and 0.02M Tinuvin Carboprotect as a dark photoabsorber for the material. Sixteen single layer 3×3 mm cylinders were 3D printed at 5 different exposure times to simulate multilayer printing conditions using the pre-polymer. Eight included a thermal initiator (0.05 wt % AIBN) and were post-cured at 100° C. The two conditions (with and without post-cure) were mechanically tested using an MTS and statistically compared using a two-way ANOVA. A soft hydrogel was then prepared with a 10 wt % PEG norbornene:thiol (1:1 ratio) with 1 wt % MMP2 degradable crosslink, 2 nM cell adhesion peptide RGD, 1 wt % thiolated chondroitin sulfate and 0.05 wt % lithium phenyl-2,4,6-trimethylbenzoylphosphinate (LAP) as a photoinitiator.

Figure 1B:
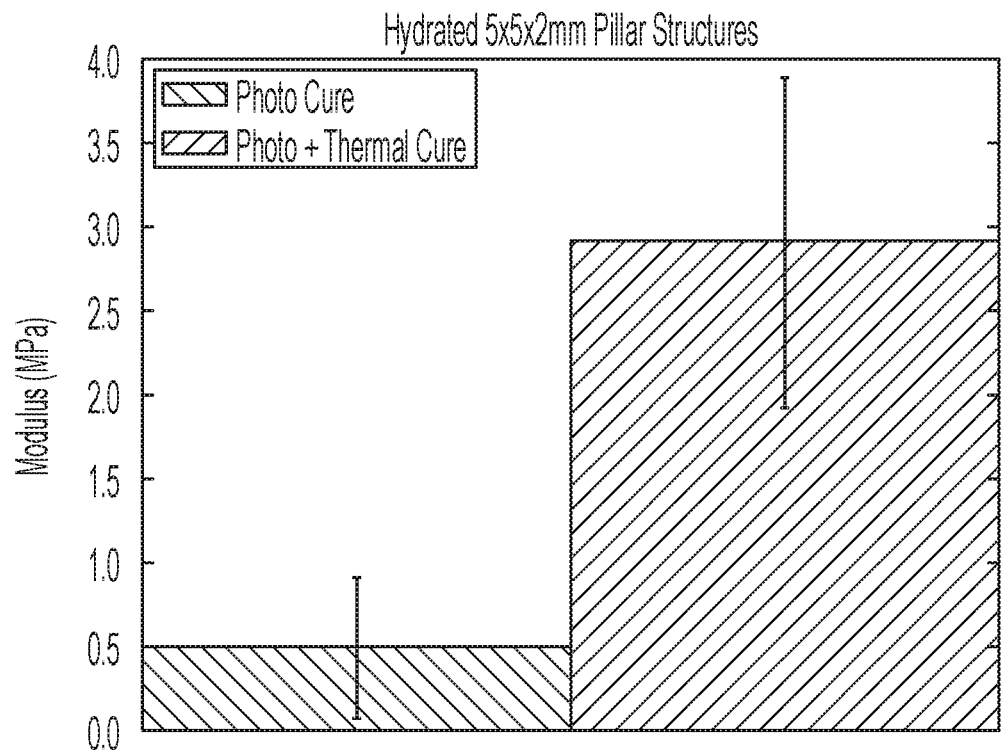
FIG. 1B is a graph showing the elastic modulus of hydrated 3D printed multilayer structures of the stiff polymer structure reported in Example 1 both with and without thermal curing.
Figure 1C:
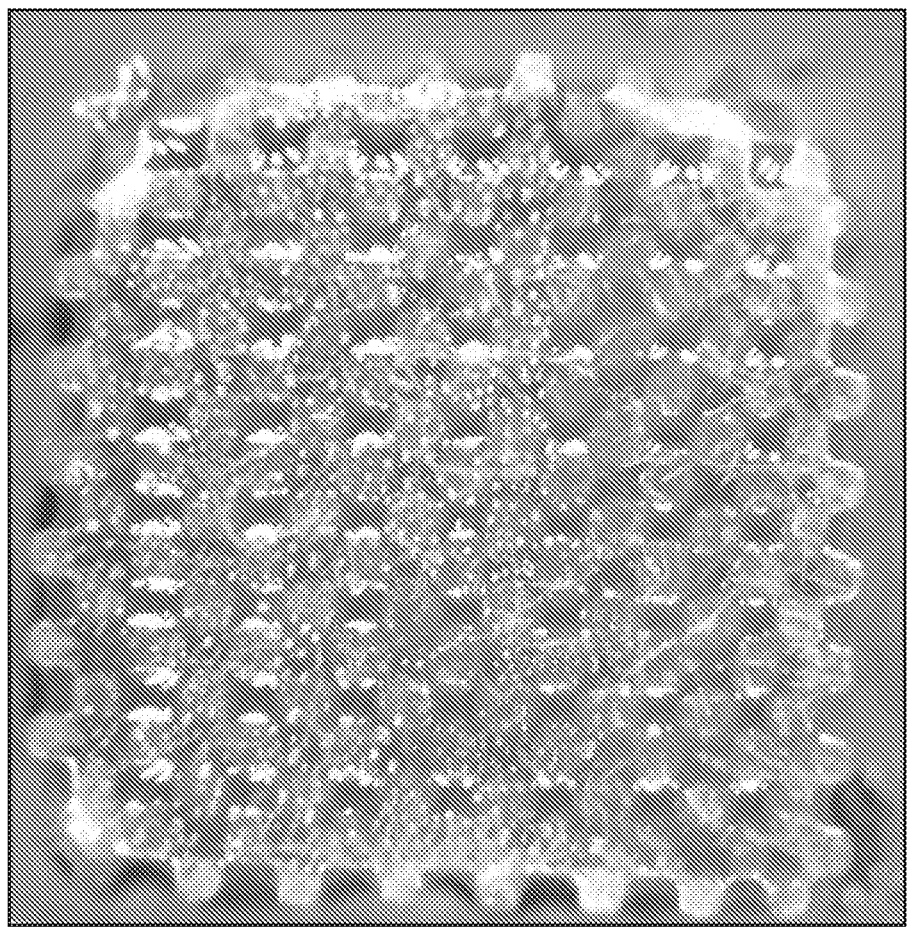
FIG. 1C is a photograph of the hydrated 3D printed structure before loading of the soft hydrogel.
Figure 1D:
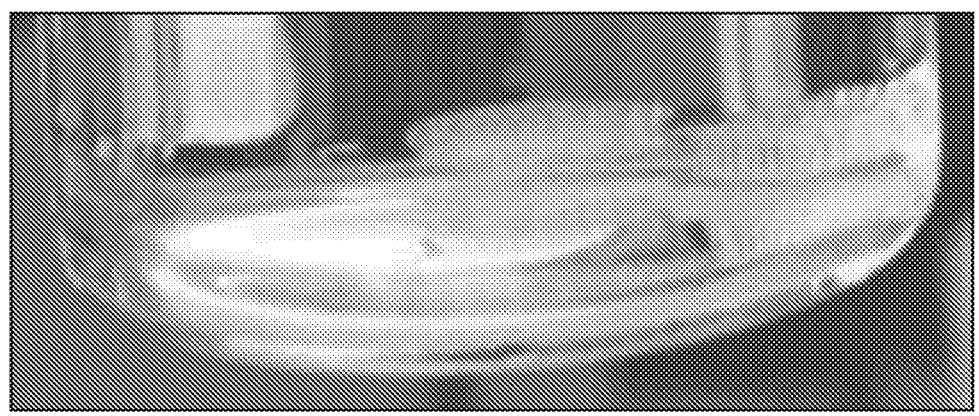
FIG. 1D is a photograph of hydrated 3D printed structures in solution.

FIG. 1A shows that the novel post-cure approach allows the uncured pre-polymer to reach full conversion and significantly increase the mechanical properties of a single 3D printed layer in exposure times less than 10 s, which is the time required for 100% conversion at an intensity of 12.5 mW/cm2 (P<0.001). No significant increase in properties is seen at the exposure times because both the photo-cured and post-cured samples have saturated and reached full conversion. FIG. 1B shows that the post-cure also affects the properties of multilayer 3D printed constructs. FIGS. 1C and 1D show hydrated 3D printed structures as described above.

Example 2: In Vivo Testing of 3D Printed Constructs

Figure 2C:
FIG. 2C is a photograph of the site of the surgically created defect after removal of the bony bar and insertion of the 3D printed construct comprising the soft cartilage biomimetic hydrogel.

The fracture sites that most commonly result in physeal injury are the wrist, the ankle and the distal femur. A New Zealand white rabbit model was used, and an injury was made to two rabbits in the physeal region of the femur (FIG. 2A) at age 6 weeks. After three weeks, the bony bar was resected and the 5×5×2 mm 3D construct infilled with the hydrogel was implanted (FIGS. 2B-2C). One week after implantation, a μCT was performed (FIG. 2D).

Figure 2E:
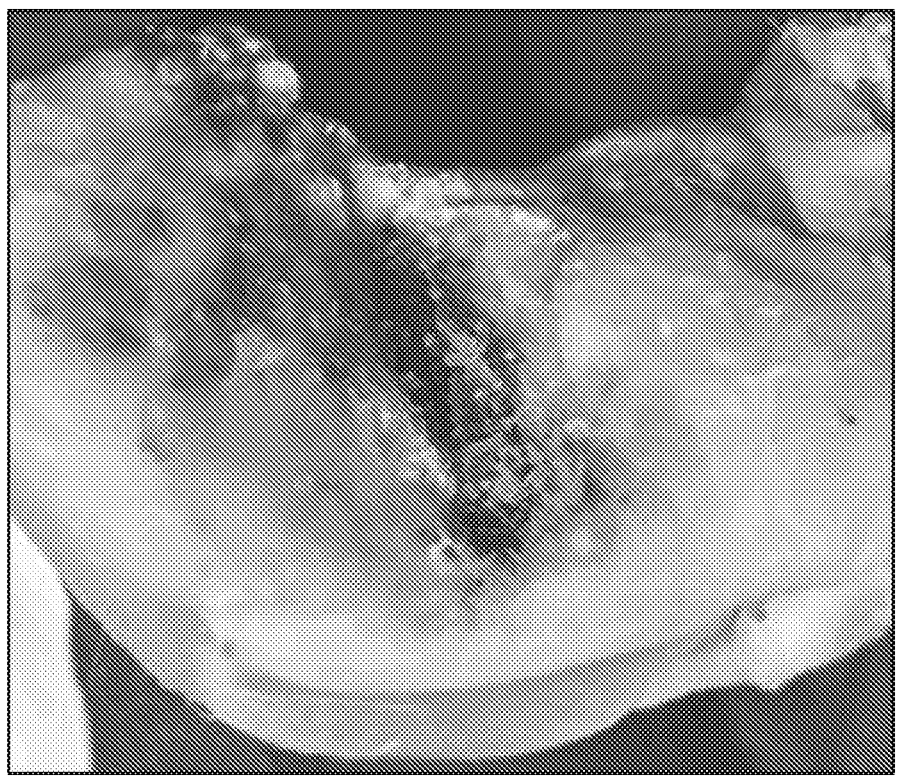
FIG. 2E is a photograph of the physeal defect 1 week after installation of the 3D printed construct.
Figure 2D:
FIG. 2D is a μCT of the physeal defect 1 week after installation of the 3D printed construct.

Rabbits were euthanized and the physeal injury site was examined (FIG. 2E).

Example 3: Cartilage Mimetic Hydrogels for MSC Growth

Materials and Methods
Macromer Synthesis

An 8-arm PEG amine (10 kDa) reactant was used to synthesize the ene' monomer, 8-arm PEG norbornene. The PEG amine was dissolved in dimethylformamide (DMF) and reacted with 8× molar excess of 5-norbornene-2-carboxylic acid in the presence of 4 molar excess n,n-diisopropylethylamaine (DIEA) and 1-[Bis(dimethylamaino0methylene)]-1H-1,2,3-triazolog[4,5-b] pyridinium 3-oxid hexafluorophosphate (HATU) overnight at room temperature under argon. The 8-arm PEG norbornene product was recovered by precipitation in ethyl ether, purified via dialysis for 2-3 days, filtered (0.2 μm), and lyophilized. Conjugation of norbornene to each arm of the 8-arm PEG was determined to be ~100% via $^1$H NMR by comparing the area under the peak for the allylic hydrogen closest to the norbornene hydrocarbon group ($\delta$=3.1-3.2 ppm) to the peak of the PEG backbone methyl groups ($\delta$=3.4-3.85 ppm).

Thiolated chondroitin sulfate (ChS-SH) was synthesized via a carbodiimide chemistry with thioacid dihydrazide. ChS (Chondroitin sulfate A, Sigma Aldrich) was dissolved in water and reacted with 2× molar excess dithiobis(propanoic dihydrazide) (DTP) and 1-ethyl-3-(3-dimethylaminopropyl) carbodiimide (EDCI) overnight at an adjusted pH of 4.75 using 1.0M HCl. To stop the reaction, the pH was raised to 7 with the addition of 1.0M NaOH. A 6.5 molar excess of dithiothreitol (DTT) was added and reacted overnight at a pH of 8.5 to reduce the thiol groups of the DTP. The thiolated chondroitin sulfate product (ChS-SH) was purified and recovered by dialysis against 0.3 mM HCl, centrifuged to remove any particulates, and the supernatant lyophilized. Conjugation of the thiol groups to the ChS was found to be ~15% (~7 thiol groups per molecule of ChS) via $^1$H NMR by comparing the area under the peaks for the methylene groups of DTP ($\delta$=2.5-2.6 and 2.6-2.8 ppm) to the area under the peak of the methyl protons of the acetyl amine side chain of the chondroitin sulfate backbone ($\delta$=1.8-2.0 ppm).

Human MSC (hMSC) Culture

Human mesenchymal stem cells (26 year old female) were purchased from Texas A&M and expanded in MSC expansion media consisting of 20% fetal bovine serum (FBS, Atlanta Biologicals), 50 U ml$^{-1}$ penicillin, 50 mg ml$^{-1}$ streptomycin, 20 mg ml$^{-1}$ gentamicin, and 5 ng ml$^{-1}$ basic fibroblast growth factor (bFGF) (Invitrogen) in low glucose Dulbecco's modified Eagle media (DMEM, Invitrogen). The hMSCs were expanded under standard cell conditions (37° C., 5% C O$_2$) to 80% confluency and passaged at 3000 cells cm$^{-2}$. Passage 3 was used.

Cell-Laden Hydrogel Preparation

Cartilage biomimetic degradable hydrogels were fabricated via photopolymerization of 9 wt % PEG-norbornene (8-arm, 10 kDa), 1wt % ChS-SH, 0.1 mM CRGDS (SEQ ID NO: 15) (Genscript), and 2.5 wt % MMP7 sensitive peptide (CRDPLE-LRADRC, SEQ ID NO: 16)) (Genscript) in the presence of 0.05 wt % photoinitiator Igracure 2959 (I2959) in phosphate buffer saline (PBS) under 352 nm light at 5 mW cm$^{-2}$ for 8 minutes. The hMSCs were encapsulated at 50 million cells ml$^{-1}$ of filter-sterilized (0.2 um filter) monomer precursor solution and photopolymerized.

Cell-laden hydrogels (5 mm diameter×2.5 mm height) were placed in 24-well tissue culture plates in 2 milliliters of chondrogenic differentiation media (1% ITS+Premix, 100 nM dexamethasone, 2.5 ng ml$^{-1}$ TGF-β3, 50 mg ml$^{-1}$ 1-ascorbic acid 2-phosphate, 50 U ml$^{-1}$ penicillin, 50 mg ml$^{-1}$ streptomycin, and 20 mg ml$^{-1}$ gentamicin in high glucose Dulbecco's modified Eagle media) which was replaced every other day. The hMSC-laden hydrogels were cultured under standard cell conditions of 37° C. with 5% CO$_2$ up to 9 weeks.

Evaluation of mRNA by qPCR

Prior to encapsulation and at prescribed culture times, hMSC-laden hydrogels (n=3/time point) were removed from culture, homogenized (TissueLyzer II, Qiagen) at 30 Hz for 10 minutes in RNA lysis buffer, and RNA was extracted using a MicroElute Total RNA Kit (Omega) per manufacturer instruction. RNA was transcribed to cDNA using a high capacity reverse transcription kit (Applied Biosystems) per manufacturer instruction. Quantitative PCR (qPCR) of chondrogenic genes, SOX9, ACAN, and COL2A1 and hypertrophic genes, RUNX2 and COL10A1. Primers for each gene are given in Table 1 along with primary efficiency. The qPCR was performed using Fast SYBR Green Master Mix (Applied Biosystems) and a 7500 Fast Real-time PCR machine (Applied Biosystems). Gene expression data was calculated from delta Ct values using true efficiencies, and relative to the house keeping gene L30. Data were also normalized to the expression of the pre-encapsulated MSCs.

TABLE 1

Primer Sequences and Efficiency for qPCR Analysis

| Gene | Forward Seq. | Reverse Seq. | Efficiency |
|---|---|---|---|
| L30 | SEQ ID NO: 1<br>5'-TTAGCGGCTG<br>CTGTTGGTT-3' | SEQ ID NO: 2<br>5'-TCCAGCGACT<br>TTTTCGTCTTC-3' | 94% |
| SOX9 | SEQ ID NO: 3<br>5'-TGACCTATCC<br>AAGCGCATTACC<br>A-3' | SEQ ID NO: 4<br>5'-ATCATCCTCC<br>ACGCTTGCTGA<br>A-3' | 95% |

TABLE 1-continued

Primer Sequences and Efficiency for qPCR Analysis

| Gene | Forward Seq. | Reverse Seq. | Efficiency |
|---|---|---|---|
| ACAN | SEQ ID NO: 5 5'-AGTATCATCG TCCCAGAATCTAG CA-3' | SEQ ID NO: 6 5'-AATGCAGAGG TGGTTTCACTC A-3' | 88% |
| COL2A1 | SEQ ID NO: 7 5'-CAACACTGCC AACGTCCAGA T-3' | SEQ ID NO: 8 5'-TCTTGCAGTG GTAGGTGATGTTC T-3' | 102% |
| RUNX2 | SEQ ID NO: 9 5'-TTGGCCTGGT GGTGTCATTA-3' | SEQ ID NO: 10 5'-GAGTCCTTCT GTGGCATGCA-3' | 98% |
| COL10A1 | SEQ ID NO: 11 5'-TTTTGCTGCT AGTATCCTTGAAC T-3' | SEQ ID NO: 12 5'-ACCTCTAGGG CCAGAAGGAC-3' | 87% |

Histological and Immunohistochemical Analysis

At prescribed culture times, hMSC-laden hydrogels (n=3/time point) were fixed in 4% paraformaldehyde, dehydrated, and paraffin embedded following a protocol using gradual concentration of ethanol to Neoclear to paraffin. Paraffin embedded hydrogels were then sectioned to 10 µm using a microtome. Sections were stained with Safranin-O/Fast Green to visualize sulfated glycosaminoglycans (sGAGs) using light microscopy (Ziess Pascal, Olympus DP70). Immunohistochemistry was performed as follows. Sections were pre-treated with appropriate enzyme treatments (hyaluronidase 200 U/ml for aggrecan and collagen II, chondroitinase ABC (10 mU) and keratinase I (4 mU) for aggrecan, pepsin (280 kU), protease (400 U) and 0.25% trypsin and EDTA for collagen X) for 1 hr at 37° C. as well as antigen retrieval (collagen I, aggrecan). Sections were treated with primary antibodies against aggrecan (1:5), collagen type II (1:50), collagen type X (1:50) and collagen type I (1:50), followed by secondary antibodies with conjugated AlexaFluor 488 or 546 probes and counterstained with DAPI for nucleus detection. A laser scanning confocal microscope (Ziess LSM 5 Pascal) was used to acquire images at 400× magnification. Semiquantitative analysis of representative confocal images (n=4 images per hydrogel, n=3 hydrogels) was performed. Sections were stained simultaneously and the gain adjustment was set and maintained for all images to minimize variations in the intensity of the stain between images. The total intensity of the positively stained protein or PEG was normalized to the number cells in each image.

Biochemical Analysis

At prescribed culture times, hMSC-laden hydrogel constructs (n=3/time point) were flash frozen in liquid nitrogen and stored at −80° C. Hydrogels were lyophilized, homogenized (TissueLyzer II, Qiagen) at 30 HZ for 10 minutes, and digested with papain for 16 hours at 60° C. DNA content in the hydrogel constructs was measured using Hoechst 33258 (n=3). Sulfated glycosaminoglycan (sGAG) content was assessed using dimethyl methylene blue (DMMB) assay (n=3).

Hydrogel Characterization

The compressive modulus of the cell-laden hydrogels was evaluated at prescribed culture times (n=3/time point). Hydrogels were compressed to 15% strain at a strain rate of 0.1 mm min$^{-1}$ to obtain stress strain curves (MTS Synergie 100, 10N). The compressive modulus was determined by the slope tangential to the linear region of the stress-strain curves from 10 to 15% strain.

Statistical Analysis

Data are represented as the mean with standard deviation. A one-way analysis of variance (ANOVA) was performed with time as the factor followed by Tukey's post-hoc analysis. P values are reported to indicate the level of significance with p<0.05 considered to be statistically significant.

Disclosure

Figure 3:
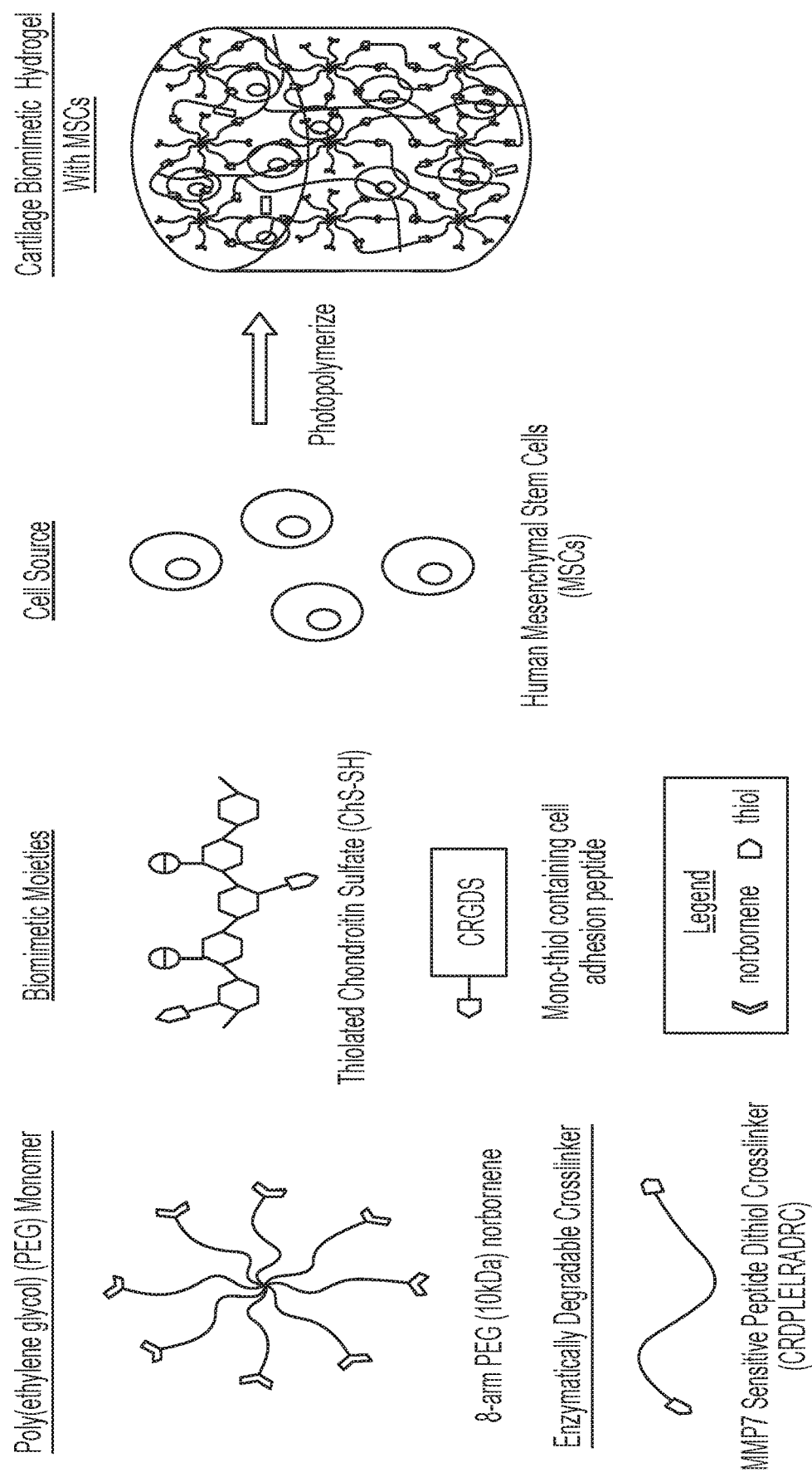
FIG. 3 is a schematic of the hydrogel precursors and the encapsulation of human mesenchymal stem cells (hMSCs) in a MMP7-sensitive cartilage mimetic hydrogel. Hydrogel precursors included 8-arm PEG functionalized with norbornene, MMP7-sensitive peptide flanked with cysteines on each end, thiolated chondroitin sulfate, and cysteine containing RGD sequence.
Figure 4B:
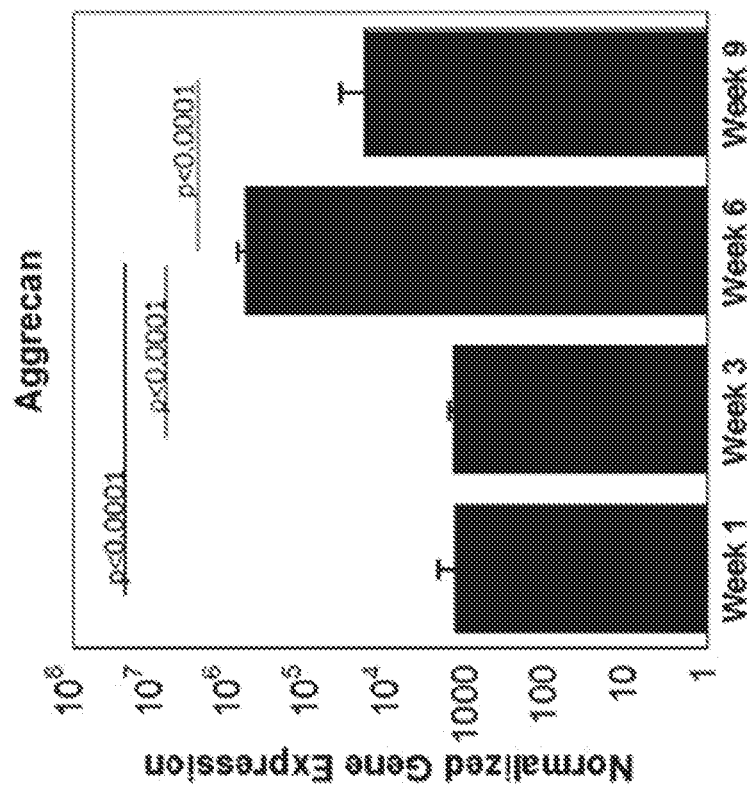
Figure 4A:
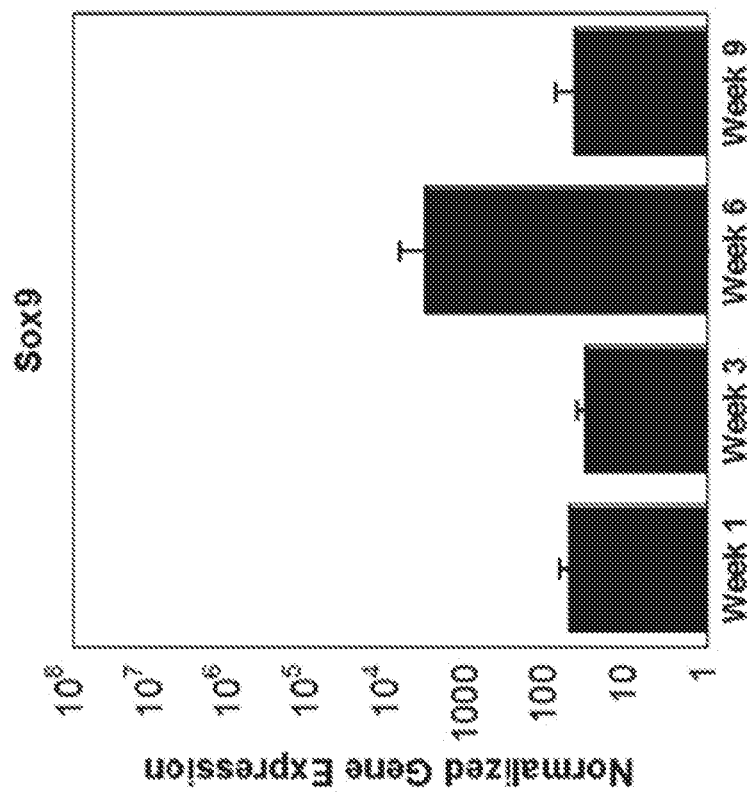
Figure 4C:
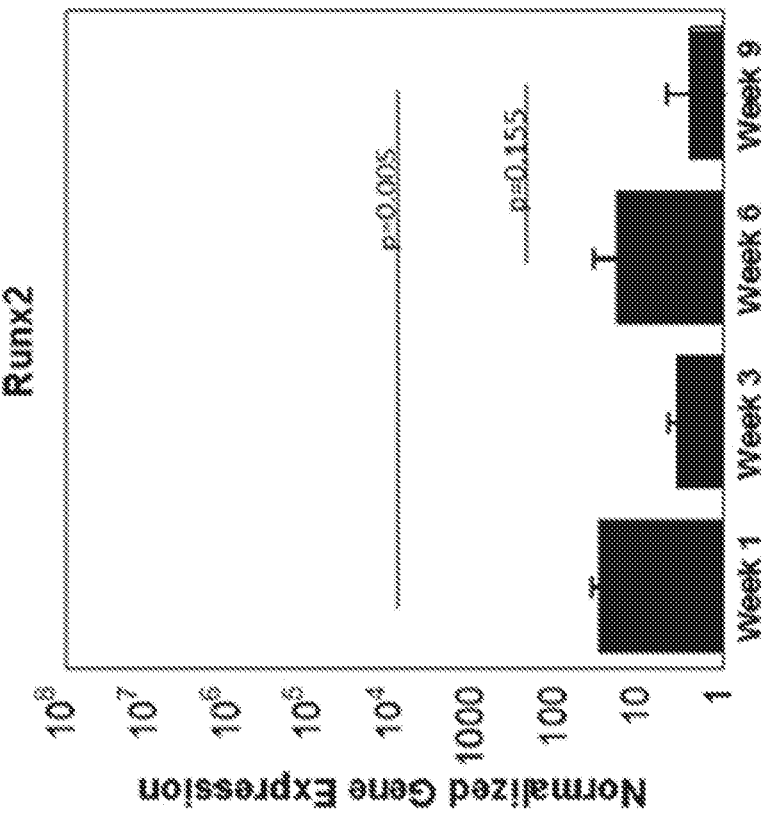
Figure 4D:
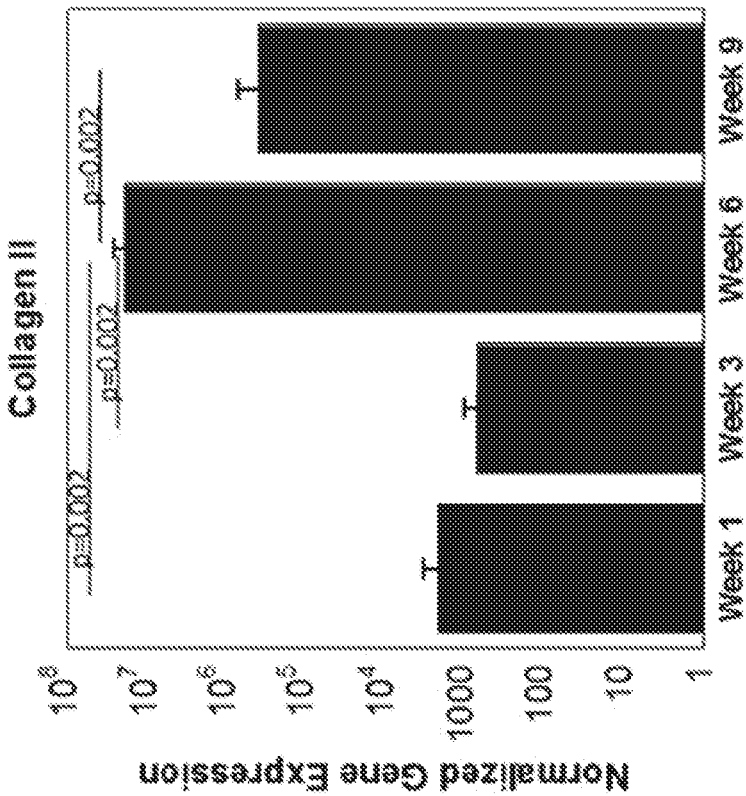
Figures 4E, 4F:
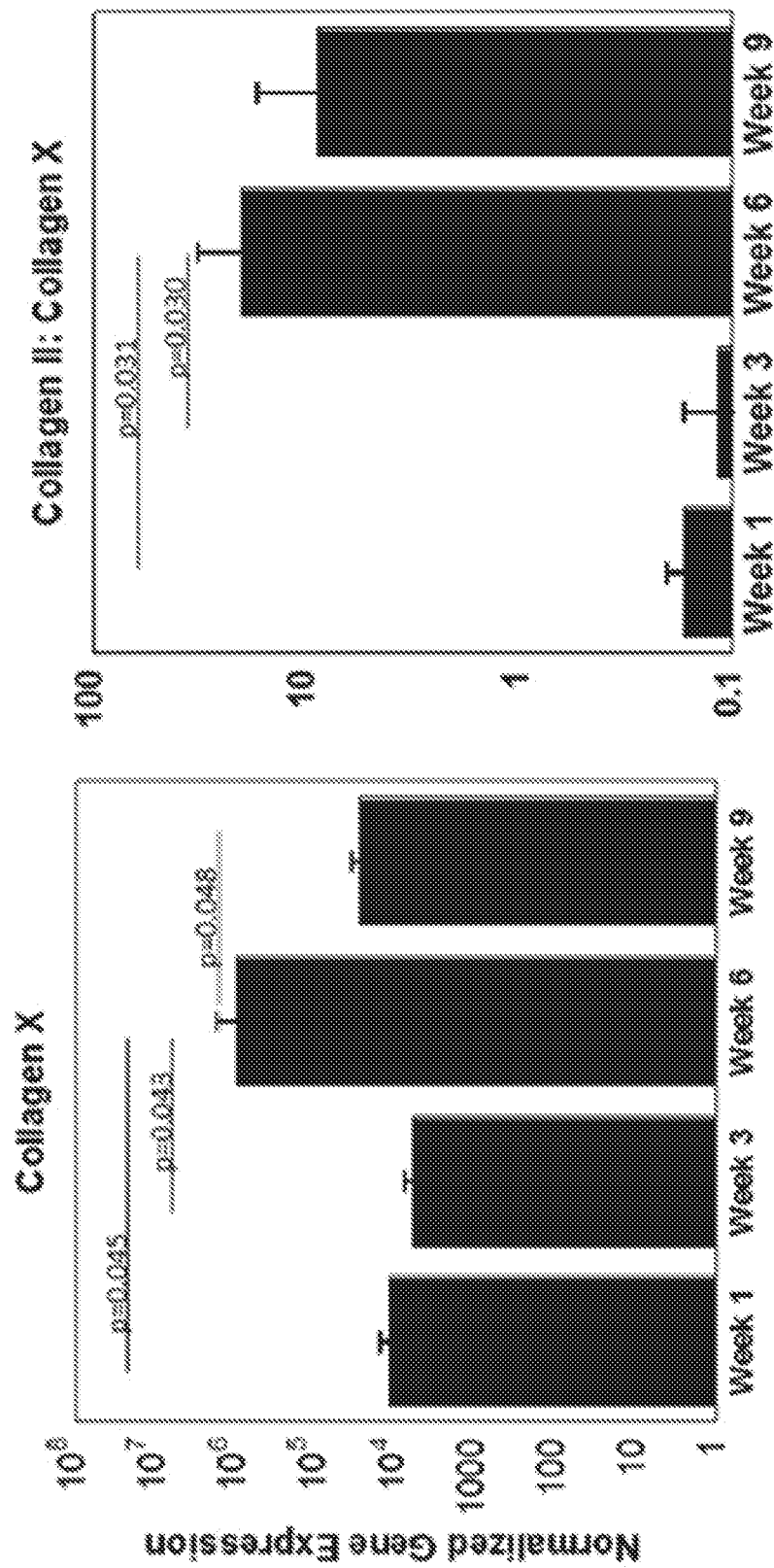

A photoclickable MMP7-sensitive cartilage mimetic PEG hydrogel was developed to encapsulate hMSCs (FIG. 3). Chondrogenesis of hMSCs was evaluated by mRNA expression over the course of nine weeks in culture (FIGS. 4A-4G). Chondrogenic genes of SOX9, a transcription factor, and ACAN and COL2A1, the main ECM molecules in cartilage, were evaluated. Time was a factor for ACAN (p<0.0001) and COL2A1 (p=0.0018), but was not for SOX9 expression. ACAN levels were maintained from week one to three and then increased (p<0.0001) by 500-fold at week six. From week six to week nine, ACAN levels decreased (p<0.0001) by 30-fold. COL2A1 levels exhibited a similar trend to that of ACAN with a 10,000-fold increase (p=0.0002) from week three to six followed by a 200-fold decrease from week six to nine.

Hypertrophic markers were evaluated by RUNX2, a transcription factor, and COL10A1. Time was a factor for RUNX2 (p=0.0045) and COL10A1 (p=0.043). Both genes were significantly up-regulated at week one when compared to the pre-encapsulated MSCs. RUNX2 levels decreased from week one to three and by week nine remained low (p=0.005) when compared to week one. COL10A1 levels increased (p=0.04) by ~100-fold at week six, but by week nine had returned to levels similar to that of week one. To further probe the phenotype of the differentiating MSCs, the ratios of COL2A1 to COL10A1 gene expression and the ratio of SOX9 to RUNX2 gene expression were evaluated. By week six, the COL2A1 to COL10A1 ratio increased (p=0.03) by ~100-fold when compared to week one or week three. SOX9 to RUNX2 ratio increased (p=0.00003) by ~100-fold from week one and increased (p=0.0004) by 10-fold from week three. By week nine, the ratio was lower (p=0.0008) than week six and not significantly different from week one.

Figure 5C:
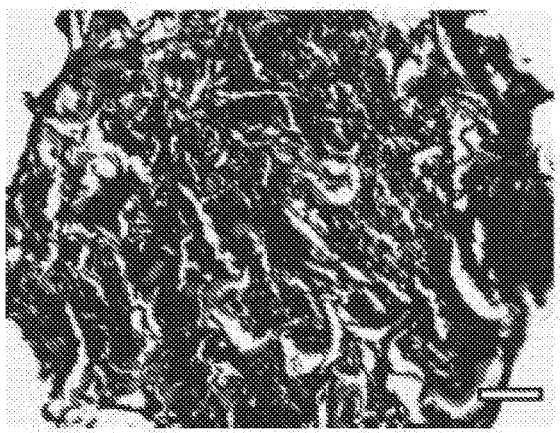
FIG. 5C is a set of representative microscopy images of histological assessment by Safranin O/Fast green, which stains sulfated glycosaminoglycans (sGAGs) red, scale bar is 100 μm.
Figure 5C:
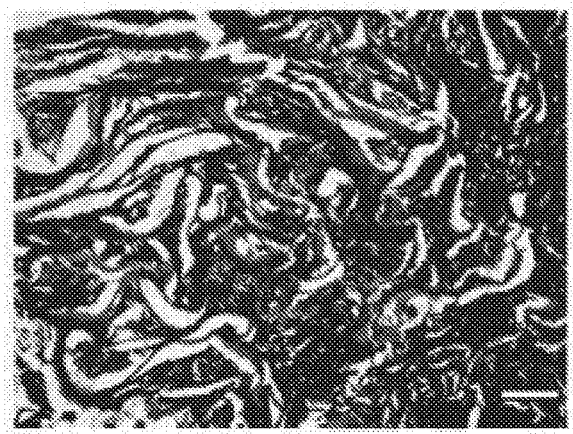
Figure 5C:
Figure 5C:
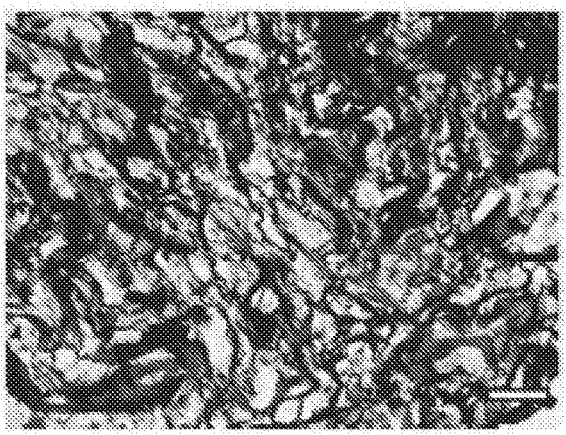

The constructs were also evaluated by their DNA content and total sulfated GAG (sGAG) content as a function of culture time (FIGS. 5A-5C). For total DNA content per construct (FIG. 5A), time was not a factor indicating that cell number remained constant in the hydrogels for the duration of the study. Time was a factor (p=0.0005) in the amount of sGAGs per construct (FIG. 5B). The sGAG content was relatively constant from week one to six, with a slight mean decrease (p=0.06) by ~20%. By week nine, the sGAGs per construct were the lowest, decreasing (p=0.005) by ~40% from week one. The spatial distribution of sGAGs in the hydrogels was also evaluated (FIG. 5C). At all time points, positive sGAG staining was present throughout the construct. However, it was not possible to differentiate between the ChS that was incorporated into the hyrogel and the newly synthesized sGAG.

Figure 6:
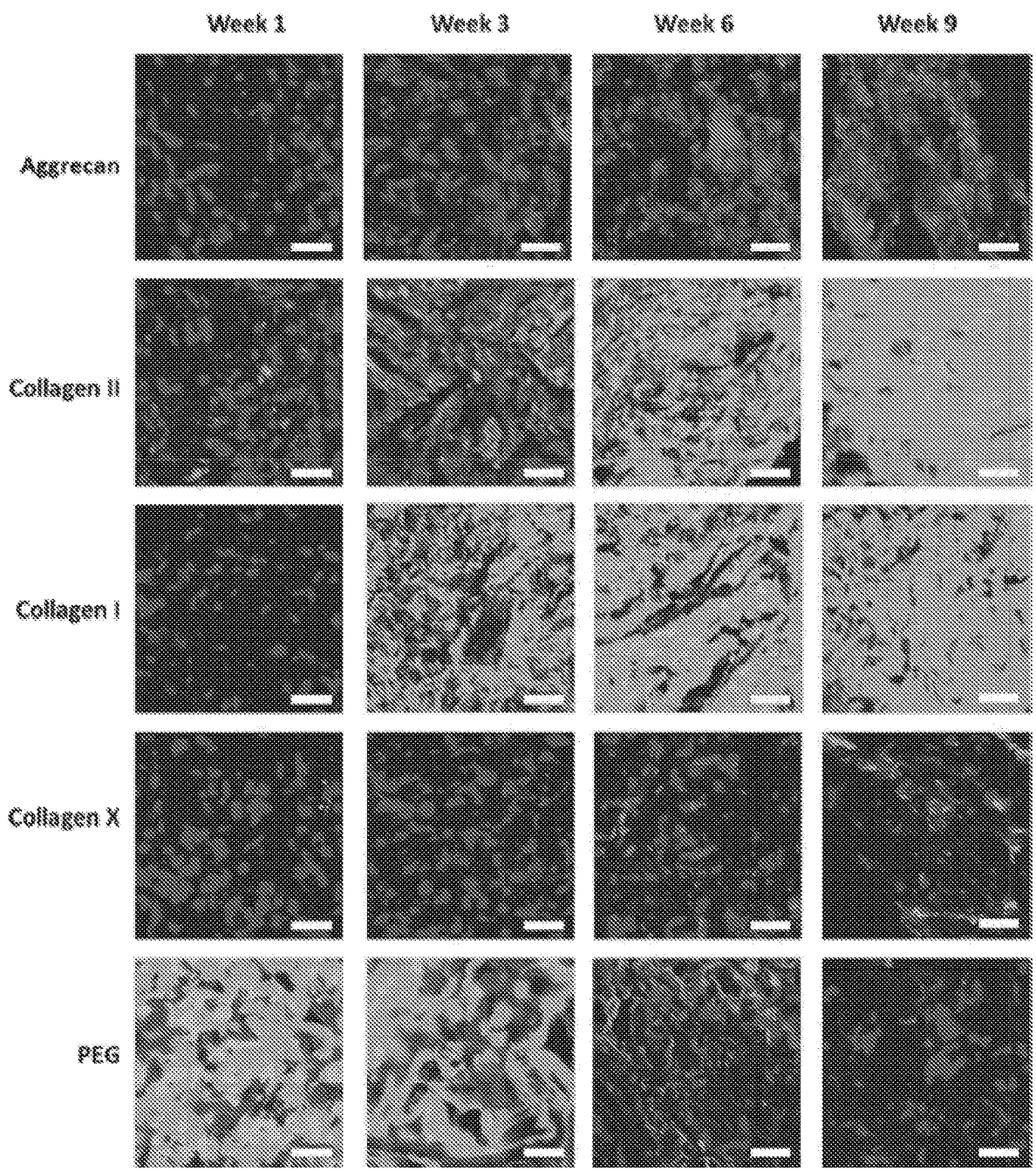
FIG. 6 is a set of representative immunohistochemical images for aggrecan (red), collagen II (green), collagen I (green), collagen X (green), and PEG (green) as a function of culture time. Images were acquired by confocal microscopy. Nuclei are stained blue. Scale bars are 20 μm.

The spatial distribution of cartilage-related proteins and the PEG polymer associated with the hydrogel were assessed by immunohistochemistry (FIG. 6). The proteins included aggrecan and collagen II for hyaline cartilage, collagen X for hypertrophic cartilage, and collagen I for fibrocartilage. There was minimal aggrecan deposition detected at week 1, but its presence appeared to increase throughout the duration of the study and by week nine was present throughout the construct. There was some detectable staining for collagen II at week one. Similar to aggrecan, collagen II presence appeared to increase with culture time and was prevalent throughout the constructs by week nine. There was minimal collagen I detected at week one, but it also appeared to increase with culture time and was present throughout the construct by week nine. There was minimal collagen X detected at weeks one and three, but its presence became apparent by weeks six and nine. Its deposition, however, appeared to be localized pericellularly and not all of the cells stained positive. The spatial presence and disappearance of PEG was also evaluated with culture time. Positive staining for PEG was evident throughout the construct at week one, but its staining diminished over time with minimal staining by week nine.

Figure 7B:
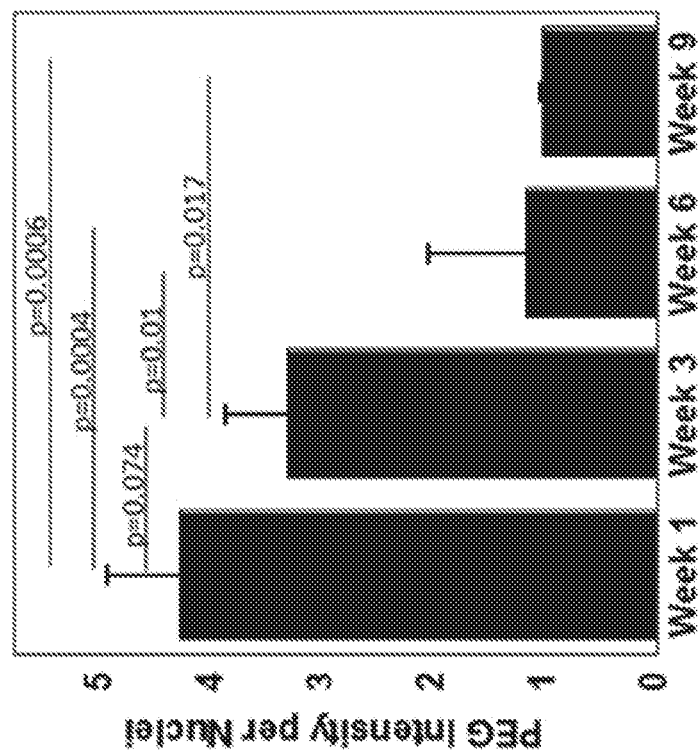
FIGS. 7A-7B are graphs showing semi-quantitative analysis of immunohistochemical images of collagen II intensity per nuclei (FIG. 7A) and PEG intensity per nuclei as a function of culture time (FIG. 7B).
Figure 7A:
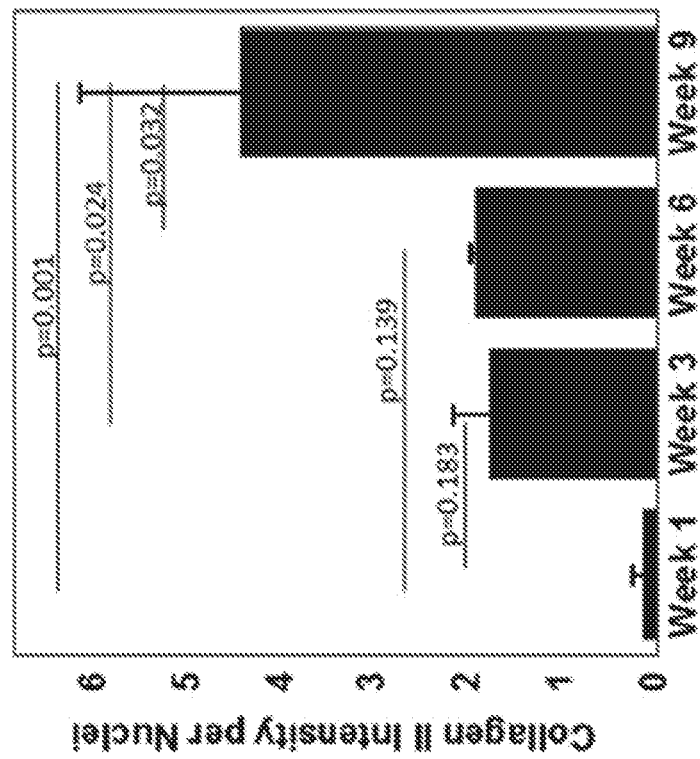
Figure 7C:
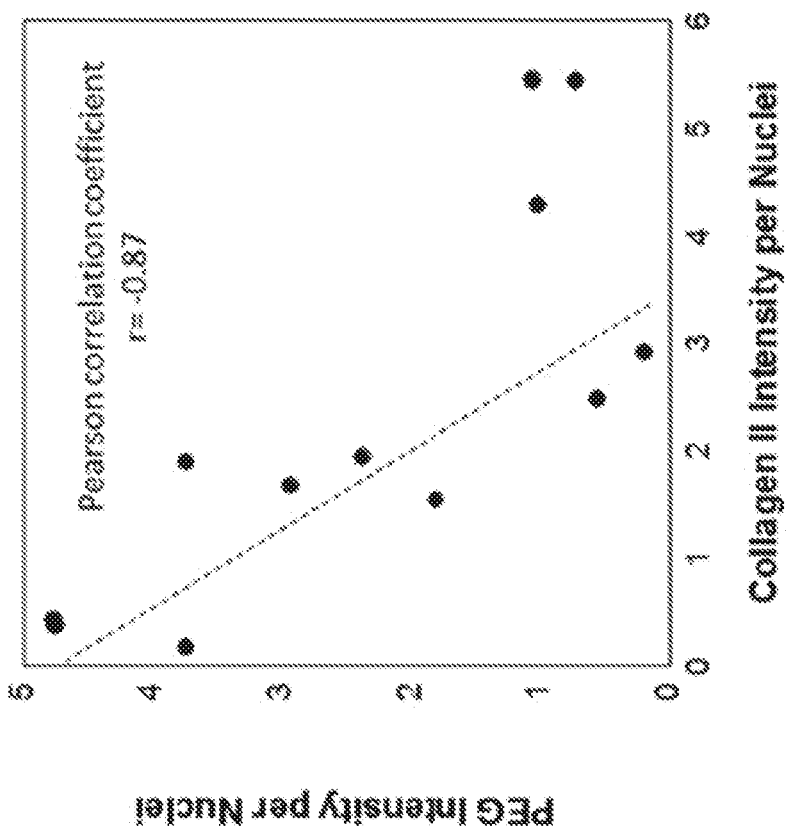
FIG. 7C is a scatter plot of PEG intensity per nuclei plotted against collagen II intensity per nuclei. A linear correlation between PEG and collagen II intensity is shown with a linear Pearson correlation coefficient of −0.87. The data points above a value of four for collagen II intensity per nuclei were not included in the linear correlation.
Figures 9A, 9B:
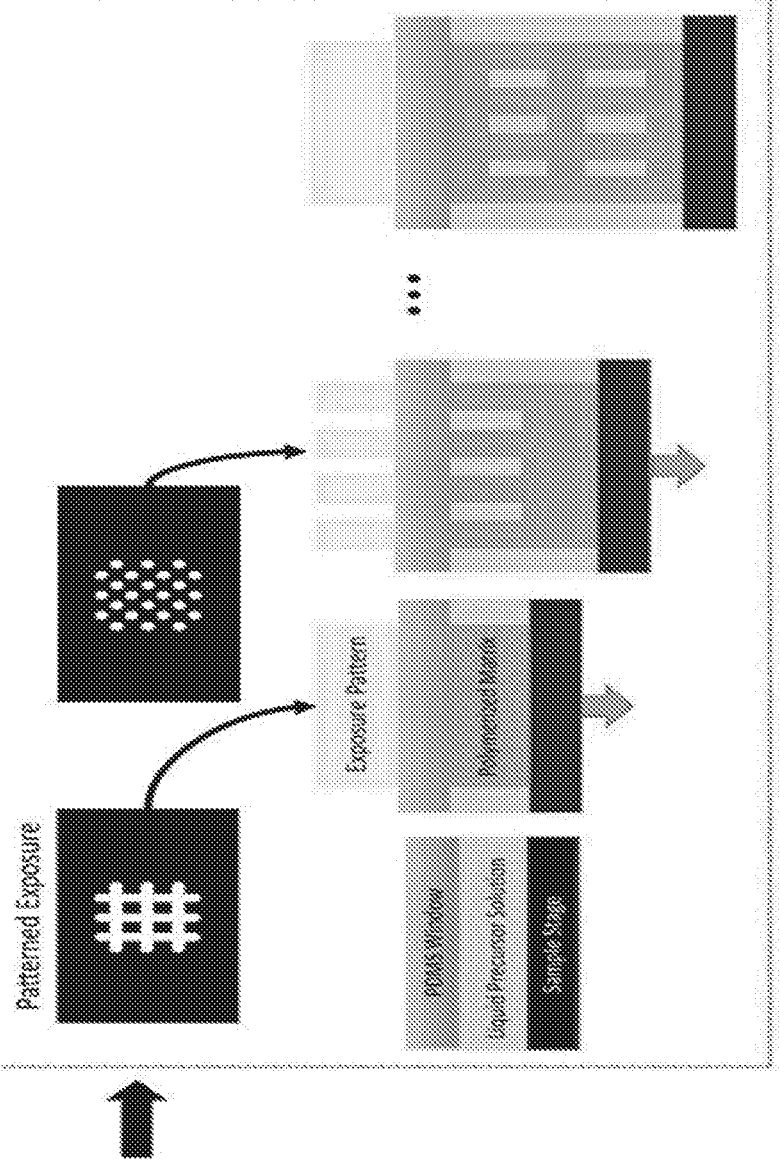
FIGS. 9A-9C are a schematic of the design, development and application of a hybrid scaffold for the potential treatment of a focal defect in articular cartilage. The hybrid scaffold consists of a 3D printed support structure and a cell-laden hydrogel (FIG. 9A). The 3D structure is printed using stereolithography through layer-by-layer digital projection printing (FIG. 9B). The overall approach to the scaffolds and methods of the invention is shown in FIG. 9C. The method of the inventiontreats a growth plate injury that has formed a bony bar by removing the bony bar and placing the 3D structure of the invention into the defect, infilling with a cartilage biomimetic hydrogel that optionally contains cells (e.g., stem cells or cartilage cells), followed by polymerization via light. Over time, the cell-laden hydrogel facilitates neotissue growth while the support structure maintains the mechanical integrity of the scaffold and ultimately both degrade leading to cartilage regeneration.
Figure 9C:
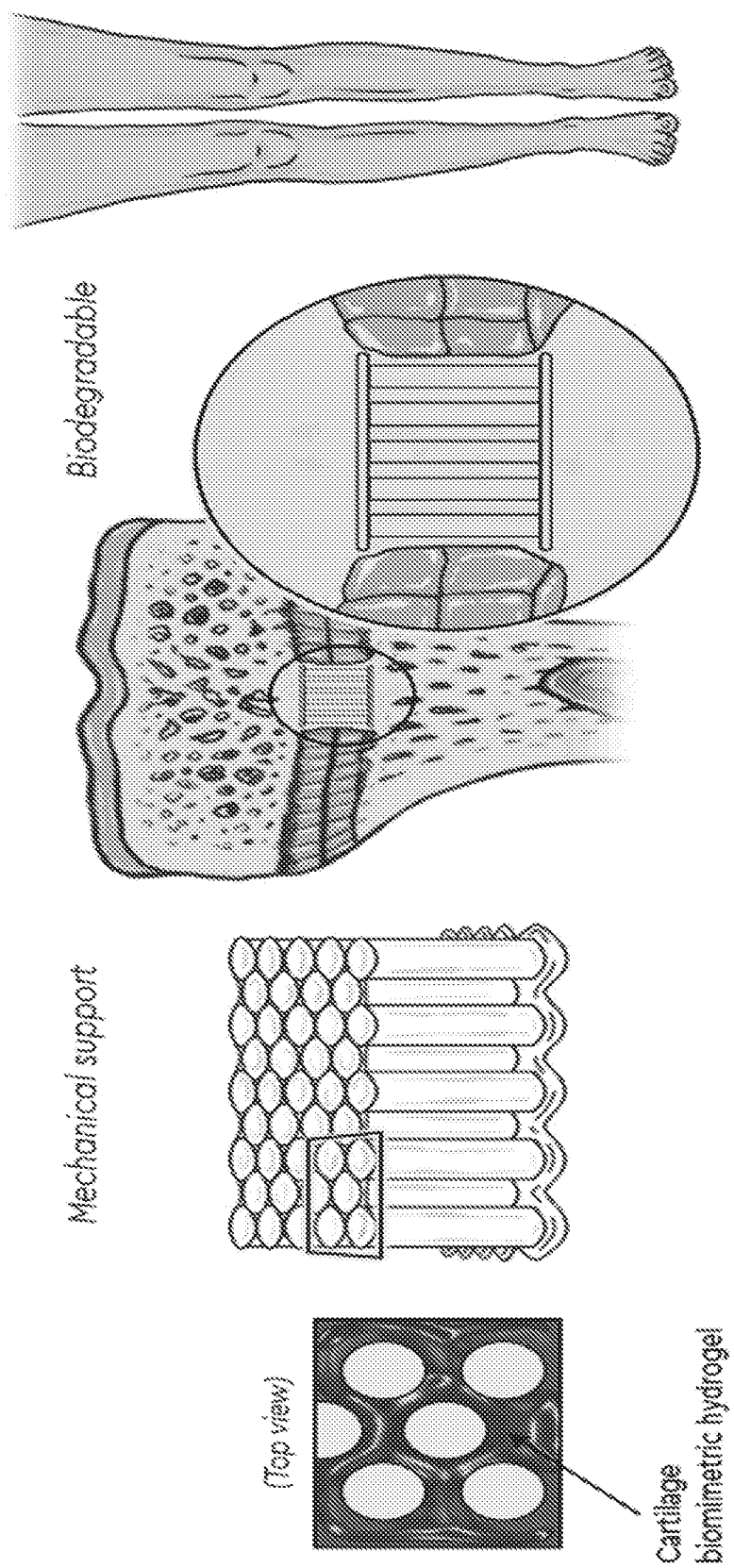

The deposition of collagen II and correspondingly PEG disappearance was quantified from the immunohistochemistry images by measuring the intensity of positively stained collagen II and the intensity of positively stained PEG, each normalized to cell nuclei (FIGS. 7A-7B). The mean intensity of collagen II increased from week one to three, although not significantly, and was maintained at week six. By week nine, collagen II intensity was the highest (p=0.001-0.032). The opposite trend was observed for PEG intensity. From weeks one to three, there was a decrease in mean PEG intensity per nuclei, although not significant, which continued to further decrease (p=0.01) by week six and remained similarly low at week nine. Additionally, PEG intensity per nuclei was plotted against collagen II intensity per nuclei (FIG. 7C). A linear relationship was observed in the data from week one to six resulting in a Pearson correlation coefficient of –0.87. Collagen intensity increased although the PEG intensity was already at its lowest, suggesting that the cells may continue to build their surrounding ECM even after the hydrogel has degraded.

Figure 8:
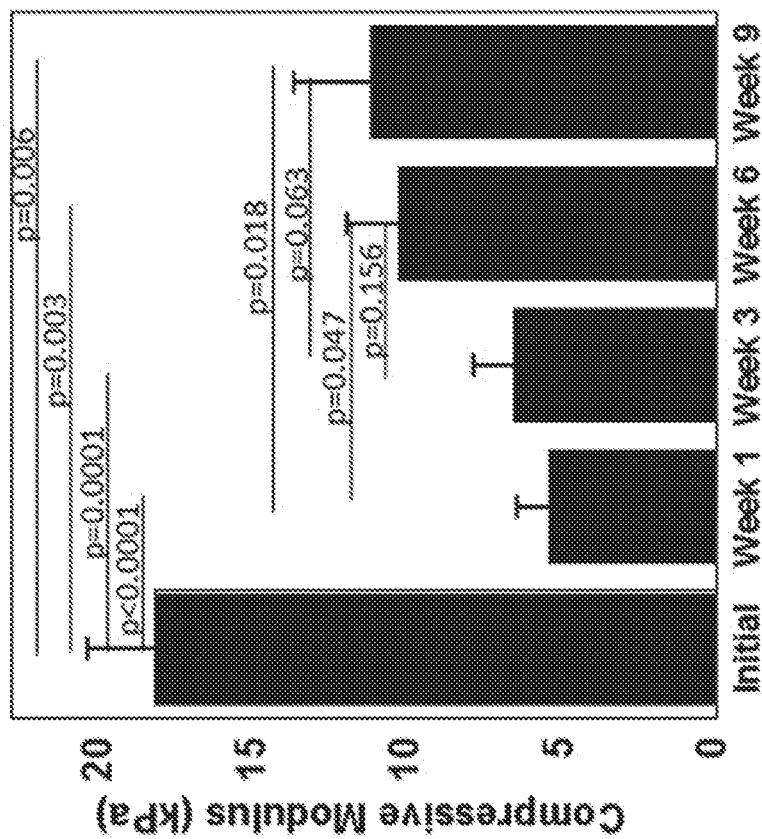
FIG. 8 is a graph showing compressive modulus measurements initially (day 1) and with culture time of the cell-laden MMP7 degradable hydrogels. Data represent mean with standard deviation as error bars (n=3).

The construct modulus under compression was measured as a function of culture time (FIG. 8). The initial modulus, which was measured after one day, was 18 (2) kPa. The modulus dropped (p<0.0001) by ~70% after one week of culture. By week six, the modulus increased (p=0.047) from week 1 to 10 (2) kPa and was maintained at week nine. Although the construct modulus increased from weeks one to nine, the final modulus was lower (p=0.006) than the initial modulus.

Example 4. 3D Printed Hybrid Scaffold for In Situ Cartilage Defect Repair

Materials and Methods
Fabrication of the 3D Support Structure by SLA-Based 3D Printing
SOLIDWORKS® was used to generate a 3D model of the support structure made of an array of 250 μm diameter pillars evenly spaced to achieve a 25% volume fraction. A 250 μm thick lattice was then added at the top, middle and bottom to provide lateral support. The dimensions of the structure were 2.06×2.06×2.00 mm (L×W×H). Autodesk's Print Studio software was used to generate 10 μm thick 2D slices from the 3D model. The 2D digital image slices were uploaded to the Autodesk Ember projection SLA printer, which is optimized for printing 10 μm thick layers. In brief, the build head is lowered into a resin bath a distance of 10 μm from the printing window, whereby a 2D digital image is projected to polymerize the resin in regions exposed to light. The process is repeated layer-by-layer until the full 3D structure is complete. A separate single layer bulk material was printed following the same polymerization conditions and used for the contact angle experiments. The commercial resin for the Autodesk Ember projection SLA printer was used. The 3D printed support structure was removed, soaked in isopropanol for 15 min to remove monomer from the unexposed regions and then sterilized in 70% ethanol overnight followed by drying under sterile conditions.

Oxygen Plasma Treatment of the 3D Printed Support Structures

Following aseptic protocols, the oxygen plasma chamber (Plasma Etch Inc., PE-25) was sterilized and stabilized by purging the chamber with oxygen plasma for 15 minutes. The sterile samples were transferred in sterile tissue culture plates, placed in the chamber, and then exposed to oxygen plasma for 1, 2 or 3 minutes. The treated materials (either the 3D printed support structure or the bulk printed material) were used immediately. The bulk printed materials were tested for hydrophilicity by photographing a water droplet on the surface.

Infilling of 3D Printed Support Structures with a PEG Hydrogel

A PEG hydrogel was formed from precursor solution of 10 (g/g) % 8-arm PEG (10 kDa) norbornene, which was synthesized from 8-arm PEG (10 kDa) amine as described in Example 3, PEG (1 kDa) dithiol at a 1:1 thiol:ene ratio, and 0.05 (g/g) % photoinitiator Igracure 2959 (12959) (BASF) in phosphate buffered saline (PBS). The hydrogel precursor solution was injected into the 3D printed support structure under vacuum and polymerized with 352 nm light at 5 mW cm$^{-2}$ for 10 minutes. The hybrid scaffold was swollen to equilibrium for 24 hours in PBS prior to characterization. To image the hydrogel in the hybrid scaffold, 0.1 (v/v) % Alexa-Fluor 546 maleimide (Thermo Fisher Scientific) was added to the precursor solution prior to polymerization. In a separate experiment, Alexa-Fluor 546 labeled microspheres (10 μm) (FluoSpheres, Molecular Probes) at 1 million spheres per ml of precursor solution were infilled and photopolymerized. In both, the swollen hybrid scaffold was imaged by confocal microscopy (Zeiss LSM 5 Pascal). 3D printed constructs were sectioned using a razor blade to image infilling in the center of the 3D printed constructs.

Willing a Cell-Laden Hydrogel in 3D Printed Constructs

Bovine chondrocytes were isolated from the femoral-patellar groove of a skeletally immature (1-3 weeks old) calf (Arapahoe Meat Co., Lafayette, Colo.) following established protocols (J. J. Roberts, S. J. Bryant, Biomaterials 2013, 34 (38), 9969-9979.). Bovine chondrocytes were suspended in the 0.22 μm sterile filtered hydrogel precursor solution at 50 million cells/ml in a 10 (g/g) % 8-arm PEG (20 kDa) norbornene, with a matrix metalloproteinase (MMP2) degradable peptide crosslinker (GCVPLSLYSGCG, SEQ ID NO: 13) at a 1:1 thiol:ene ratio. This solution was injected into the 3D printed support structures under vacuum for 30 seconds, and photopolymerized for 8 minutes at 352 nm at 5 mW cm$^{-2}$. The cell-laden hydrogels were cultured in chondrocyte medium (DMEM supplemented with 10% FBS, 0.2% Primocin, 10 mM HEPES, 0.1 M non-essential amino acids, 50 μg ml$^{-1}$ L-ascorbic acid, 4 mM 1-glutamine, 0.4 μM 1-proline) for up to 14 days (n=3). Cell-laden hydrogels were fixed in 4% paraformaldehyde for 24 hours at 4° C. and were processed for histology following standard protocols. Sections (40 μm) were pretreated with 200 U ml$^{-1}$ hyaluronidase for 1 hour at 37° C., followed by permeabilization (0.25% Triton X, 1% BSA in PBS) and blocking (1% BSA), treatment with an anti-collagen II primary antibody (1:50) (abcam ab3092) overnight at 4° C., treatment with Alexa-Fluor 488 conjugated secondary antibodies, and treatment with DAPI. Images were taken using confocal microscopy (Ziess LSM 5 Pascal).

Ex Vivo Focal Defect Treatment of Osteochondral Plugs

Osteochondral plugs (8 mm diameter, 10 mm deep) were explanted from the trochlear groove of porcine knees following aseptic protocols. Focal chondral defects (3 mm diameter, ~2 mm deep) were created in the center of the osteochondral plug. The inside of the chondral defect was dried using sterile filtered (0.2 µm syringe filter) $CO_2$ for 1 minute. The 3D printed support structure was placed into the chondral defect site, and a 0.22 µm sterile filtered hydrogel precursor solution (10 wt % 8-arm PEG norbornene (10 kDa), PEG dithiol (1 kDa) at 1:1 thiol:ene ratio, 0.05 wt % 12959) was injected into the 3D printed support structure, subjected to vacuum for 2 minutes and polymerized (352 nm, 5 mW cm$^{-2}$ for 8 minutes). A separate set of osteochondral plugs were left empty. Filled and empty plugs were cultured in chondrocyte media under either a) free swelling for 4 weeks (filled n=4, empty n=4) or b) free swelling conditions for 1 week followed by 3 weeks of unconfined dynamic compression in a custom bioreactor (filled n=4, empty n=4). In the latter, specimens were held at a constant strain of 2.5% throughout the culture, but for one hour per day were subjected to a 10% offset strain onto which a 2% peak to peak strain at 1 Hz in a sinusoidal waveform was applied. Each plug was cultured individually in a 24-well plate with 2 ml per well of chondrocyte media which was replaced every other day. After four weeks, the cartilage layer was removed from the bone layer, fixed in 10% formalin for 2 days at room temperature, transferred to 70% ethanol for storage and then were processed for histology following standard protocols. Sections (20 µm) were stained for sGAGs by Safranin O and fast green and imaged by light microscopy. Semi-quantitative analysis of histological images was performed in which measurements of the width of degenerated tissue defined by a lack of red stain were taken (n=10 measurements per image, 5 images per sample, 4 samples per condition).

Disclosure

Figure 10A:
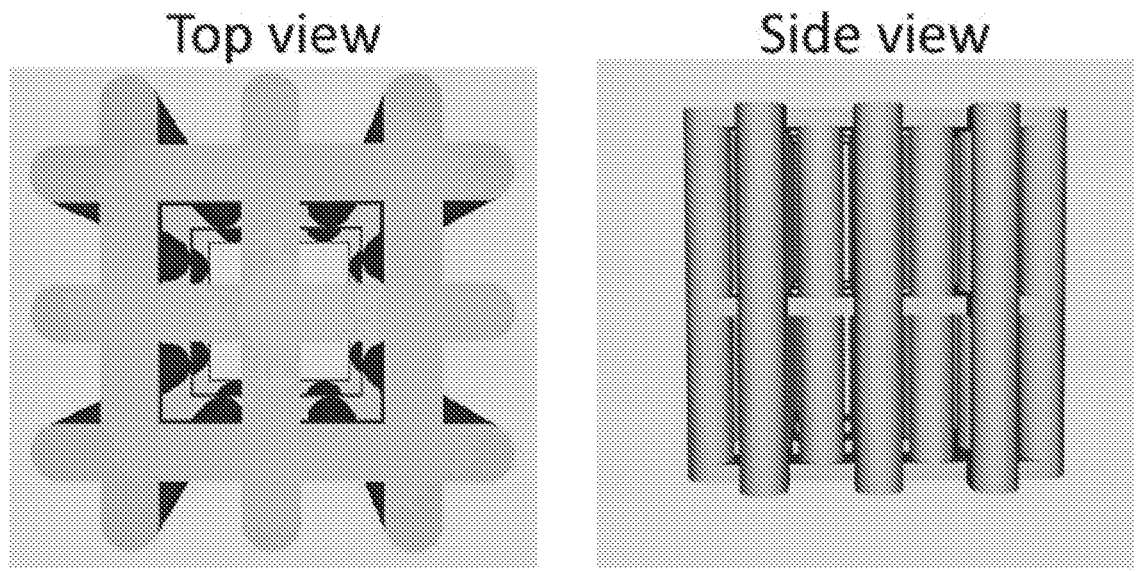
FIG. 10A is a Solidworks® 3D drawings from the top and side of the 3D support structure with 250 μm diameter pillars and top, middle, and bottom lattice structures and occupying 25% volume fraction.
Figure 10B:
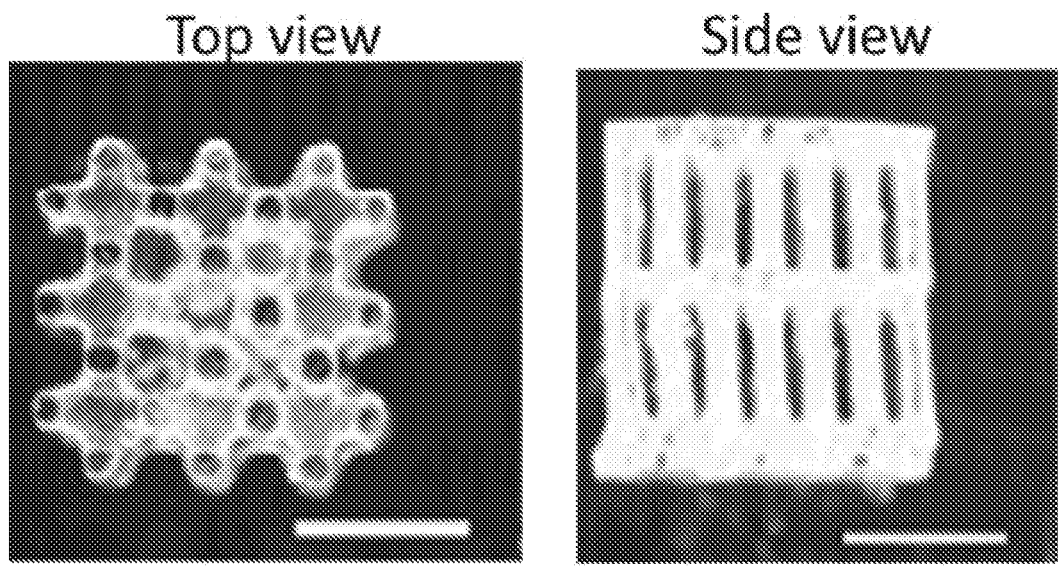
FIG. 10B is a set of photographs of the SLA 3D printed structure from the top and side (scale bar is 1 mm).

The 3D support structure was designed to fulfill several criteria. First, the structure needed to be stable over the course of the experiments to maintain structural integrity. Second, the structure needed to be infilled with the aqueous cell-compatible hydrogel precursor solution and therefore needed to be hydrophilic. And lastly, the structure needed to maintain integrity while having sufficient void space to infill with cells and allow for neotissue deposition. From these criteria, a 3D support structure was designed with an array of evenly spaced 250 µm diameter pillars which were connected together using a lattice structure at the base, middle, and top. The continuous pillar design provided structural support to resist compressive forces, while the lattice provided lateral support to resist transverse movement. The 3D support structure was also designed to occupy ~25% of the total volume, such that ~75% of the 'open' space is available for the cell-laden hydrogel. A computational rendering of the 3D support structure is shown in FIG. 10A. From this rendering, a series of 2D digital images were created and used to generate light projections for the SLA process using a commercially available Autodesk Ember Printer which prints a proprietary and stable photopolymerizable resin (Autodesk, PR-48) at a resolution reported to be 50 µm. Top view and side view images of the 3D printed structure are shown in FIG. 10B, which confirm successful printing of the 3D design.

Figures 10C, 10D:
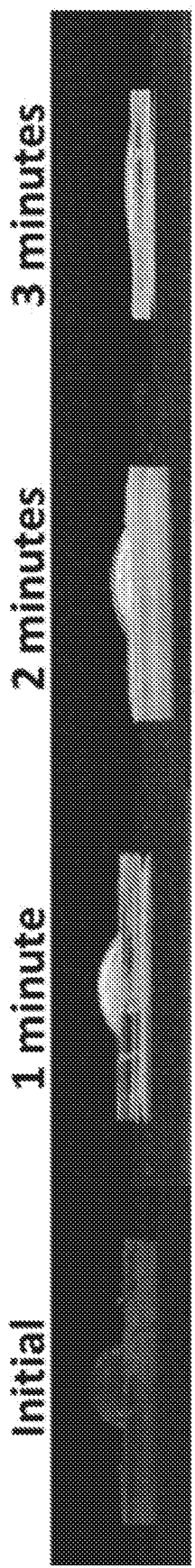
FIG. 10C is a set of photographs of water droplets on a bulk specimen made from the same material as the 3D support structure treated with oxygen plasma treatment for 0, 1, 2 and 3 minutes. A decrease in the water contact angle can be visualized with increasing oxygen plasma treatment.
FIG. 10D is a table showing contact angle measurements after oxygen plasma treatment. Data are represented as mean with standard deviation reported parenthetically for n=3.

Due to the hydrophobicity of the commercial resin that formed the printed structure, oxygen plasma treatment was investigated. A bulk printed material was made from the same resin and exposed to oxygen plasma. Increasing the time of treatment led to a decrease in the water contact angle and thus an increase in hydrophilicity (FIG. 10C). By three minutes of treatment, the water droplet nearly wet the surface resulting in a contact angel of 10 degrees indicating increased hydrophilicity. This condition was used for all subsequent experiments.

Figure 11D:
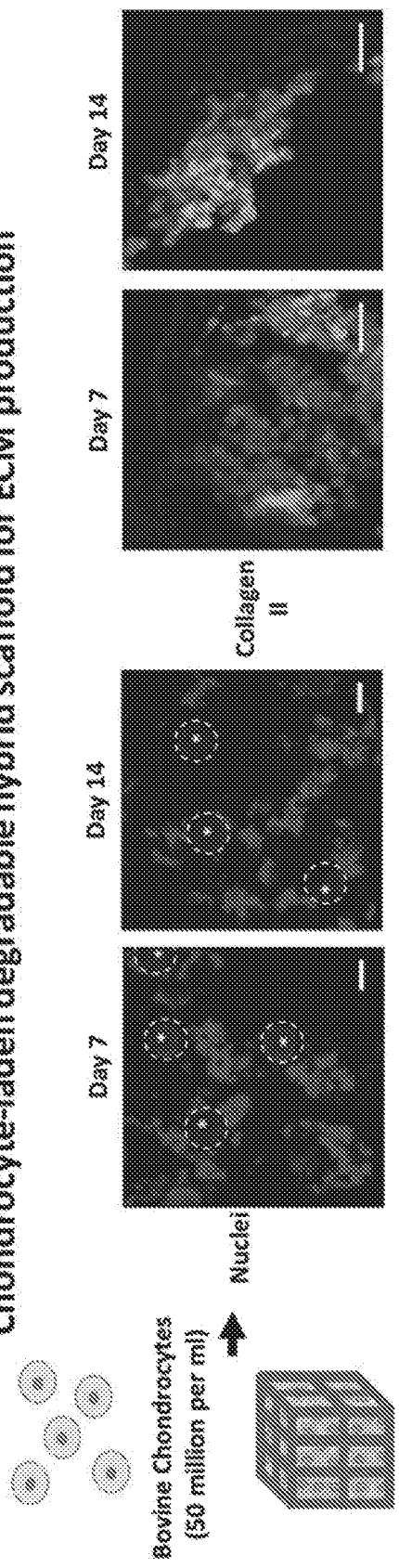
FIG. 11D is a schematic of the infilling of a chondrocyte-laden hybrid scaffold to which bovine chondrocytes were suspended in the infill solution and then subsequently photopolymerized to encapsulate them in the PEG hydrogel. The hydrogel comprised MMP2-sensitive cross-linkers. Cell nuclei (blue) shows chondrocytes are successfully infilled around the pillars (indicated by dotted line) of the hybrid scaffold at 7 and 14 days (scale bar=100 μm). High magnification images of regions of high cell density where extracellular matrix neotissue is forming as shown by staining for collagen type II (green) and cell nuclei (blue) at 7 and 14 days (scale bar=20 μm).

The ability to infill the 3D printed support structure with a hydrogel was investigated (FIGS. 11A-11D). A precursor solution of 8-arm norbornene functionalized PEG monomer (10 kDa), a PEG dithiol crosslinker (1 kDa), and fluorescently labeled PEG monothiol (1 kDa) in the presence of a maleimide-conjugated fluorophore was infilled into the 3D printed construct and photopolymerized. Successful infilling of the PEG hydrogel was demonstrated by confocal microscopy. A top view of the 3D printed structure shows the infilled hydrogel surrounding the pillars of the support structure (FIG. 11B). To demonstrate distribution of the cells in the PEG hydrogel infill, fluorescently-labeled microspheres (10 µm diameter) of similar size to cells were suspended in the hydrogel precursor solution, injected into the support structure and then exposed to light (FIG. 11C). Representative confocal microscopy images confirm a relatively uniform distribution of the microspheres within the void spaces of the support structure.

The hybrid scaffold was investigated for its ability to support chondrocytes and cartilage-specific ECM synthesis. Freshly isolated chondrocytes were suspended in a hydrogel precursor solution, injected into the support structure, exposed to light to entrap the cells within the hybrid scaffold and then cultured for two weeks (FIG. 11D). In these studies, a degradable PEG hydrogel was used where the crosslinker was a matrix metalloproteinase 2 (MMP2) sensitive peptide crosslinker. This particular crosslinker was chosen because chondrocytes have been shown to secrete MMP2 during cartilage development and remodeling. Confocal microscopy images confirm that chondrocytes were entrapped in the hydrogel regions surrounding the support structure (FIG. 11D). Chondrocyte phenotype and ECM synthesis was confirmed by staining for collagen type II, which is one of the main cartilage-specific ECM proteins found in cartilage (FIG. 11D). These findings demonstrate the feasibility of delivering chondrocytes in a degradable hydrogel into a 3D printed support structure and their ability to produce cartilage-specific ECM.

Figure 12A:
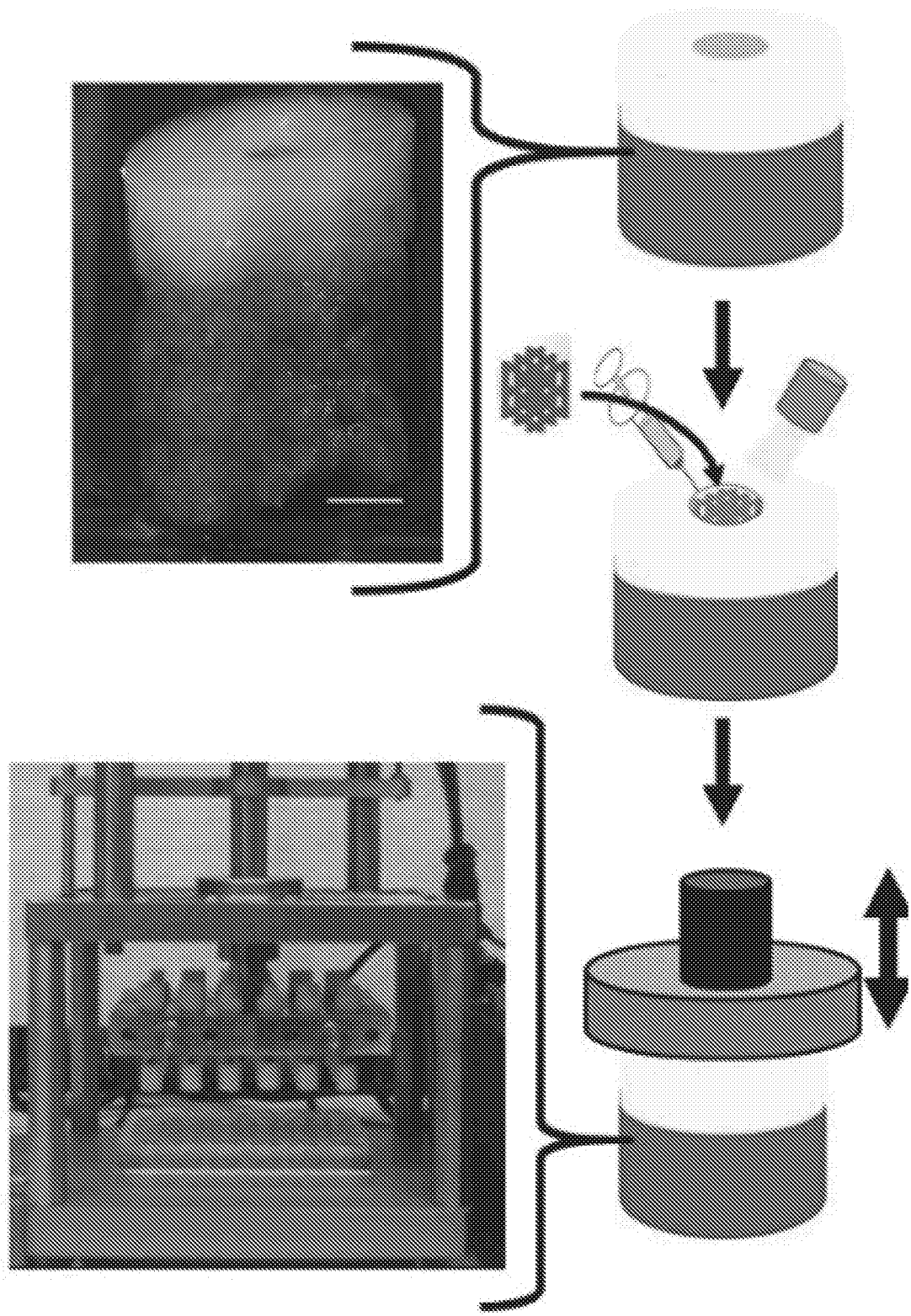
FIG. 12A is schematic showing the placement and infilling of the hybrid scaffold in a focal chondral defect of a porcine osteochondral plug (top) followed by intermittent, unconfined dynamic compression in custom bioreactors (bottom).
Figure 12B:
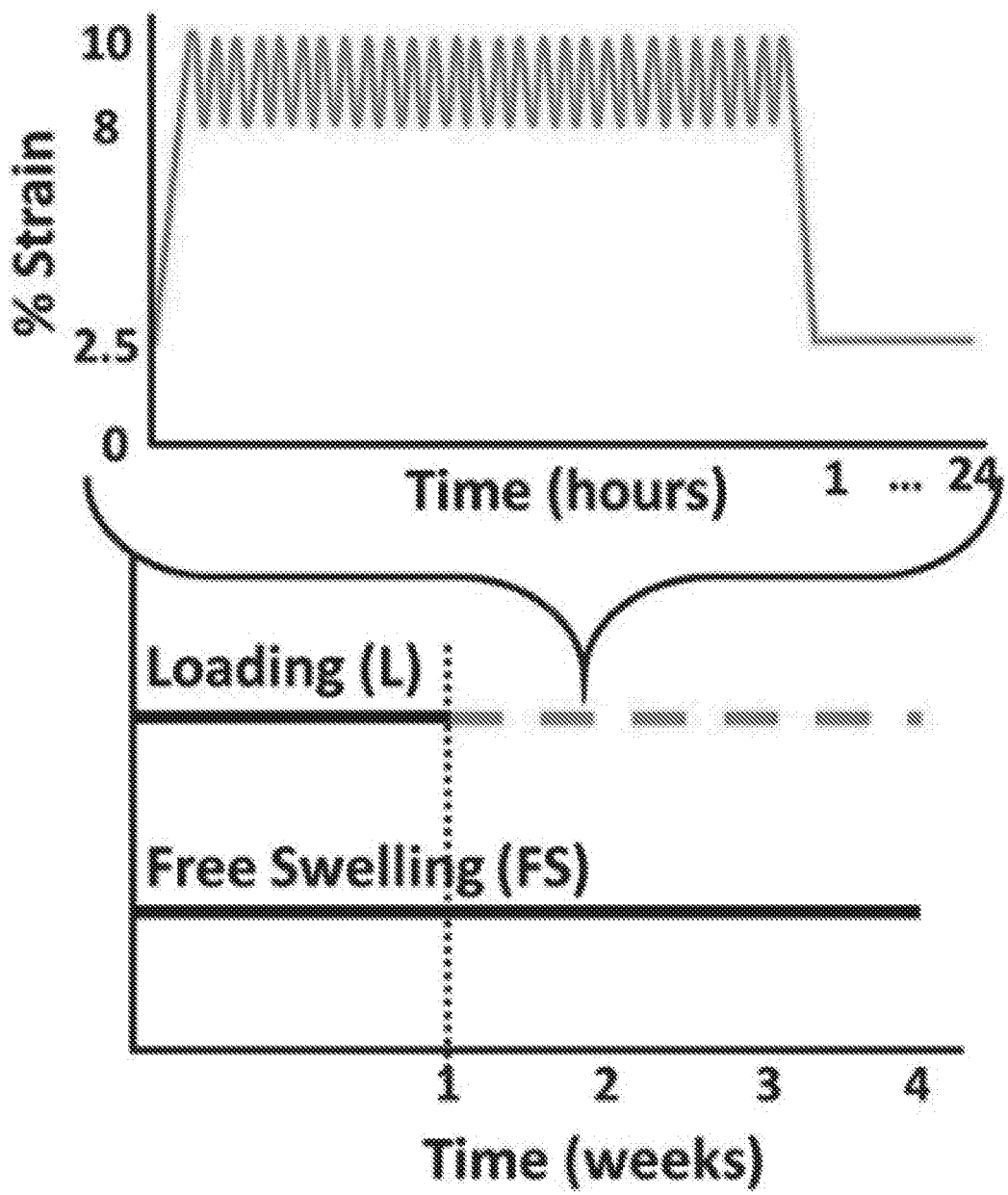
FIG. 12B is a schematic of the intermittent dynamic loading profile (green, dashed) and free swelling (black, solid). Loading was applied by applying a slow ramp from the tare strain of 2.5% to 10% compressive strain followed by dynamic loading applied in a sinusoidal waveform at a frequency of 1 Hz between 8 and 10% compressive strain for one hour. A slow ramp was applied to remove the strain to 2.5% for 23 hours.
Figure 12C:
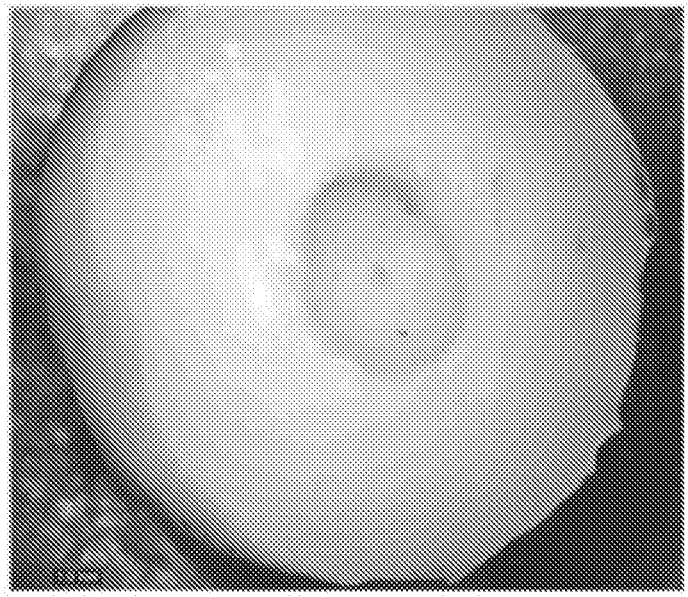
FIG. 12C is a top view of osteochondral plugs with chondral defects that were left empty (top) and filled with the hybrid scaffold (bottom). Photographs were taken immediately after filling and prior to culture.
Figure 12C:
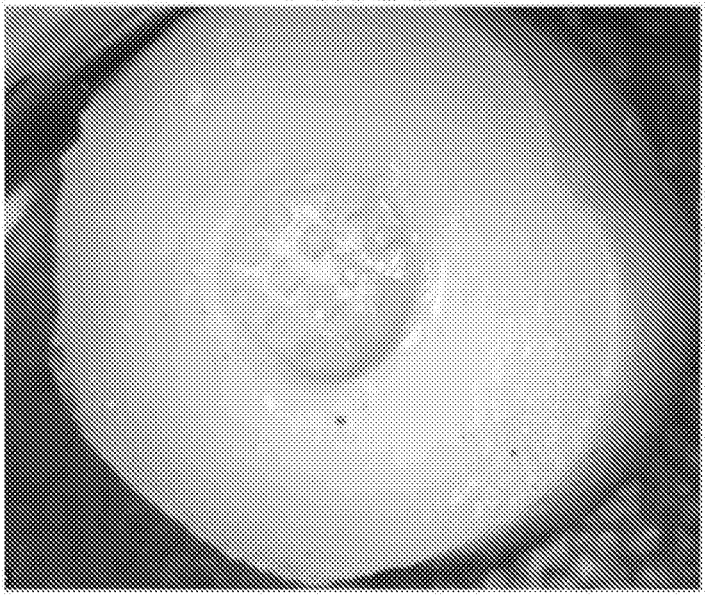

The hybrid scaffold was tested in an ex vivo focal chondral defect to demonstrate the ability to fill the defect in situ and to investigate the surrounding cartilage once filled in a dynamic mechanical environment. A chondral defect was prepared in osteochondral plugs explanted from the trochlear groove of adult porcine knees (FIG. 12A). The 3D printed support structure was treated with oxygen plasma, physically placed into the focal chondral defect, infilled with a hydrogel precursor solution, and photopolymerized in situ (FIG. 12A). To assess the ability of the in situ hybrid scaffold to protect the surrounding tissue from further damage, a stable version of the hydrogel was employed to minimize confounding factors that could arise due to changes in the scaffold properties. To emulate the in vivo environment, the osteochondral plugs (filled and empty) were subjected to physiologically relevant dynamic compressive strains for one hour per day for three weeks in custom built bioreactors (FIG. 12A). The loading profile consisted of an 10% offset strain followed by a 2% peak to peak dynamic loading strain, which has been previously shown to maintain cartilage explants ex vivo (FIG. 12B). Photographs show an unfilled defect and a defect filled with the hybrid scaffold immediately after filling (FIG. 12C). The osteochondral plugs were cultured for four weeks under free swelling or dynamic loading conditions and then removed, visualized, and then processed for histology.

Figure 12D:
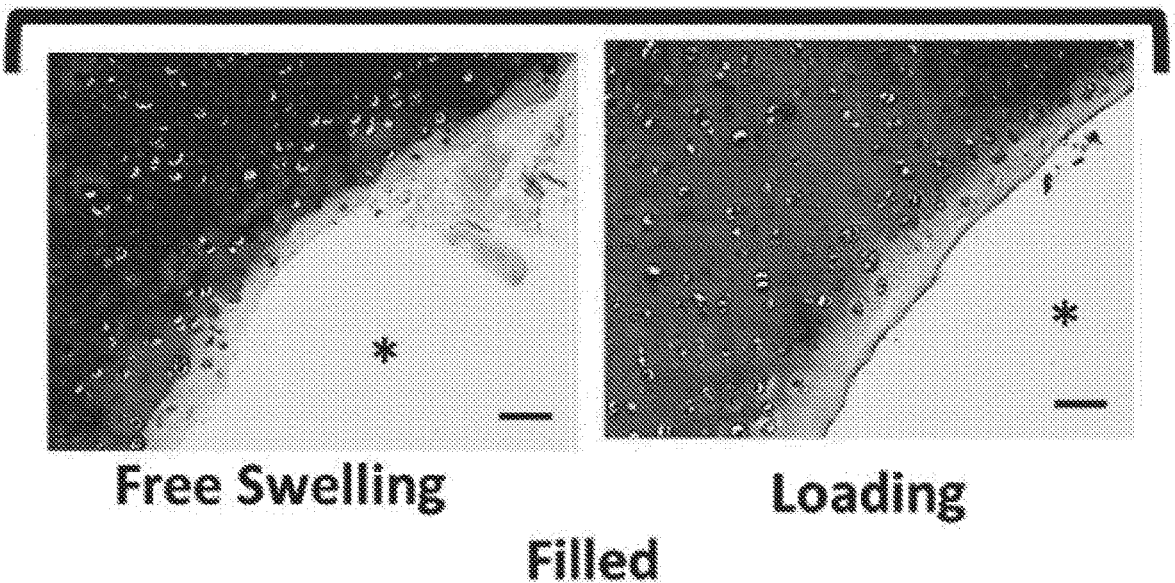
FIG. 12D is a set of representative histological images of safranin O/fast green stained sections after 4 weeks show depletion of sGAGs (red) adjacent to the defect site in empty defects (* indicates empty defect site) and retention of sGAGs in the filled defects (* indicates hybrid scaffold) (scale bar=100 μm).
Figure 12D:
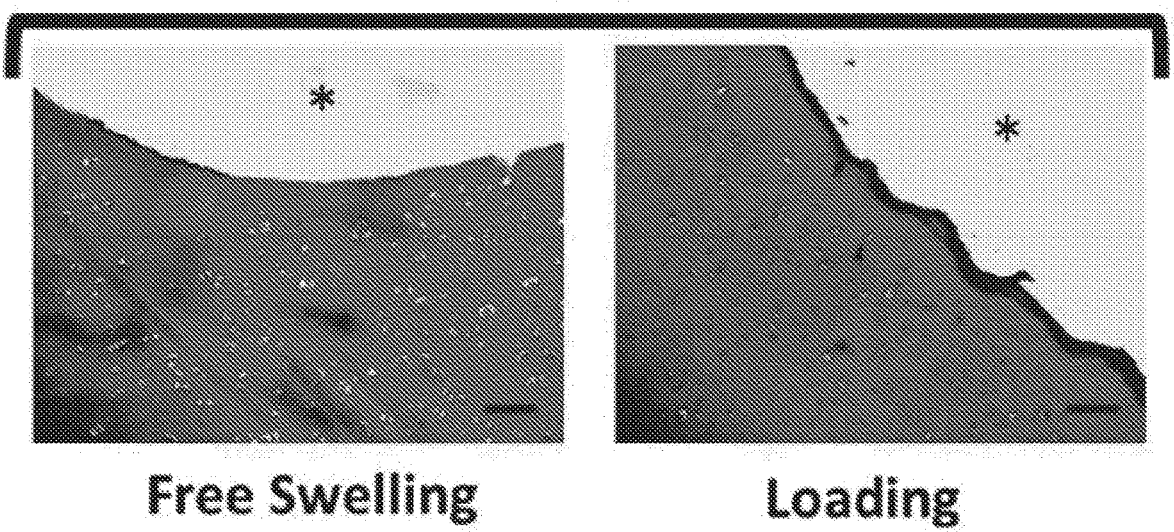
Figure 12E:
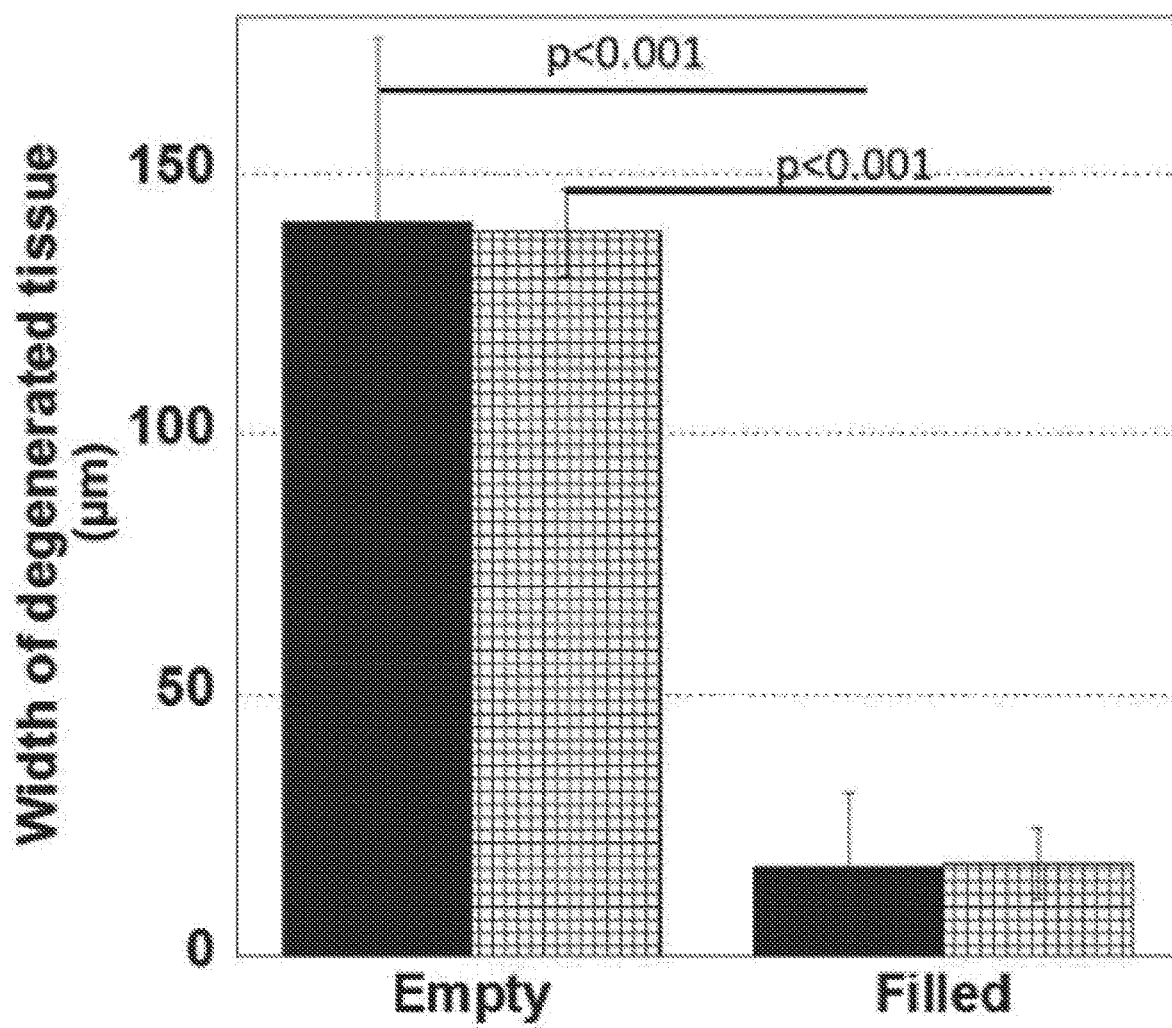
FIG. 12E is a graph showing the width of the degenerated tissue under free swelling (solid) and loading (striped) from semi-quantitative analysis of the sGAG histology (n=5, error bars=standard deviation).
Figure 13A:
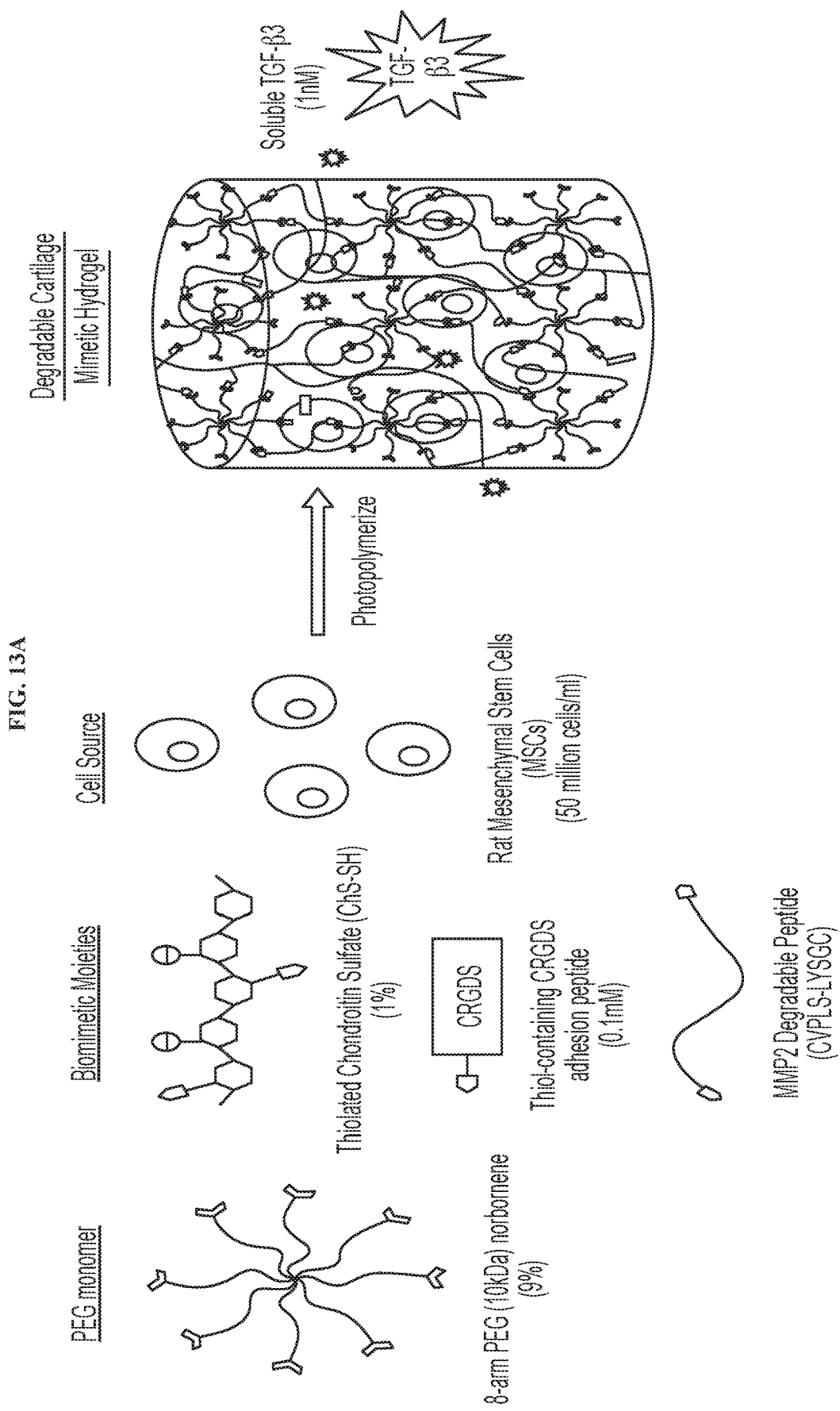
FIGS. 13A-13B are schematics of the hydrogel precursors and encapsulation of rat MSCs in a MMP degradable cartilage mimetic hydrogel via photopolymerization.
Figure 13B:
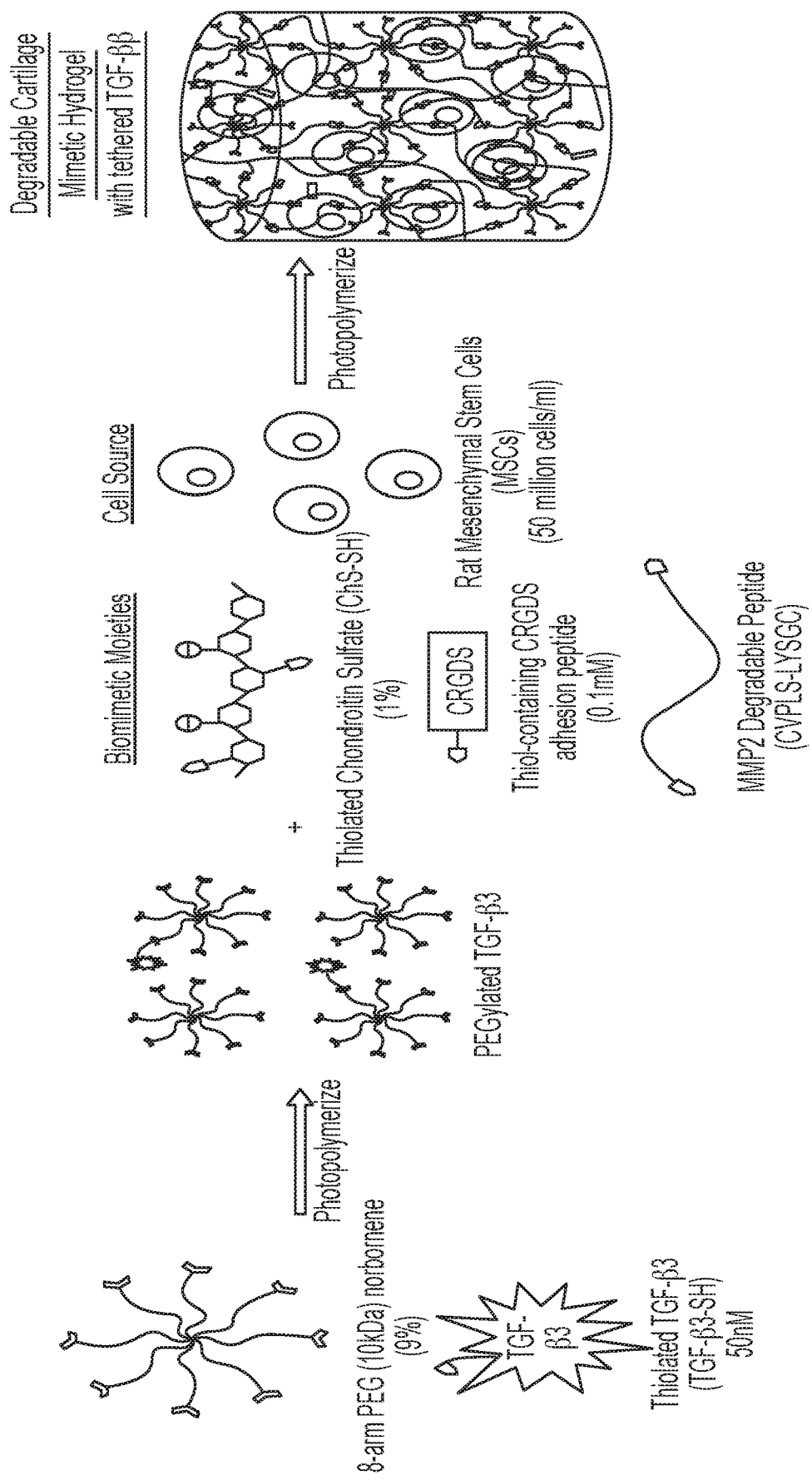

All hybrid scaffolds filling the defects visually remained in place in both loading and free swelling culture conditions after four weeks. The surrounding tissue was characterized by staining for sulfated glycosaminoglycans (sGAGs), which are the main GAGs found in aggrecan, the most abundant proteoglycan in cartilage, and have been shown to be the first ECM molecule that is lost during early stages of cartilage degeneration (FIG. 12D). Our results reveal that chondral defects left untreated displayed depletion of sGAGs in the regions adjacent to the defect (~140 μm from edge of defect), indicative of degeneration (FIG. 12E). However, chondral defects that were treated with the hybrid scaffold showed significantly higher retention of sGAGs in the regions adjacent to the defect, regardless of the loading environment (FIGS. 12D-12E). These results demonstrate that infilling of the defect with the hybrid scaffold prevents degeneration of cartilage adjacent to a defect regardless of the presence of loading. Although the exact mechanism is not known, the physical confinement that results from in situ polymerization of the infilled hydrogel may prevent tissue swelling along the defect boundary and protect the tissue.

Example 5. Cartilage Biomimetic Hydrogel in Rat Physeal Injury Model

Materials and Methods
Macromer Synthesis

PEG norbornene was synthesized as described in Example 3: 8-arm PEG amine (10 kDa) was dissolved in dimethylformamide (DMF) and reacted with 4 molar excess of 5-norbornene-2-carboxylc acid with N,N-diisopropylethylamine (DIEA) and 1-[Bis(dimethylamaino0methylene]-1H-1,2,3-triazolog[4,5-b]pyridinium 3-oxid hexafluorophosphate (HATU) overnight at room temperature under argon purge. The PEG norbornene product was precipitated in cold diethyl ether, vacuum filtered, purified by dialysis and lyophilized to recover the product. The conjugation of norbornene to each arm of the PEG amine was determined via $^1$H NMR by comparing the area under the peak for the allylic hydrogel closest to the norbornene hydrocarbon group ($\delta$=3.1-3.2 ppm) to the area under the peak for the methyl groups of the PEG backbone ($\delta$=3.4-3.85 ppm) and was found to be 100%.

ChS was thiolated as previously described: ChS (Chondroitin sulfate A, Sigma Aldrich) was fully dissolved in water and reacted with two molar excess dithiobis(propanoic dihydrazide) (DTP) and the pH was adjusted to 4.7 with the addition of 1.0M HCl. Two molar excess of 1-ethyl-3-(3-dimethylaminopropyl) carbodiimide (EDCI) was added to the ChS and DTP and reacted overnight and the pH was maintained at 4.75. The pH was raised to 7 with the addition of 1.0M NaOH to stop the reaction. The thiol groups of the DTP were reduced with the addition of 6.5 molar excess dithiothreitol (DTT) for 24 hours at a pH of 8.5. The final product, thiolated chondroitin sulfate (ChS-SH) was purified and recovered by dialysis against 0.3 mM HCl, centrifuged to remove any particulates, and the supernatant was lyophilized. Conjugation of thiol groups to ChS was found to be 15% (7 thiol groups per molecule of ChS) by $^1$H NMR by comparing the area under the peaks for the two side chain methylene groups of DTP ($\delta$=2.5-2.6 and 2.6-2.8 ppm) to the area under the peak representing the methyl protons of the acetyl amine side chain ($\delta$=1.8-2.0 ppm).

TGFβ3 (Peprotech) was thiolated using Pierce™ Traut's Reagent (2-iminothiolane) (ThermoFisher). Briefly, Traut's Reagent was reacted at a 4:1 molar ratio to TGF433 for 1 hour at room temperature. The thiolated TGFβ3 (TGF-β3-SH) was then pre-reacted with PEG norbornene to obtain a final concentration of 50 nM via photopolymerization using 0.05 wt % photoinitiator Igracure 2959 (12959) (BASF) for 30 seconds at 352 nm light at 5 mW cm$^{-2}$.

Rat MSC Isolation and Culture

Rat MSCs were isolated from male 6-week old Sprague-Dawley rats. Briefly, rats were euthanized via CO$_2$ exposure in accordance with the Guide for the Care and Use of Laboratory Animals and the American Veterinary Medical Association (AVMA) Guidelines for the Euthanasia of Animals. Both tibias and femurs were harvested, separated, and all soft tissues were removed. The ends of the bones were snipped with scissors and placed in phosphate buffered saline (PBS). Pre-warmed complete culture media containing Dulbecco's Modified Eagle Medium: Nutrient Mixture F-12 (DMEM/F2), 10% FBS, 1% penicillin/streptomycin, and 2 mM 1-glutamine was forced through the bone shaft with a syringe to extract all red marrow, and was repeated until the solution was clear. The mixture was filtered through a 70 μm filter to remove any large debris, and the filtered cell suspension was plated on a vented T175 tissue culture flask. Cells were cultured under standard cell conditions of 37° C. with 5% CO$_2$ until they were 70-90% confluent (4-7 days). The cells were then trypsinized, replated at a density of 1500 cells/cm$^2$ and expanded up to passage 3 to obtain sufficient cells for experiments.

Hydrogel Formation and MSC Encapsulation

Hydrogels were fabricated via photopolymerization from two precursor solutions. A 9% (g/g) PEG norbornene solution was used for the control, whereas for the tethered-TGF-β3 hydrogels, 9% (g/g) norbornene with the attached 50 nM TGFβ3-SH was used. The rest of the precursor solution consisted of 1% ChS-SH, 0.1 mM CRGDS (SEQ ID NO: 15) (Genscript), and 2.14% (g/g) of matrix metalloproteinase 2 (MMP2) degradable peptide flanked with cysteines CVPLS-LYSGC (EQ ID NO: 14) (Genscript). The precursor solution was filter-sterilized (0.22 μm filter) and photopolymerized with 0.05% (g/g) 12959 in PBS with 352 nm light at 5 mW cm$^{-2}$ for 8 minutes. The MSC-laden hydrogels with tethered-TGF-β3 were cultured in chondrogenic differentiation media without TGF-β3 supplement (medium (1% ITS+ Premix, 100 nM dexamethasone, 50 mg ml$^{-1}$ 1-ascorbic acid 2-phosphate, 50 U ml$^{-1}$ penicillin, 50 mg ml$^{-1}$ streptomycin, and 20 mg ml$^{-1}$ gentamicin in high glucose Dulbecco's modified Eagle media), whereas the hydrogels without the tethered TGF-β3 were cultured in the same media with the addition of 1 nM TGFβ3. MSC-laden hydrogels were cultured individually in a 24 well plate with two milliliters of chondrogenic media per well which was replaced every other day for the duration of the study. The cell-laden hydrogels were cultured under standard cell conditions of 37° C. with 5% CO$_2$.

The viability of cells encapsulated in the hydrogels was examined using Live/Dead™ (ThermoFisher). Cell-laden hydrogels were removed from culture after 9 weeks and incubated with calcien-AM (1 μM) for live cells (green) and ethidium homodimer-1 (2 μM) for dead cells (red) in warm PBS in a 24 well plate for 20 minutes. The hydrogels were then immediately imaged by confocal microscopy.

Immunohistochemistry and Histology of Cell-Laden Hydrogels

At week 3, 6, and 9 rat MSC-laden hydrogels (n=3) were removed from culture and processed for immunohistochemistry (IHC). Initially, MSC-laden hydrogels were fixed overnight at 4° C. in 4% paraformaldehyde and transferred to 30% sucrose until further processing. Hydrogels were pre-processed through a series of ethanol-based dehydration steps and embedded in paraffin and sectioned (10 µm). Sections were stained for the presence of collagen II and PEG. Sections stained for collagen II were pretreated with 2000 U ml$^{-1}$ hyaluronidase, followed by permeabilization and blocking, and treated overnight at 4° C. with anti-collagen II (Abcam ab34712, 1:50). Sections stained for PEG were pretreated with Retrievagen (BD Biosciences) for antigen retrieval and treated overnight at 4° C. with anti-PEG primary antibody at (Anti-PEG 6.3, 1:50). Sections were subsequently treated for 2 hours with goat anti-mouse IgG and goat anti-rabbit IgG labelled AlexaFluor 488 (1:100) and counterstained with DAPI. Collagen II and PEG stained images were analyzed using confocal microscopy and NIH ImageJ. The total area occupied by positive staining for collagen II and for PEG was divided by the total number of nuclei to determine a percent area per cell (n=3 hydrogels, 4 images per hydrogel). Sections were also stained for sulfated glycosaminoglycans (GAGs) by Safranin O and Fast Green and imaged at 100× by light microscopy (Ziess Pascal, Olympus DP70). Representative images are shown (n=3 hydrogels, 4 images per hydrogel).

Mechanical Testing of Cell-Laden Hydrogels

Compressive modulus was evaluated at week 1, 3, 6, and 9 (n=3) to investigate tissue production and hydrogel degradation. Using a mechanical tester (MTS Synergie 100, 10N) the tangent compressive modulus was determined by straining the hydrogels at a constant rate of 0.1 mm mid' to 15% strain and the compressive modulus was determined from the linear region of the stress vs. strain curve between 10 and 15%. Hydrogels were then flash frozen in liquid nitrogen and used for biochemical analysis.

Biochemical Analysis

At 3, 6, and 9 weeks cell-laden hydrogel constructs (n=3) were flash frozen in liquid nitrogen and stored at −80° C. until processed. Hydrogels were lyophilized, then homogenized (TissueLyzer II, Qiagen) at 30 Hz for 10 minutes, and digested by papain for 16 hours at 60° C. Cell-laden constructs were assessed for DNA content using Hoechst 33258. Collagen content was measured using the hydroxyproline assay, where hydroxyproline is assuming to make up 10% of collagen. GAGs content was assessed using the dimethyl methylene blue (DMMB) dye assay. GAG and collagen were normalized to the amount of DNA for each construct.

In Vivo Testing of Hydrogel in a Rat Physeal Injury Model

A total of 18 six-week-old Sprague-Dawley male rats were randomly allotted to six groups: Intact (no surgery); Untreated; Hydrogel (no tethered TGF-β3); Hydrogel+TGF-β3; Hydrogel+MSCs; Hydrogel+TGF-β3+MSCs. A bilateral injury was created in the distal femoral physis. Briefly, rats were anesthetized with isoflurane and laid supine on the operating table with legs extended. A 2.5-cm skin incision was made on the medial aspect of the knee. An incision was performed proximally, between the quadriceps, femoral shaft and distal femur; and continuing distally, medial to the patellar tendon until insertion. The patella was carefully luxated laterally in full knee extension and the distal femoral epiphysis and trochlea were exposed. Using a drill with a 2 mm burr oriented perpendicular to the trochlear groove, a central 2 mm thick×5 mm deep injury was created through the articular surface and into the distal femoral physis. The defect was irrigated with sterile saline solution and either left untreated or treated with hydrogel (20 µl/defect) alone or in combination with MSCs (1×10$^6$ cells) and/or TGF-β3 (50 nM). For the groups receiving hydrogel, the lights in the operating room were turned off in order to avoid premature photo-polymerization and a red light was used to allow visualization of the defect and delivery of the polymer. Photo-polymerization was performed in situ using a 405-nm blue visible light for approximately 40 seconds. The patella was then reduced, and the wound closed. After surgery, the rats were allowed full-weight bearing and kept in cages with food and water ad libitum.

Micro-CT Analysis

After 28 days, all rats were euthanized via $CO_2$ exposure in accordance with the Guide for the Care and Use of Laboratory Animals and the AVMA Guidelines for the Euthanasia of Animals. The femurs were harvested and repair tissue evaluated by Micro-Computed Tomography (Micro-CT) using a Scanco VivaCT 80 (Scanco Medical, Bassersdorf, Switzerland). The femoral length was measured. To quantify bony bar formation within the injury site, the physis area was scanned at 70 kVp and 114 µA, with 300 ms integration time, and voxel size of 15.6 mm. DICOM files were created, and analyzed in ImageJ with the BoneJ plugin (Doube, M. et al. *Bone* 47, 1076-1079, 2010.). The volume of bony repair tissue within the injured physis was measured by isolating a 2 mm diameter region of interest within the physis encompassing the region that contained the original defect. The bone volume (BV) divided by the total volume (TV) of the defined area was termed the bone volume fraction (BVF; BV/TV).

Histological Assessment of Repair Tissue

Following micro-CT, samples were fixed in 10% formalin for 48 h, decalcified in 14% ethylenediaminetetraacetic acid (EDTA) at pH 7.2, dehydrated by increasing concentrations of ethanol and embedded in paraffin blocks. Sagittal 5 µm thick sections were mounted onto slides. Standard Alcian Blue-Hematoxylin (ABH) was performed to assess repair tissue. For Collagen II and X immuhistochemistry, sections were pretreated with 770 U ml$^1$ hyaluronidase in 100 mM Na Acetate at pH 5.0 for lhr at 37° C., followed by permeabilization and blocking. They were incubated overnight at 4° C. with anti-collagen II (Iowa hybridoma bank, 1:100), and anti-collagen X (Abcam ab49945, 1:1000). Negative controls were prepared by omitting the primary antibody. Sections were subsequently and respectively treated for 1 hr with goat anti-mouse-HRP (Jackson 115-035-166, 1:500) and goat anti-mouse-HRP (Abcam ab98679, 1:1000); and counterstained with DAB. Images were taken using a Nikon Eclipse 80i microscope (Tokyo, Japan).

Statistical Analysis

Data are presented as mean with standard deviation. A one-way analysis of variance (ANOVA) with post-hoc Tukey was used for multiple group comparisons. P-values less than 0.05 were considered significant. Statistical evaluations were performed with Prism 8 (GraphPad) software.

Results

In Vitro

Figure 14A:
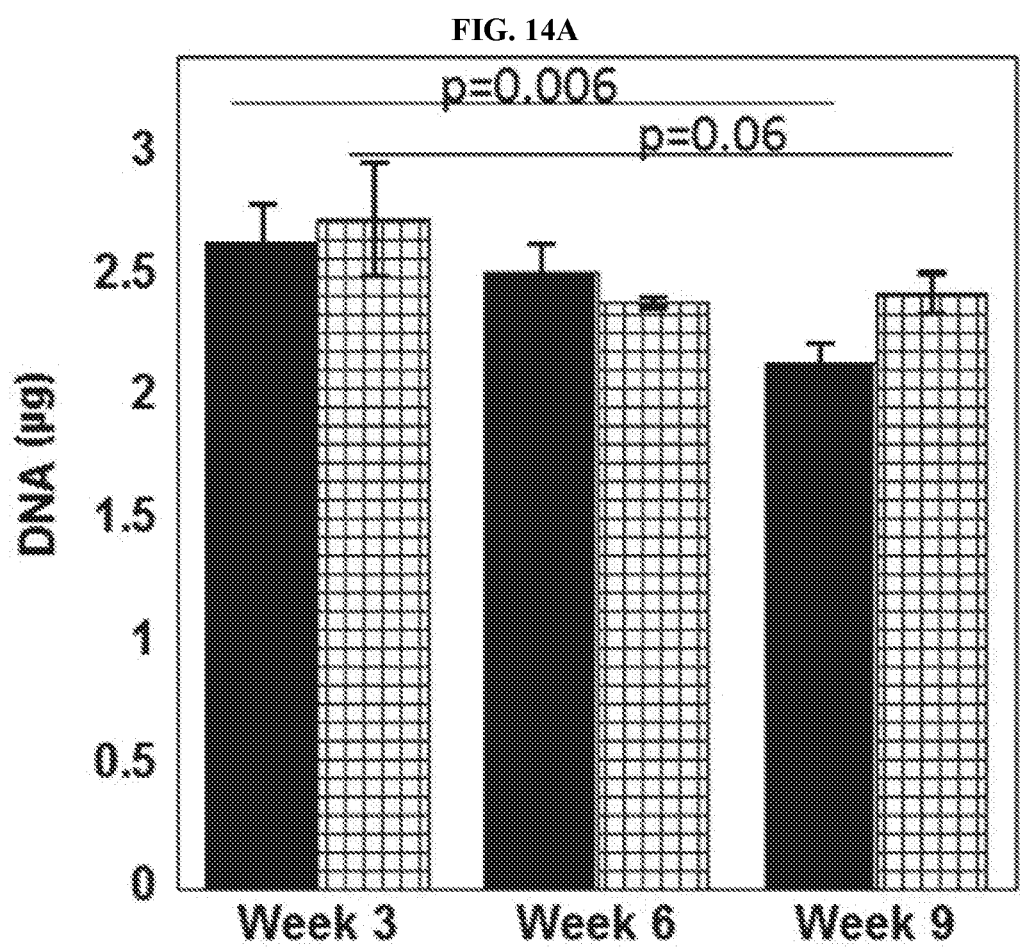
FIG. 14A is a graph showing DNA content in the hydrogels with soluble TGF-β3 (solid) or tethered TGF-β3 (striped) throughout the culture period. Data is represented as the mean with error bars representing the standard deviation (n=3).
Figure 14B:
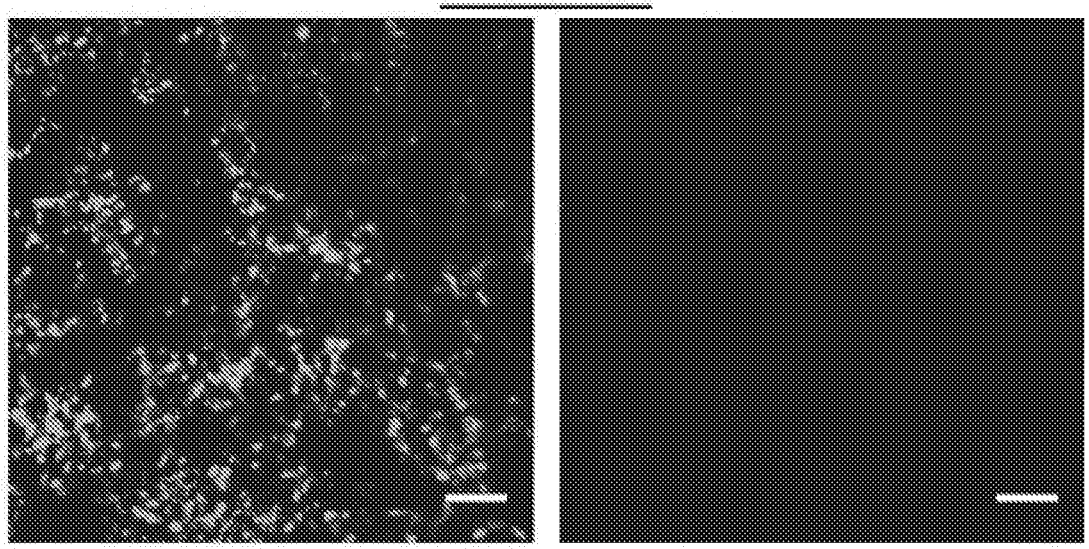
FIG. 14B is a set of representative images of live (green) and dead (red) MSCs encapsulated in the hydrogels after 9 weeks of culture (n=3).
Figure 14B:
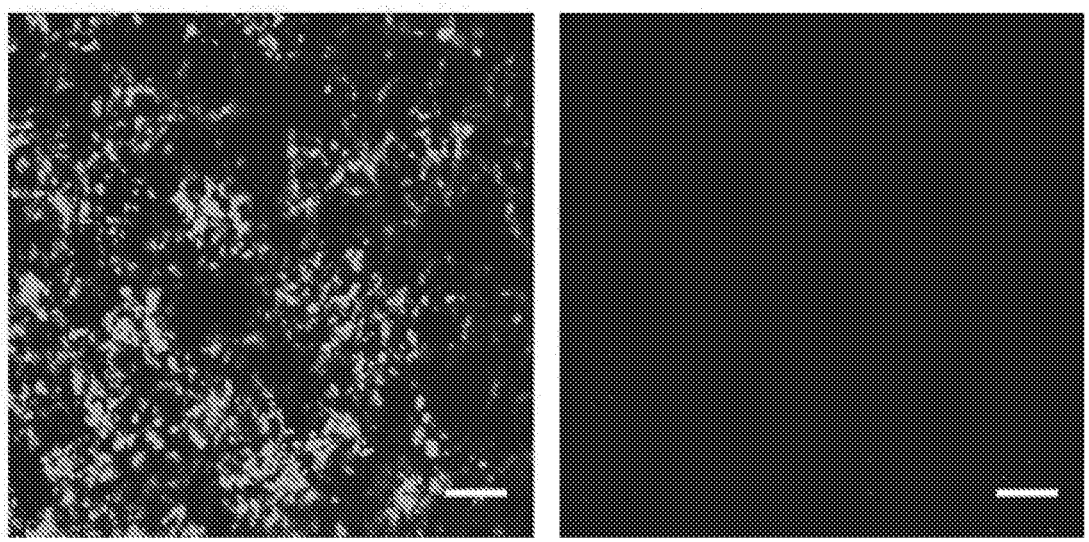

Rat MSCs were encapsulated in a MMP2 sensitive cartilage mimetic poly(ethylene glycol) thiol-norbornene (PEG thiol-ene) hydrogel with either soluble or tethered TGF-β3. DNA content in the hydrogels was investigated to evaluate cell proliferation and cell loss whether by degradation or cell death (FIG. 14A). From week 3 to week 6, there were no significant changes in DNA content in either of the hydrogel cultures. However, by week 9, there was a significant decrease in DNA from week 3 in cell-laden hydrogels cultured with soluble TGF-β3 (p=0.006). DNA content also decreased in the hydrogels with tethered-TGF-β3 by week 9 (p=0.06). At the end of the experiment at 9 weeks, encapsulated MSCs remained viable in the hydrogels with tethered or soluble TGF-β3 with few dead cells (FIG. 14B). Cell viability appeared similar in the two TGF-β3 conditions.

Figure 15A:
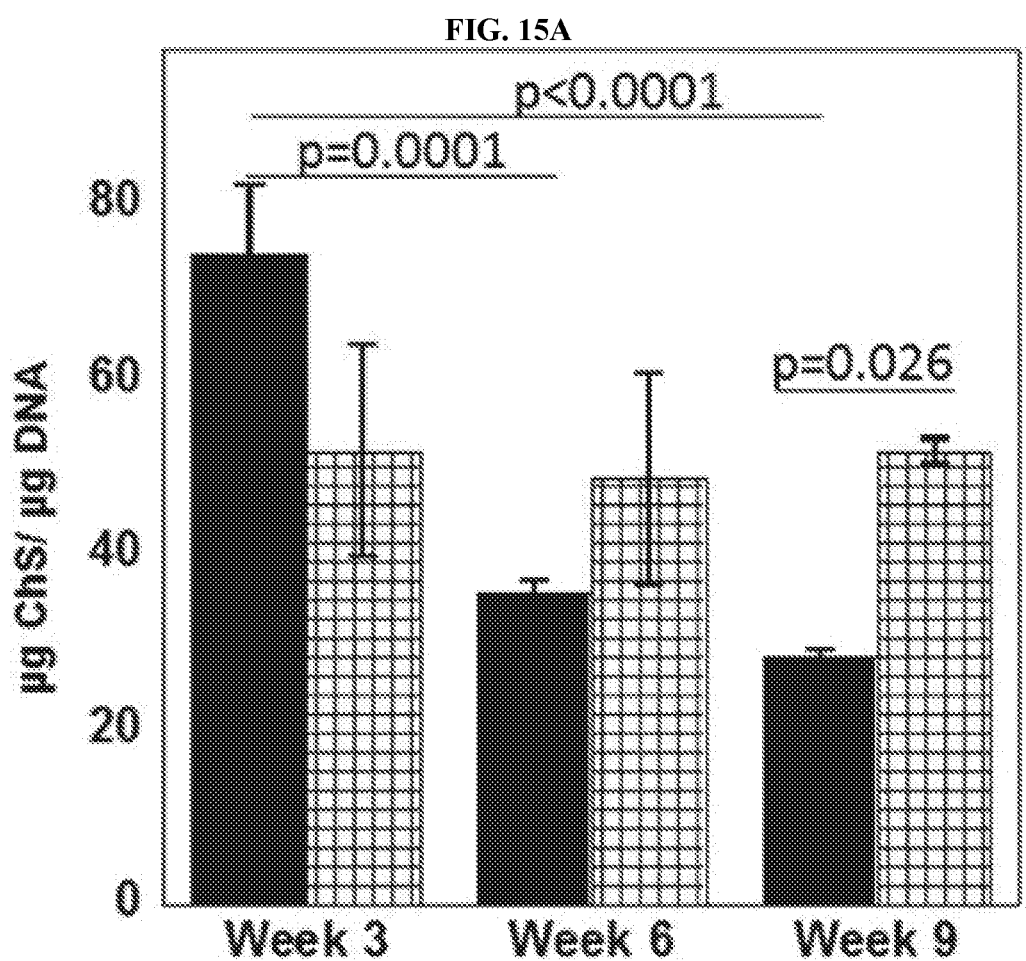

The deposition of ChS in the hydrogels was also investigated (FIG. 15A). In the hydrogels cultured with soluble TGF-β3, there was a decrease in sGAGs from week 1 to week 6 and week 9 (p=0.0001 and p<0.0001, respectively). In contrast, in the hydrogels with tethered-TGF-β3, sGAGs deposition at week 3 was maintained throughout the remainder of the study. At week 9, the amount of ChS in the hydrogels with tethered TGF-β3 was higher than in hydrogels cultured with soluble TGF-β3 (p=0.026). This biochemical analysis of ChS deposition coincides with safranin O histology, which was used to evaluate sGAGs retained in the hydrogel (FIG. 15B). The incorporation of ChS in the hydrogel results in a basal level of positive stain. At 3 weeks of culture, sGAG deposition was evident in both TGF-β3 conditions. MSCs cultured in hydrogels with soluble TGF-β3 showed regions of positive stain that were adjacent to areas of little to no positive staining. MSCs cultured in hydrogels with tethered TGF-β3 showed a more uniform sGAG deposition throughout the hydrogel. By week 6, MSCs in hydrogels with soluble TGF-β3 showed a reduction in sGAGs retention from week 3, and by week 9 there were even fewer regions of deposited sGAGs in the hydrogel. In contrast, hydrogels with tethered TGF-β3 retained sGAGs from week 3, to week 6 and week 9 of culture, and exhibited observably more sGAGs than MSCs cultured with TGF-β3 in the media.

Figure 16A:
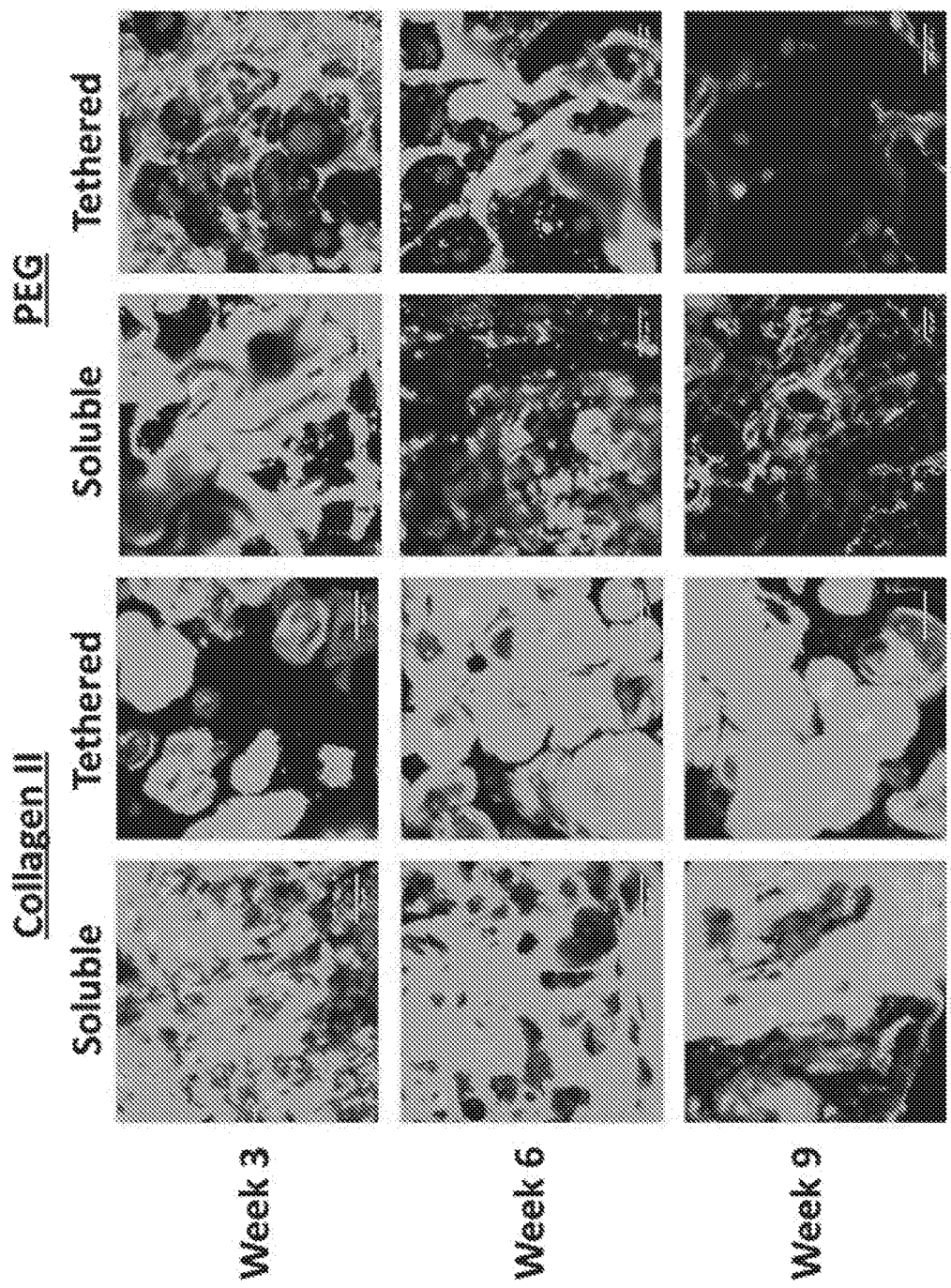
FIGS. 16A-16C are images and graphs of immunohistochemical analysis of collagen II and poly(ethylene)glycol (PEG) in the hydrogels of the invention.
Figure 16C:
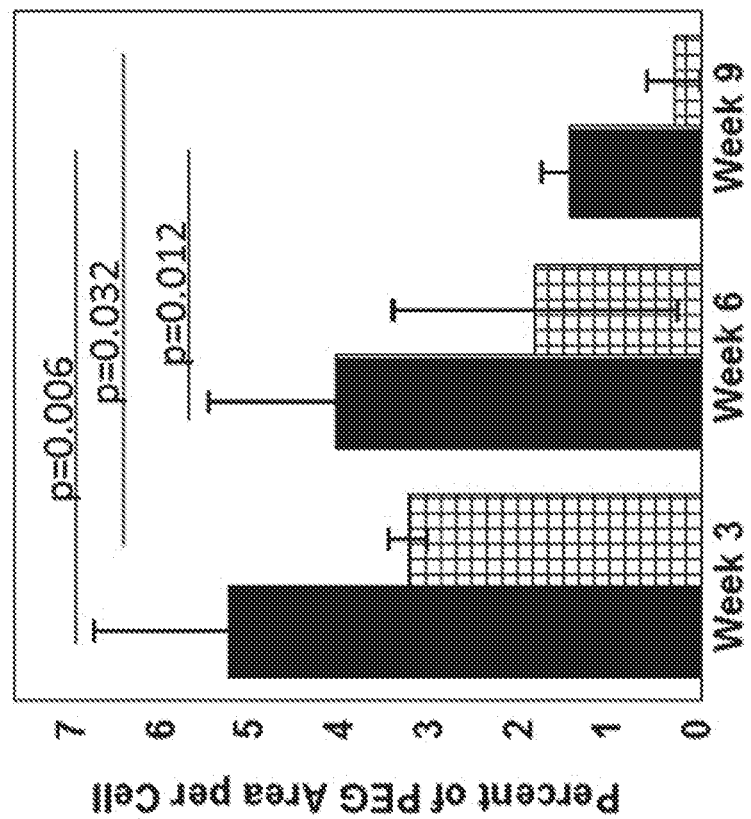
Figure 16B:
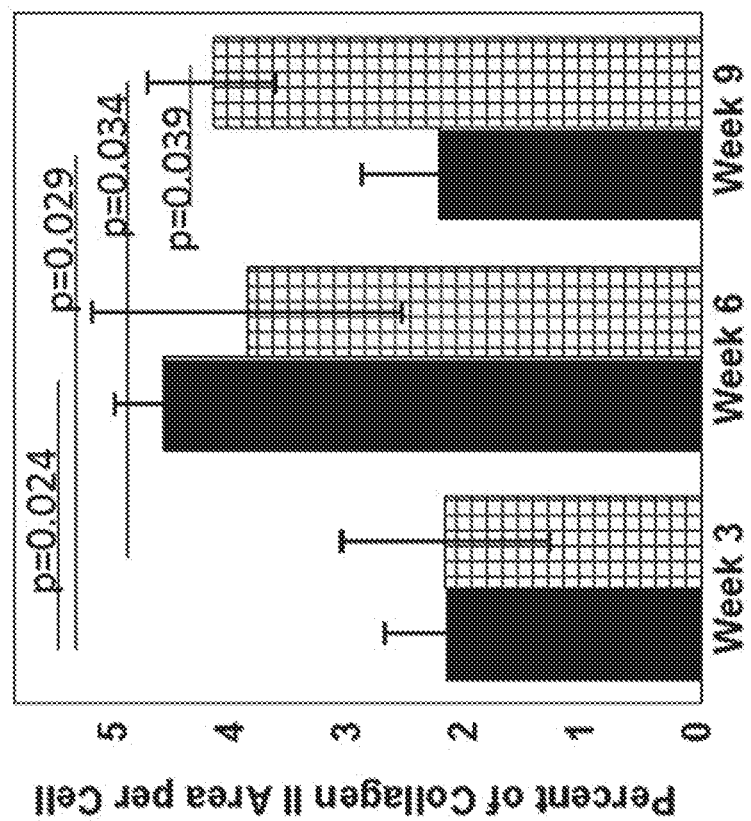

Cartilaginous ECM deposition by encapsulated rat MSCS was analyzed and, as a result, indicated chondrogenic differentiation. After 3 weeks of culture, collagen II was present in both hydrogel cultures (FIG. 16A). Semi-quantitative analysis of collagen II stained sections indicated an increase in collagen II area per cell for MSCs cultured in the hydrogels with soluble TGF-β3 from week 3 to week 6 (p=0.024) (FIG. 16B). However, from week 6 to week 9 there was a significant decrease in collagen II area per cell when cultured with soluble TGF-β3. Collagen II was produced by MSCs encapsulated in the hydrogels with tethered TGF-β3 at week 3 and week 6. By week 9, there was an increase in collagen II area per cell in the tethered-TGF-β3 hydrogel from week 3 (p=0.034). Additionally, MSCs encapsulated in hydrogels with tethered TGF-β3 had significantly more collagen II area per cell at week 9 than those cultured with soluble TGF-β3 in the media (p=0.039). The spatial deposition of the collagen II produced by MSCs encapsulated in hydrogels with tethered TGF-β3 also differed from those cultured with soluble TGF-β3 and resembled that of hyaline-like cartilage (FIG. 16A).

Sections were also stained for PEG to examine temporal degradation behavior of the hydrogel (FIG. 16A). PEG was present in both growth factor conditions after 3 weeks. Although not significant, by week 6, the percent area of PEG per cell was decreased in both hydrogels (FIG. 16C). After 9 weeks, there was a significant decrease in the percent area of PEG per cell from week 3 and week 6 in hydrogels cultured with soluble TGF-β3 (p=0.006 and p=0.012, respectively). In hydrogels with tethered TGF-β3, the percent area of PEG per cell significantly decreased from week 3 to week 9 (p=0.032).

Figure 17:
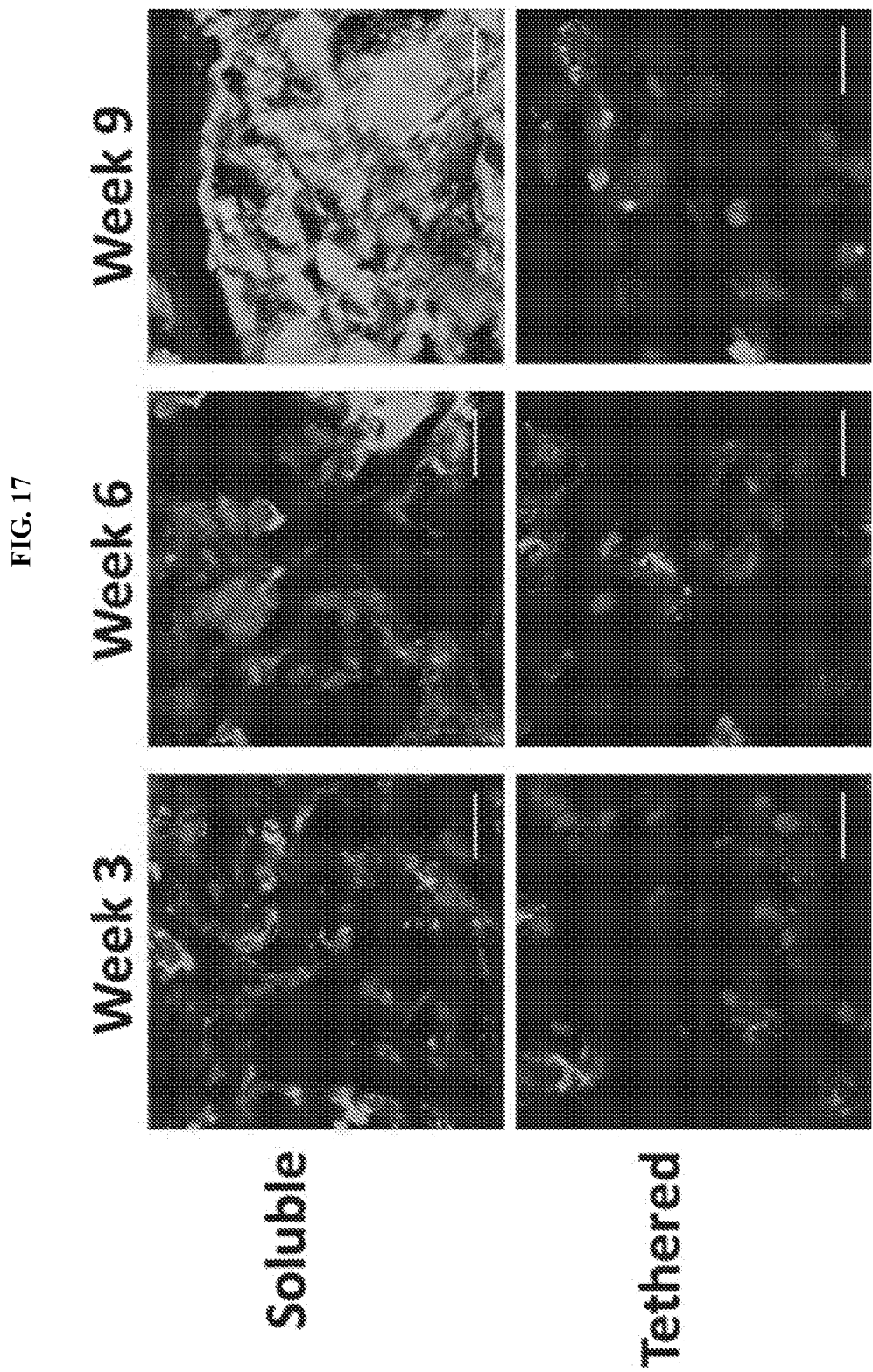
FIG. 17 is a set of representative immunohistochemistry images of collagen I (green) when cultured with tethered TGF-β3 and soluble TGF-β3 at week 3, 6, and 9 (scale bar=20 μm).

In addition to collagen II, IHC analysis of collagen I was done to evaluate the formation of fibrocartilage (FIG. 17). MSCs cultured with soluble TGF-β3 showed increased collagen I deposition from week 3 to week 9. By week 9 of culture, collagen I was prevalent and interconnected throughout the construct. Collagen I was also present in the tethered TGF-β3, however, the amount of collagen I was observably lower and appeared to be localized to the pericellular space and not spread out throughout the construct.

Figure 18:
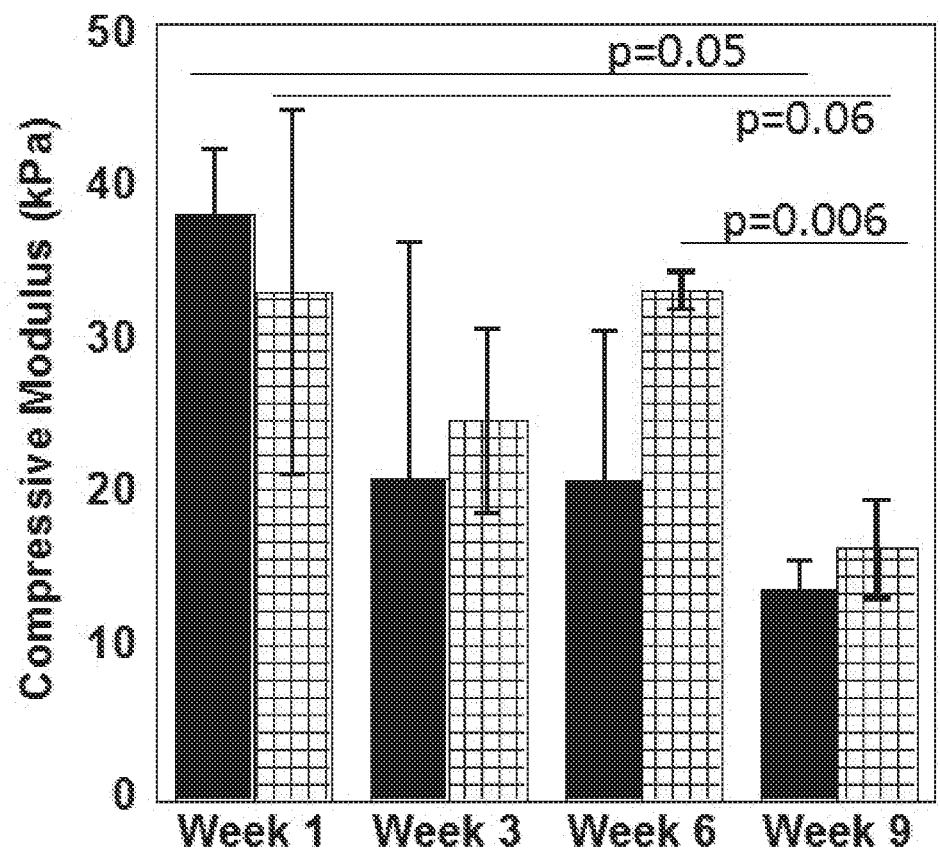
FIG. 18 is a graph showing the compressive modulus of the cell-laden hydrogels with soluble TGF-β3 (solid) or tethered TGF-β3 (striped) throughout the culture period. Data is represented as the mean with error bars representing the standard deviation (n=3).

The compressive modulus of the hydrogels was evaluated over the course of the study (FIG. 18). After 1 week of culture, the modulus was similar in both hydrogel networks (~35-40 kPa). Although not significant, from week 1 to week 3, hydrogels cultured with soluble TGF-β3 decreased and remained at a similar compressive modulus to week 6. However, by week 9, the compressive modulus had dropped by ~2-fold from week 1, to approximately 15 kPa (p=0.05). Hydrogels with tethered TGF-β3 maintained their compressive modulus from week 1 to week 6 (~35 kPa). However, by week 9, there was a decrease in modulus to approximately 15 kPa (p=0.006). By week 9, the compressive modulus was similar in both TGF-β3 conditions.

Repair Tissue after Injection of Cartilage Mimetic Hydrogel in Injured Physis

Figure 19B:
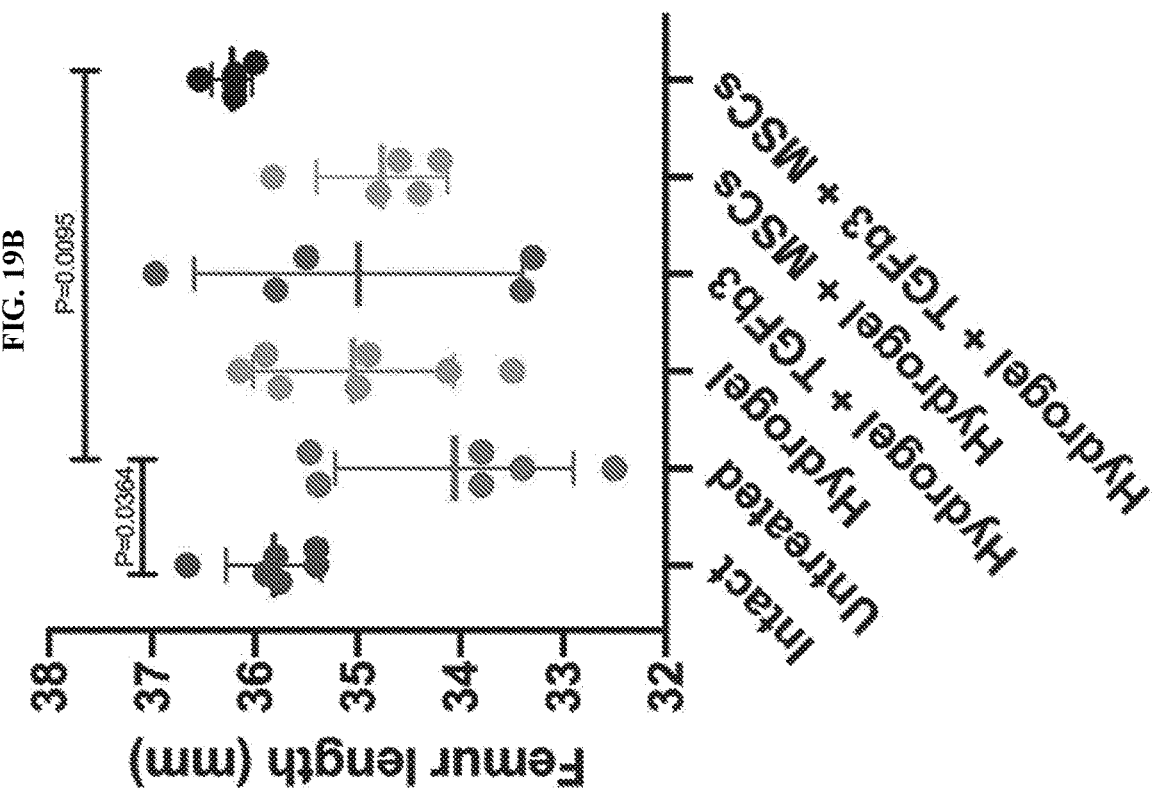
FIGS. 19A-19B are graphs showing Bone Volume Fraction (BVF) within rat injured physis 28 days after treatment (FIG. 19A) and femur length 28 days after treatment (FIG. 19B). All data is represented as the mean with standard deviation (n=5-7). *P<0.05 compared to Intact, **P<0.001 compared to Intact, # P<0.05 compared to Untreated, ## P<0.001 compared to Untreated, and +P<0.05 compared to Hydrogel.
Figure 19A:
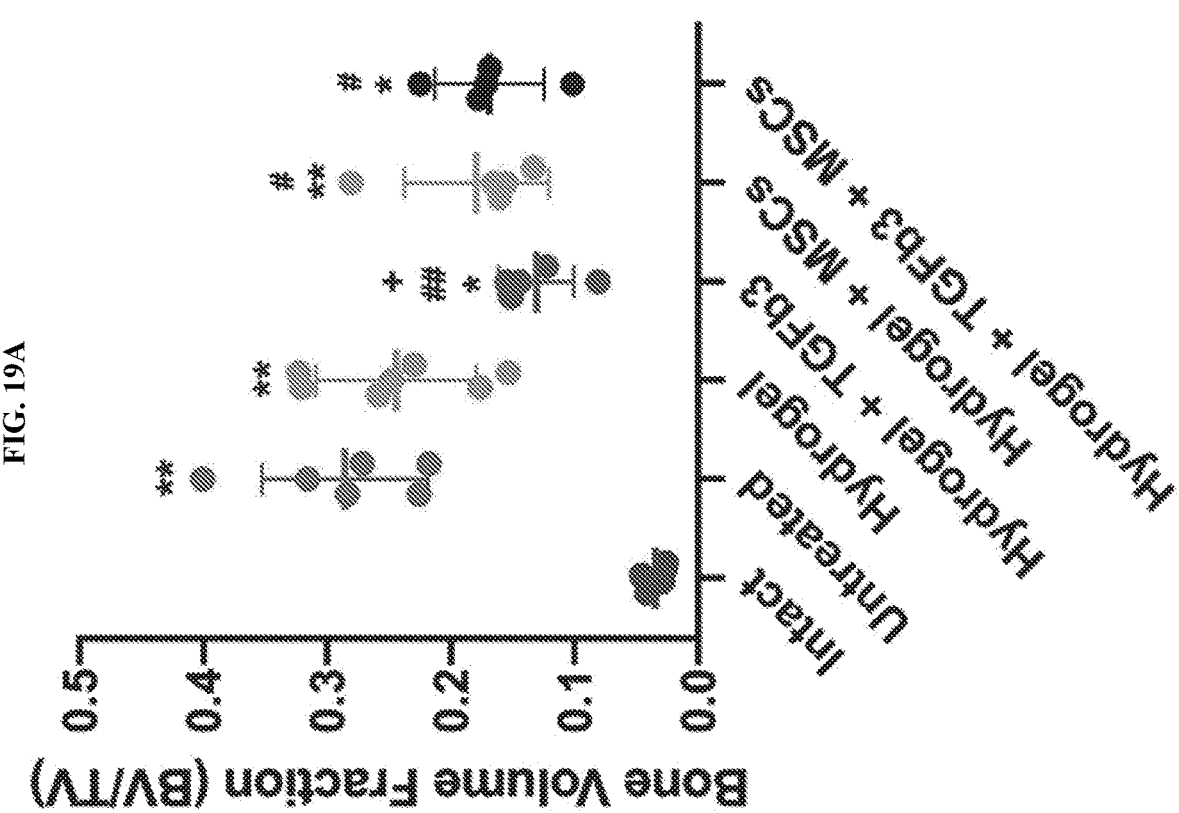

The ability of the hydrogel to be delivered in vivo and promote chondrogenesis in an injured physis was tested using a rat model of femoral physeal injury. In this study, the hydrogel was easily delivered and photopolymerized in situ in a sterile manner. Only one animal did not reach the study end point and was removed from the study. Of the animals that reached the study end point of 28 days, there was no evidence of synovial reaction by macroscopic observation. Micro-CT analysis provided quantitative measurement of the amount of bony tissue formed within the injured area of the physis, known as bone volume fraction (BVF), and also provided information on the femoral bone length (FIGS. 19A-19B). All groups were significantly different than Intact (FIG. 19A, *P<0.05 and **P<0.001). The groups containing hydrogel with TGF-β3 (with and without MSCs), as well as the Hydrogel+MSCs group had a BVF that was significantly reduced compared to the Untreated group (FIG. 19A, # P<0.05 and ## P<0.001). The Hydrogel+TGF-β3 group showed the lowest BVF, and was significantly different than the Hydrogel group (FIG. 19A, +P<0.05). Femur length was significantly reduced in the Untreated group when compared to the Intact group (FIG. 19B, P=0.0364). All treatment groups showed a trend of increased femur length when compared to Untreated, with the Hydrogel+TGF-β3+MSCs group being significantly greater than Untreated (FIG. 19B, P=0.0095).

Figure 20:
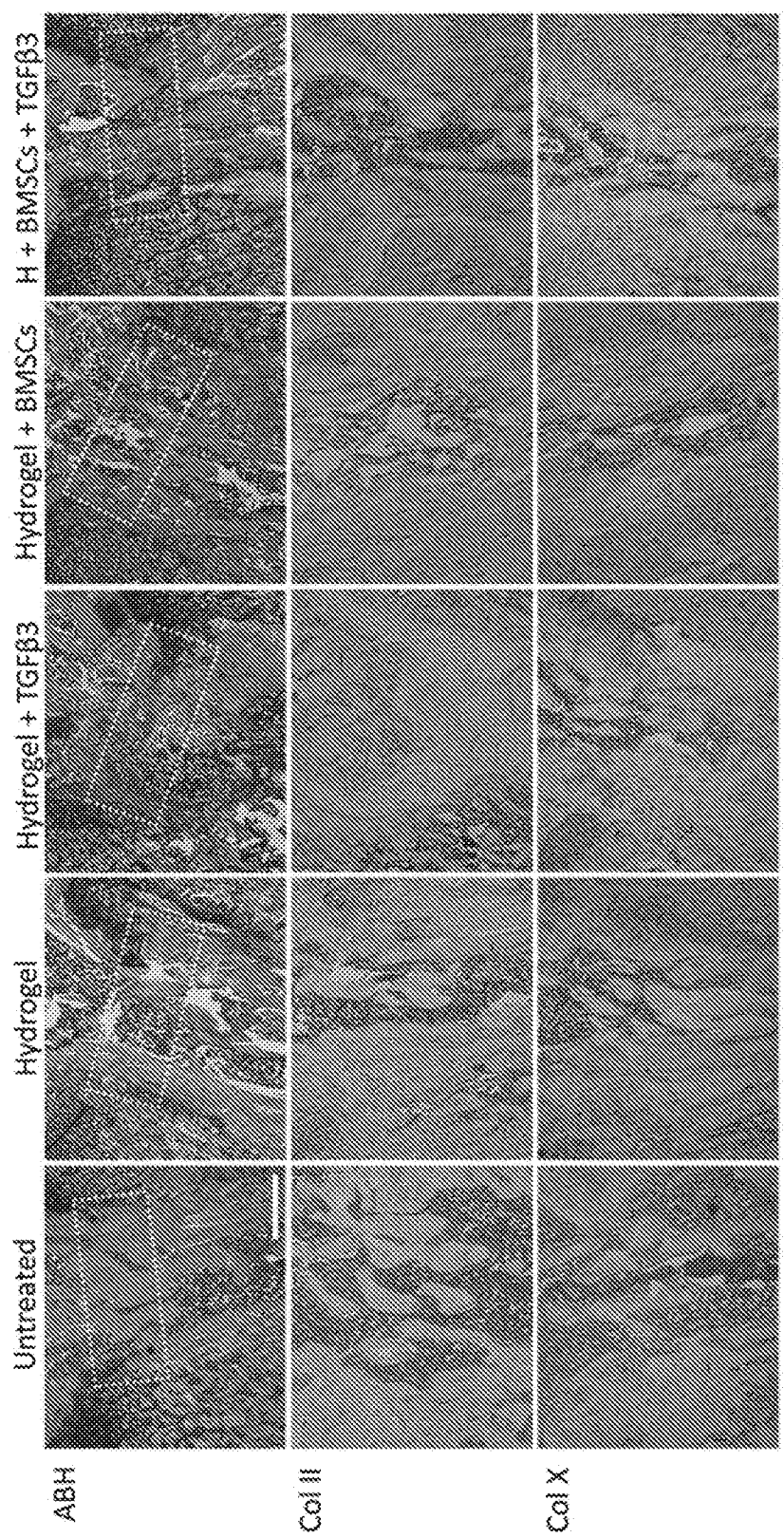
FIG. 20 is a set of Alcian Blue Hematoxylin and immunohistochemistry images for Collagen II and X of rat physeal injuries (GPIs). Magnification 4× and white scale bar is 500 Alcian Blue-Hematoxylin (ABH) stain: blue, glycosaminoglycans; pink-red, bone; light purple, fibrous tissue formation. Yellow boxed areas represent GPIs; adjacent to this, healthy physis (blue). Collagen II (Col II): brown. Collagen X (Col X): brown.

The repair tissue that formed within the injured physis was evaluated using ABH staining, where a blue color is indicative of cartilaginous tissue, an orange to red color is evidence of bone tissue, while a pink color represents fibrous tissue. (FIG. 20, top row). Bony tissue was most evident in the Untreated group, with a reduction in bony tissue seen in all treatment groups, especially the injuries treated with Hydrogel+TGF-β3. New cartilage formation was observed in both groups containing TGF-β3, with a significant amount of cartilage-like tissue in the Hydrogel+TGF-β3 group. Almost the entire repair tissue area was stained blue for cartilage or light-purple for fibrous-like tissue. The repair tissue within the injury site was further characterized for the presence of Collagen II and X (FIG. 20, middle and bottom row, respectively). While both collagens were present in the uninjured physis, they were not widely apparent in the repair tissue area.

Disclosure

Results reported herein suggest that tethering TGF-β3 into a degradable cartilage mimetic hydrogel promotes chondrogenesis and encourages matrix deposition of encapsulated rat MSCs to a greater extent than hydrogels cultured with soluble TGF-β3. Environmental cues often come from recapitulating the native tissue. For instance, cartilage tissue is primarily made up of collagen II, hyaluronic acid, and aggrecan, which is also comprised of the highly negative charged GAG ChS. It is responsible for the fixed negative charge which results in an increase in local osmolarity, water retention, and compressive properties of cartilage. Studies have investigated incorporating one or more of these ECM analogs into hydrogels in order to create a biomimetic environment that allows for MSC chondrogenesis. By locally presenting the encapsulated MSCs with the tethered TGF-β3 in addition to the ECM analogs, ChS and RGD, the results reported herein show, quantitatively and qualitatively, that MSCs chondrogenically differentiate and produce their own cartilage matrix while degrading the synthetic hydrogel scaffold in vitro. The matrix produced by the cells encapsulated in the TGF-β3-tethered hydrogels was able to retain GAGs and deposit more collagen II when compared to the cell-laden hydrogels cultured in media containing soluble TGF-β3. Additionally, soluble TGF-β3 resulted in the formation of fibrocartilage, whereas the matrix deposited in the tethered TGF-β3 hydrogels was similar to that of hyaline-like cartilage. The binding of TGF-β to its receptor is necessary for many cellular signaling mechanisms that are imperative to chondrogenesis such as Smad signaling. Negatively charged extracellular matrix molecules in native hyaline cartilage are known to interact and sequester soluble growth factors from the surrounding fluid. Without intending to be limited to any particular theory, the local presentation of the tethered TGF-β3 to the encapsulated cells may recapitulate the presentation of growth factors found in native cartilage tissue and further enhance chondrogenesis and extracellular matrix elaboration.

Despite both culture systems resulting in collagen II expression, there were marked differences in its distribution. The collagen II produced in the tethered TGF-β3 hydrogels was rounded, similar to hyaline-like cartilage, whereas, the distribution in the hydrogels cultured with soluble TGF-β3 exhibited more of a sheet-like distribution of collagen II, reminiscent of fibrocartilage. The IHC analysis of collagen I further confirmed the deposition of fibrocartilage in the soluble TGF-β3 construct, where collagen I was prevalent and interconnected through the constructs. Although collagen I was present in the TGF-β3 tethered constructs, the amount of collagen I was observably lower and appeared to be more localized to the pericellular space. These results suggest that tethered TGF-β3 may promote hyaline-like cartilaginous matrix production by encapsulated MSCs.

In order for a degradable hydrogel to be beneficial in situ, the rate of degradation should match tissue growth to maintain structural integrity. The PEG staining studies suggest that with tethered TGF-β3, the cells appear to be degrading the PEG locally around the deposited matrix. In contrast, hydrogels cultured in soluble TGF-β3 show large areas of degradation. While the mechanism is not fully understood, there was an observable difference in the degradation of the hydrogel. Without intending to be limited to any particular theory, this could be a function of many parameters including enzymes secreted, enzyme concentration, and ECM deposition.

TGF-β3 was covalently tethered into the hydrogel at a much higher concentration (50 nM) than the TGF-β3 was provided to the media (1 nM). The TGF-β3 in the media was replenished every other day for the duration of the study therefore maintaining its activity. Alternatively, the presence of the tethered TGF-β3 was dependent on the degradation of the hydrogel. Once the degradable hydrogel reached its reverse gelation point, bulk degradation occurred and TGF-β3 was no longer present within the construct. Therefore, there may be a temporal response of the amount of TGF-β3 presented to the cells. Studies have shown TGF-β3 is necessary to initiate chondrogenesis and matrix deposition. However, long-term exposure to high concentrations of TGF-β3 can drive the differentiation into a hypertrophic phenotype. Without intending to limited to any particular theory, it is postulated that the tethered TGF-β3 promotes chondrogenesis during initial stages of differentiation, and as the matrix degrades, lower concentrations of TGF-β3 are present. The lower concentration of TGF-β3 may enhance GAG content and prevent hypertrophy. The in vitro data suggests that the degradable, cartilage mimetic PEG thiol-ene hydrogel with tethered TGF-β3 is a potential tissue engineering strategy for in vivo cartilage repair. The tethered TGF-β3 hydrogel will be advantageous as it provides the necessary cues without the need for additional soluble growth factor treatment.

To test the ability of the cartilage mimetic hydrogel to form cartilaginous tissue in vivo, a cartilage physeal injury model was used, which represented a significant clinical problem in pediatric orthopedic patients. Once physeal cartilage is damaged, it can repair with bony tissue which can have devastating effects on bone lengthening. Current clinical treatments attempt to remove the bony tissue and replace it with interpositional materials that often degrade and make room for bone to reform. There is no treatment that attempts to regenerate cartilage tissue, creating an opportunity to develop novel biomaterial-based regenerative medicine approaches such as our cartilage biomimetic hydrogel. As reported herein, the cartilage-mimetic hydrogel was delivered with and without tethered TGF-β3, as well as with and without exogenous MSCs in a distal femoral rat physeal injury to prevent bone tissue formation and enhance cartilage tissue formation.

Injection of the cartilage mimetic hydrogel served as a good interpositional material after injury, as seen by less bony tissue in the injured area by histological analysis compared to untreated. Quantitative measurements of bony repair tissue indicated that the presence of TGF-β3 and MSCs was necessary to have a significant decrease in BVF compared to untreated. The groups with TGF-β3 were the only treatment groups where new cartilaginous repair tissue was formed, further suggesting the importance of TGF-β3 for physeal cartilage regeneration. It has been shown that after physeal injury in the rat, MSCs from adjacent marrow compartments can migrate to the injury site, undergo osteogenesis and form bony repair tissue. This suggests that endogenous MSCs entering the injured area may have interacted with the cartilage biomimetic hydrogel and when presented with TGF-β3, were directed away from an osteogenic lineage and towards the chondrogenic lineage. This resulted in less bone formation and increased cartilage formation. The addition of the hydrogel promoted bone elongation when compared to untreated. The addition of TGF-β3 and MSCs had the greatest increase in femur length, suggesting that the addition of a chondrogenic factor and MSCs may be needed to maintain bone elongation after physeal injury.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A biomimetic cartilage construct comprising a 3D printed structure in-filled with a cartilage mimetic hydrogel, wherein:
   the 3D printed structure comprises an array of support pillars and at least two connecting lattice structures located at the top and base;
   the 3D printed structure is printed into a three-dimensional shape having at least about 75% of the volume of the shape configured as open area available for in-filling with the cartilage mimetic hydrogel, wherein the three-dimensional shape is configured to provide structural support against longitudinal compressive forces and to provide lateral support against transverse movement during use;
   the 3D printed structure being formed from at least one photopolymerizable material, the photopolymerizable material comprising at least one oligomeric or monomer material functionalized with at least one functionality selected from the group consisting of acrylate, methacrylate, thiol and norbornene; and
   the cartilage mimetic hydrogel being formed from at least one multifunctional monomer and at least one degradable cross-linker.

2. The construct of claim 1, wherein the 3D printed structure is printed into a pattern or shape selected from the group consisting of a honeycomb, grid, and mesh.

3. The construct of claim 1, wherein the 3D printed structure comprises at least one biodegradable material.

4. The construct of claim 1, wherein the at least one multifunctional monomer comprises at least one material selected from the group consisting of poly(ethylene glycol), poly(ethylene glycol) diacrylate, poly(ethylene glycol) methacrylate, acryloyl-PEG-RGD, norbornene functionalized PEG.

5. The construct of claim 1, wherein the at least one degradable cross-linker is an enzyme degradable peptide.

6. The construct of claim 5, wherein the enzyme degradable peptide is a peptide that can be degraded by at least one matrix metalloproteinase.

7. The construct of claim 5, wherein the enzyme degradable peptide is selected from the group consisting of GCVPLSLYSGCG (SEQ ID NO: 13), CVPLSLYSGC (SEQ ID NO: 14) and CRGDS (SEQ ID NO: 15).

8. The construct of claim 1, wherein the cartilage mimetic hydrogel comprises at least one biomimetic moiety selected from the group consisting of chondroitin sulfate, thiolated chondroitin sulfate, methacrylated chondroitin sulfate, and cell adhesion peptide RGD.

9. The construct of claim 1, wherein the cartilage mimetic hydrogel comprises at least one biological factor selected from the group consisting of SDF-1α, CCL25, TGF-β1, TGF-β3, ranibizumab, bevacizumab, lapatinib, sunitinib, sorafenib, axitinib, and pazopanib.

10. The construct of claim 9, wherein at least a portion of the at least one biological factor is covalently bound to the cartilage mimetic hydrogel.

11. The construct of claim 1, further comprising mesenchymal stem cells.

12. A method of treating a cartilage injury in a subject, the method comprising placing the construct of claim 1 in a void at the site of the cartilage injury.

13. The method of claim 12, wherein, the cartilage injury is a growth plate injury.

14. The method of claim 13, wherein, before the placing step, a bony bar is first surgically removed from the growth plate injury in the subject, thus generating, at least in part, the void.

15. The method of claim 13, wherein, before the placing step, damaged growth plate cartilage is first surgically removed from the site of the growth plate injury, thus generating, at least in part, the void.

16. The method of claim 13, which minimizes, reverses, or ameliorates at least one of the following:
   growth of bony bars in cartilage tissue at the site of growth plate injury;
   arrest of bone growth at the site of growth plate injury; and
   bone deformities at the site of growth plate injury.

17. The method of claim 13, wherein the subject is an infant, toddler, child, juvenile, adolescent, or young adult.

18. The method of claim 12, wherein the subject is a mammal.

19. The method of claim 17, wherein the subject is a human.

20. The construct of claim 1, wherein the 3D printed structure comprises an array of support pillars and a connecting lattice structure located at least at the base, middle and top.

21. The construct of claim 20, wherein the array of support pillars is configured to provide structural support against longitudinal compressive forces and the connecting lattice structure is configured to provide lateral support against transverse movement during use.

* * * * *

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: L30 Primer Forward Seq.

<400> SEQUENCE: 1
ttagcggctg ctgttggtt                                                    19

<210> SEQ ID NO 2
<211> LENGTH: 21
<212> TYPE: DNA
<213> ORGANISM: Artificial Sequence
<220> FEATURE:
<223> OTHER INFORMATION: L30 Primer Reverse Seq.

<400> SEQUENCE: 2
tccagcgact ttttcgtctt c                                                 21

<210> SEQ ID NO 3
<211> LENGTH: 23
<212> TYPE: DNA
<213> ORGANISM: Artificial Sequence
<220> FEATURE:
<223> OTHER INFORMATION: SOX9 Primer Forward Seq.

<400> SEQUENCE: 3
tgacctatcc aagcgcatta cca                                               23

<210> SEQ ID NO 4
<211> LENGTH: 24
<212> TYPE: DNA
<213> ORGANISM: Artificial Sequence
<220> FEATURE:
<223> OTHER INFORMATION: SOX9 Primer Reverse Seq.

<400> SEQUENCE: 4
atcatcctcc acgcttgctc tgaa                                              24

<210> SEQ ID NO 5
<211> LENGTH: 25
<212> TYPE: DNA
<213> ORGANISM: Artificial Sequence
<220> FEATURE:
<223> OTHER INFORMATION: ACAN Primer Forward Seq.

<400> SEQUENCE: 5
agtatcatcg tcccagaatc tagca                                             25

<210> SEQ ID NO 6
<211> LENGTH: 22
<212> TYPE: DNA
<213> ORGANISM: Artificial Sequence
<220> FEATURE:
<223> OTHER INFORMATION: ACAN Primer Reverse Seq.

<400> SEQUENCE: 6
```
aatgcagagg tggtttcact ca					22

<210> SEQ ID NO 7
<211> LENGTH: 21
<212> TYPE: DNA
<213> ORGANISM: Artificial Sequence
<220> FEATURE:
<223> OTHER INFORMATION: COL2A1 Primer Forward Seq.

<400> SEQUENCE: 7
caacactgcc aacgtccaga t					21

<210> SEQ ID NO 8
<211> LENGTH: 24
<212> TYPE: DNA
<213> ORGANISM: Artificial Sequence
<220> FEATURE:
<223> OTHER INFORMATION: COL2A1 Primer Reverse Seq.

<400> SEQUENCE: 8
tcttgcagtg gtaggtgatg ttct				24

<210> SEQ ID NO 9
<211> LENGTH: 20
<212> TYPE: DNA
<213> ORGANISM: Artificial Sequence
<220> FEATURE:
<223> OTHER INFORMATION: RUNX2 Primer Forward Seq.

<400> SEQUENCE: 9
ttggcctggt ggtgtcatta					20

<210> SEQ ID NO 10
<211> LENGTH: 20
<212> TYPE: DNA
<213> ORGANISM: Artificial Sequence
<220> FEATURE:
<223> OTHER INFORMATION: RUNX2 Primer Reverse Seq.

<400> SEQUENCE: 10
gagtccttct gtggcatgca					20

<210> SEQ ID NO 11
<211> LENGTH: 24
<212> TYPE: DNA
<213> ORGANISM: Artificial Sequence
<220> FEATURE:
<223> OTHER INFORMATION: COL10A1 Primer Forward Seq.

<400> SEQUENCE: 11
ttttgctgct agtatccttg aact				24

<210> SEQ ID NO 12
<211> LENGTH: 20
<212> TYPE: DNA
<213> ORGANISM: Artificial Sequence
<220> FEATURE:
<223> OTHER INFORMATION: COL10A1 Primer Reverse Seq.

<400> SEQUENCE: 12
acctctaggg ccagaaggac					20